United States Patent
Pulukuri

(10) Patent No.: US 12,419,890 B2
(45) Date of Patent: Sep. 23, 2025

(54) ADMINISTRATION OF SUMO-ACTIVATING ENZYME INHIBITOR AND CHECKPOINT INHIBITORS

(71) Applicant: Takeda Pharmaceutical Company Limited, Osaka (JP)

(72) Inventor: Sai Murali Krishna Pulukuri, Sharon, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 964 days.

(21) Appl. No.: 17/433,042

(22) PCT Filed: Feb. 27, 2020

(86) PCT No.: PCT/US2020/020171
§ 371 (c)(1),
(2) Date: Aug. 23, 2021

(87) PCT Pub. No.: WO2020/176772
PCT Pub. Date: Sep. 3, 2020

(65) Prior Publication Data
US 2022/0233531 A1    Jul. 28, 2022

Related U.S. Application Data

(60) Provisional application No. 62/811,303, filed on Feb. 27, 2019.

(51) Int. Cl.
*A61K 31/506* (2006.01)
*A61P 35/00* (2006.01)
*C07K 16/28* (2006.01)

(52) U.S. Cl.
CPC ............ *A61K 31/506* (2013.01); *A61P 35/00* (2018.01); *C07K 16/2818* (2013.01); *C07K 16/2827* (2013.01)

(58) Field of Classification Search
CPC .... A61P 35/00; C07K 16/281; C07K 16/2827
See application file for complete search history.

(56) References Cited

U.S. PATENT DOCUMENTS

| 8,217,149 B2 | 7/2012 | Irving et al. |
| 9,434,765 B2 | 9/2016 | Rodriguez Medina |
| (Continued) | | |

FOREIGN PATENT DOCUMENTS

| CN | 101072561 A | 11/2007 |
| JP | 2016540042 A | 12/2016 |
| (Continued) | | |

OTHER PUBLICATIONS

Rosenbaum et al. PD-L1 expression in colorectal cancer is associated with microsatellite instability, BRAF mutation, medullary morphology and cytotoxic tumor-infiltrating lymphocytes. Mod Pathol 29, 1104-1112 (2016). (Year: 2016).*

(Continued)

*Primary Examiner* — Joseph K McKane
*Assistant Examiner* — Ashli Ariana Chicks
(74) *Attorney, Agent, or Firm* — Sterne, Kessler, Goldstein &Fox P.L.L.C.

(57) ABSTRACT

The present disclosure provides methods, pharmaceutical compositions, and kits for treating cancer in patients in need thereof. The methods comprise administering to a patient in need a small ubiquitin-like modifier (SUMO) activating enzyme (SAE) inhibitor, such as [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt, in combination with one or more checkpoint inhibitors. Also provided are medicaments for use in treating cancer.

18 Claims, 34 Drawing Sheets

Anti-tumor activity of Compound I-263a and vehicle in mouse CT26 syngeneic tumor model

(56) References Cited

U.S. PATENT DOCUMENTS

| | | | |
|---|---|---|---|
| 9,683,003 B2 * | 6/2017 | Duffey | C07D 495/04 |
| 9,695,154 B2 | 7/2017 | Duffey et al. | |
| 10,335,410 B2 * | 7/2019 | Duffey | C07F 9/5442 |
| 2010/0160177 A1 | 6/2010 | Merbl et al. | |
| 2016/0009744 A1 | 1/2016 | Duffey et al. | |
| 2018/0311239 A1 | 11/2018 | Duffey et al. | |
| 2018/0327411 A1 | 11/2018 | Castro et al. | |

FOREIGN PATENT DOCUMENTS

| | | |
|---|---|---|
| WO | WO-2006042150 A1 | 4/2006 |
| WO | WO-2015069770 A1 | 5/2015 |
| WO | WO-2016004136 A1 | 1/2016 |
| WO | WO-2017059224 A2 | 4/2017 |
| WO | WO-2017139231 A1 | 8/2017 |
| WO | WO-2018154529 A1 | 8/2018 |
| WO | WO-2020176772 A1 | 9/2020 |

OTHER PUBLICATIONS

Clinical Trials NCT02563002, "Study of Pembrolizumab (MK-3475) vs Standard Therapy in Participants With Microsatellite Instability-High (MSI-H) or Mismatch Repair Deficient (dMMR) Stage IV Colorectal Carcinoma (MK-3475-177/KEYNOTE-177)," Dec. 8, 2017, accessed at https://clinicaltrials.gov/study/ (Year: 2017).*

Merck Sharpe & Dohme Corporation: Keytruda (pembrolizumab)[package insert] U.S. Food and Drug Administration. https://www.accessdata.fda.gov/drugsatfda_docs/label/2019/125514s040lbl.pdf. Published Feb. 15, 2019. Accessed Oct. 31, 2024. (Year: 2019).*

Xiao et al. The microsatellite instable subset of colorectal cancer is a particularly good candidate for checkpoint blockade immunotherapy. Cancer Discov. 2015;5(1):16-18. (Year: 2015).*

Chou, T.C., Cancer Res., 2010, 70(2), 440-446. (Year: 2010).*

Tallarida, R., Genes & Cancer 2011, 2, 1003-1008. (Year: 2011).*

Ballatore, C., et al., "Tau-mediated Neurodegeneration in Alzheimer's Disease and Related Disorders," Nature Reviews. Neuroscience 8(9), pp. 663-672, Nature Pub. Group, England (2007).

Berge, S.M., et al., "Pharmaceutical Salts," Journal of Pharmaceutical Sciences 66(1):1-19, Wiley, United States (Jan. 1977).

Berger, A.J., et al., abstract #3079 "Pharmacodynamic Evaluation of the Novel SUMOylation Inhibitor TAK-981 in a Mouse Tumor Model," Experimental and Molecular Therapeutics: Novel Antitumor Agents 1 60:788, AACR Annual Meeting, United States (Mar. 2019), 1 page.

Bies, J., et al., "Covalent Attachment of the SUMO-1 Protein to the Negative Regulatory Domain of the C-myb Transcription Factor Modifies Its Stability and Transactivation Capacity," The Journal of Biological Chemistry 277(11), pp. 8999-9009, Elsevier Inc., United States (Mar. 2002).

Blank, C., et al., "Interaction of PD-L1 on Tumor Cells with PD-1 on Tumor-specific T Cells as a Mechanism of Immune Evasion: Implications for Tumor Immunotherapy," Cancer Immunology Immunotherapy 54(4):307-314, Springer-Verlag, Germany (Apr. 2005).

Chen, S. F., et al., "Ubc9 Expression Predicts Chemoresistance in Breast Cancer," Chinese Journal of Cancer 30(9), pp. 638-644, Biomed Central, England (Sep. 2011).

Clinical Trials NCT02628067, "Study of Pembrolizumab (MK-3475) in Participants With Advanced Solid Tumors (MK-3475-158/KEYNOTE-158), "ClinicalTrials.gov, accessed at https://clinicaltrials.gov/ct2/show/NCT02628067, accessed on Jul. 9, 2020, 8 pages.

Desterro, J. M., et al., "SUMO-1 Modification of Ikappabalpha Inhibits NF-kappab Activation," Molecular Cell 2(2), pp. 233-239, Cell Press, United States (Aug. 1998).

Dorval, V., and FRASER, P. E., "Small Ubiquitin-like Modifier (Sumo) Modification of Natively Unfolded Proteins Tau and Alpha-synuclein," The Journal of Biological Chemistry 281(15), pp. 9919-9924, Elsevier, United States (Apr. 2006).

Driscoll, J. J., et al., "The Sumoylation Pathway Is Dysregulated in Multiple Myeloma and Is Associated With Adverse Patient Outcome," Blood 115(14), pp. 2827-2834, Elsevier, United States (Apr. 2010).

Freeman, G.J., et al., "Engagement of the PD-1 Immunoinhibitory Receptor by a Novel B7 Family Member Leads to Negative Regulation of Lymphocyte Activation," The Journal of Experimental Medicine 192(7):1027-1034, The Rockefeller University Press, United States (Oct. 2000).

Gareau, J.R., et al., "The SUMO Pathway: Emerging Mechanisms That Shape Specificity, Conjugation and Recognition," Nature Reviews. Molecular Cell Biology 11, pp. 861-871, Nature Pub. Group, England (Dec. 2010).

Garon, E.B., et al., "Ramucirumab Plus Docetaxel Versus Placebo Plus Docetaxel for Second-line Treatment of Stage Iv Non-small-cell Lung Cancer After Disease Progression on Platinum-based Therapy (Revel): a Multicentre, Double-blind, Randomised Phase 3 Trial," Lancet 384(9944), pp. 665-673, Elsevier, England (2014).

Genbank, "programmed cell death 1 ligand 1 isoform a precursor [Homo sapiens]," Accession No. NP_054862.1, accessed at https://www.ncbi.nlm.nih.gov/protein/NP_054862.

GenBank Accession No. AAL07473.1, accessed at https://www.ncbi.nlm.nih.gov/protein/AAL07473.

GenBank Accession No. AF414120.1, accessed at https://www.ncbi.nlm.nih.gov/nuccore/AF414120.1 .

Gill, G., "SUMO and Ubiquitin in the Nucleus: Different Functions, Similar Mechanisms?," Genes & Development 18(17), pp. 2046-2059, Cold Spring Harbor, United States (Sep. 2004).

Goodson, M. L., et al., "Sumo-1 Modification Regulates the DNA Binding Activity of Heat Shock Transcription Factor 2, a Promyelocytic Leukemia Nuclear Body Associated Transcription Factor," The Journal of Biological Chemistry 276(21), pp. 18513-18518, Elsevier, United States (May 2001).

Grosso, J.F. and Jure-Kunkel, M.N., "CTLA-4 Blockade in Tumor Models: An Overview of Preclinical and Translational Research," Cancer Immunity 13:5, Cancer Research Institute, United States (2013).

Guram, K., et al., "A Threshold Model for T-Cell Activation in the Era of Checkpoint Blockade Immunotherapy," Frontiers in Immunology, vol. 10, Article 491, 20 pages, entire document (Mar. 2019).

Hatton, B.A., et al., abstract #4136 "Direct Intratumoral Microdosing via the CIVO® Platform Reveals Anti-tumor Immune Responses Induced by the SUMO Inhibitor TAK-981," Immunology: Novel Immunomodulatory Agents 2 60:1065, AACR Annual Meeting, United States (Mar. 2019), 1 page.

Hay, R.T., SUMO-specific Proteases: a Twist in the Tail, Trends in Cell Biology 17(8), pp. 370-376, Elsevier Science Publishers, England (Aug. 2007).

Hay, R.T., "SUMO: a History of Modification," Molecular Cell 18(1), pp. 1-12, Cell Press, United States (2005).

He, X., et al., "Probing the Roles of SUMOylation in Cancer Cell Biology by Using a Selective SAE Inhibitor," Nature Chemical Biology 13, pp. 1164-1171, Nature Pub. Group, United States (Nov. 2017).

Hoellein, A, et al., "Myc-induced SUMOylation Is a Therapeutic Vulnerability for B-cell Lymphoma," Blood 124(13), pp. 2081-2090, Elsevier, United States (2014).

International Search Report and Written Opinion for Application No. PCT/US2020/020171, mailed on Jul. 15, 2020, 11 pages.

Johnson, E. S., and Gupta, A. A, "An E3-like Factor That Promotes Sumo Conjugation to the Yeast Septins," Cell 106(6), pp. 735-744, Cell Press, United States (Sep. 2001).

Kagey, M. H., et al., "The Polycomb Protein Pc2 Is a SUMO E3," Cell 113(1), pp. 127-137, Cell Press, United States (Apr. 2003).

Kamitani, T., et al., "Characterization of a Second Member of the Sentrin Family of Ubiquitin-like Proteins," The Journal of Biological Chemistry 273(18), pp. 11349-11353, Elsevier, United States (1998).

Kerscher, O., et al., "Modification of Proteins by Ubiquitin and Ubiquitin-like Proteins," Annual Review of Cell and Developmental Biology 22, pp. 159-180, Annual Reviews, United States (2006).

Kessler, J. D., et al., "A SUMOylation-dependent Transcriptional Subprogram Is Required for Myc-driven Tumorigenesis," Science

(56) References Cited

OTHER PUBLICATIONS

335(6066), pp. 348-353, American Association for the Advancement of Science, United States (Jan. 2012).
Khattar, M., et al., abstract #3252 "TAK-981: A First in Class Sumo Inhibitor in Phase 1 Trials That Promotes Dendritic Cell Activation, Antigen-presentation and T Cell Priming," IMMUNOLOGY: Novel Immunomodulatory Agents 1 60:837, AACR Annual Meeting, United States (Mar. 2019), 1 page.
Le, D.T., et al., "KEYNOTE-164: Pembrolizumab for patients with advanced microsatellite instability high (MSI-H) colorectal cancer," Journal of Clinical Oncology 36(15 Supplement) 3514 (2018).
Le, D.T., et al., "PD-1 Blockade in Tumors with Mismatch-Repair Deficiency," The New England Journal of Medicine 372(26):2509-2520, Massachusetts Medical Society, United States (Jun. 2015).
Lee, H. R., et al., "Ability of the Human Cytomegalovirus 1e1 Protein to Modulate Sumoylation of Pml Correlates With Its Functional Activities in Transcriptional Regulation and Infectivity in Cultured Fibroblast Cells," Journal of Virology 78(12), pp. 6527-6542, American Society For Microbiology, United States (Jun. 2004).
Liu, B., and Shuai, K., "Summon SUMO to Wrestle With Inflammation," Molecular Cell 35(6), pp. 731-732, Cell Press, United States (Sep. 2009).
Long, H.J., et al., "Randomized Phase III Trial of Cisplatin With or Without Topotecan in Carcinoma of the Uterine Cervix: a Gynecologic Oncology Group Study," Journal of Clinical Oncology 23(21), pp. 4626-4633, American Society of Clinical Oncology, United States (2005).
Mahajan, R., et al., "A Small Ubiquitin-related Polypeptide Involved in Targeting Rangap1 to Nuclear Pore Complex Protein Ranbp2," Cell 88(1), pp. 97-1070, Cell Press, United States (Jan. 1997).
Mayer, R.J., et al., "Randomized Trial of TAS-102 for Refractory Metastatic Colorectal Cancer," The New England Journal of Medicine 372(20), pp. 1909-1919, Massachusetts Medical Society, United States (2015).
Monk, B.J., et al., "Phase III Trial of Four Cisplatin-containing Doublet Combinations in Stage lvb, Recurrent, or Persistent Cervical Carcinoma: a Gynecologic Oncology Group Study," Journal of Clinical Oncology 27(28), pp. 4649-4655, American Society of Clinical Oncology, United States (2009).
Moore, D.H., et al., "Phase III Study of Cisplatin With or Without Paclitaxel in Stage lvb, Recurrent, or Persistent Squamous Cell Carcinoma of the Cervix: a Gynecologic Oncology Group Study," Journal of Clinical Oncology 22(15), pp. 3113-3119, American Society of Clinical Oncology, United States (2004).
Moschos, S. J., et al., "Expression Analysis of Ubc9, the Single Small Ubiquitin-like Modifier (SUMO) E2 Conjugating Enzyme, in Normal and Malignant Tissues," Human Pathology 41(9), pp. 1286-1980, W B Saunders, United States (Sep. 2010).
Muller S., et al., "SUMO, Ubiquitin's Mysterious Cousin," Nature Reviews. Molecular Cell Biology 2(3), pp. 202-210, Nature Pub. Group, England (Mar. 2001).
Nakamura, A., et al., abstract #1523 "Inhibition of SUMOylation by TAK-981 Induces Antitumor Innate Immune Responses by Modulating Macrophage and NK cell Function Through Type I IFN Pathway Activation," IMMUNOLOGY: Suppressive Myeloid Cells 60:390, AACR Annual Meeting, United States (Mar. 2019), 1 page.
Nielsen, C., et al., "Alternative Splice Variants of the Human Pd-1 Gene," Cellular Immunology 235, pp. 109-116, Elsevier, Netherlands (Jun. 2005).
Oliveira A.F., et al., "Review of PD-1/PD-L1 Inhibitors in Metastatic dMMR/MSI-H Colorectal Cancer," Frontiers in Oncology 9, pp. 396, Frontiers Research Foundation, Switzerland (May 2019).
O'Neil, B.H., et al., "Safety and Antitumor Activity of the Anti-pd-1 Antibody Pembrolizumab in Patients With Advanced Colorectal Carcinoma," PLoS One 12(12): e0189848, Public Library of Science, United States (2017).

Overman, M. J., et al., "Nivolumab in Patients with Metastatic DNA Mismatch Repair-Deficient or Microsatellite Instability-High Colorectal Cancer (CheckMate 142): An Open-Label, Multicentre, Phase 2 Study," The Lancet Oncology 18(9):1182-1191, Lancet Publishing Group, United Kingdom (Sep. 2017).
Overman, M.J., et al., "Durable Clinical Benefit With Nivolumab Plus Ipilimumab in DNA Mismatch Repair-Deficient/Microsatellite Instability-High Metastatic Colorectal Cancer," Journal of Clinical Oncology 36(8), pp. 773-779, American Society of Clinical Oncology, United States (2018).
Pichler, A., et al., "The Nucleoporin RanBP2 Has SUMO1E3 Ligase Activity," Cell 108(1), pp. 109-120, Cell Press, United States (Jan. 2002).
Rodriguez, M. S., et al., "SUMO-1 Modification Activates the Transcriptional Response of P53,"The EMBO Journal 18(22), pp. 6455-6461, Wiley Blackwell, England (Nov. 1999).
Sachdev, S., et al., "PIASy, a Nuclear Matrix-Associated SUMO E3 Ligase, Represses Lef1 Activity by Sequestration Into Nuclear Bodies," Genes & Development 15(23), pp. 3088-3103, Cold Spring Harbor Laboratory Press, United States (Dec. 2001).
Siegel, R., et al., "Cancer Statistics, 2014," CA: A Cancer Journal for Clinicians 64(1):9-29, Wiley, United States (Jan. 2014).
Siegel, R.L., et al., "Cancer Statistics, 2019," CA: a Cancer Journal for Clinicians 69(1), pp. 7-34, Wiley, United States (Jan. 2019).
Steffan, J. S., et al., "SUMO Modification of Huntingtin and Huntington's Disease Pathology," Science 304(5667), pp. 100-104, American Association for the Advancement of Science, United States (Apr. 2004).
Tatham, M. H., et al., "Polymeric Chains of SUMO-2 and SUMO-3 are Conjugated to Protein Substrates by SAE1/SAE2 and Ubc9," The Journal of Biological Chemistry 276(38), pp. 35368-35374, Elsevier, United States (Sep. 2001).
Van Cutsem, E., et al., "Addition of Aflibercept to Fluorouracil, Leucovorin, and Irinotecan Improves Survival in a Phase Iii Randomized Trial in Patients With Metastatic Colorectal Cancer Previously Treated With an Oxaliplatin-based Regimen," Journal of Clinical Oncology 30(28), pp. 3499-3506, American Society of Clinical Oncology, United States (Oct. 2012).
Wang, J., and Schwartz, R. J., "Sumoylation and Regulation of Cardiac Gene Expression," Circulation Research 107(1), pp. 19-29, Lippincott Williams & Wilkins, United States (Jul. 2010).
Wolfson, W., "Amber Codon Flashing Ambrx Augments Proteins With Unnatural Amino Acids," Chemistry & Biology 13(10), pp. 1011-1012, Elsevier, United States (Oct. 2006).
Yuan, Y., et al., "Bayesian Optimal Interval Design: A Simple and Well-Performing Design for Phase I Oncology Trials," Clinical Cancer Research 22(17):4291-4301, Denville, United States (Sep. 2016).
NCT03648372, "History of Changes for Study: NCT03648372—A Study to Evaluate the Safety, Tolerability and Pharmacokinetics (PK) of TAK-981 in Adult Participants With Metastatic Solid Tumors or Lymphomas" first submitted Aug. 24, 2018, sponsored by Millennium Pharmaceuticals, Inc., accessed at URL:[https://clinicaltrials.gov/ct2/history/NCT03648372?V_3=View#StudyPageTop], on Dec. 19, 2022, 6 pages.
Zappasodi, R., et al., "Emerging Concepts for Immune Checkpoint Blockade-Based Combination Therapies," Cancer Cell 33(4):581-598, Cell Press, United States (Apr. 2018).
Xu, C., et al., "Comparative safety of immune checkpoint inhibitors in cancer: systematic review and network meta-analysis," BMJ 363:k4226, pp. 1-28, BMJ Publishing Group, United Kingdom (Nov. 2018).
Melero, I., et al., "Evolving synergistic combinations of targeted immunotherapies to combat cancer," Nat Rev Cancer 15(8):457-472, Nature Publishing Group, United Kingdom (Aug. 2015).
Mashkovskiy, M.D.," Drugs: Manual for Doctors," vol. 1, pp. 11 New Wave Publishing House LLC, Moscow (2001).
English language translation of Office Action for Russian Patent Application No. 2021123498, dated Feb. 10, 2024, 3 pages.

\* cited by examiner

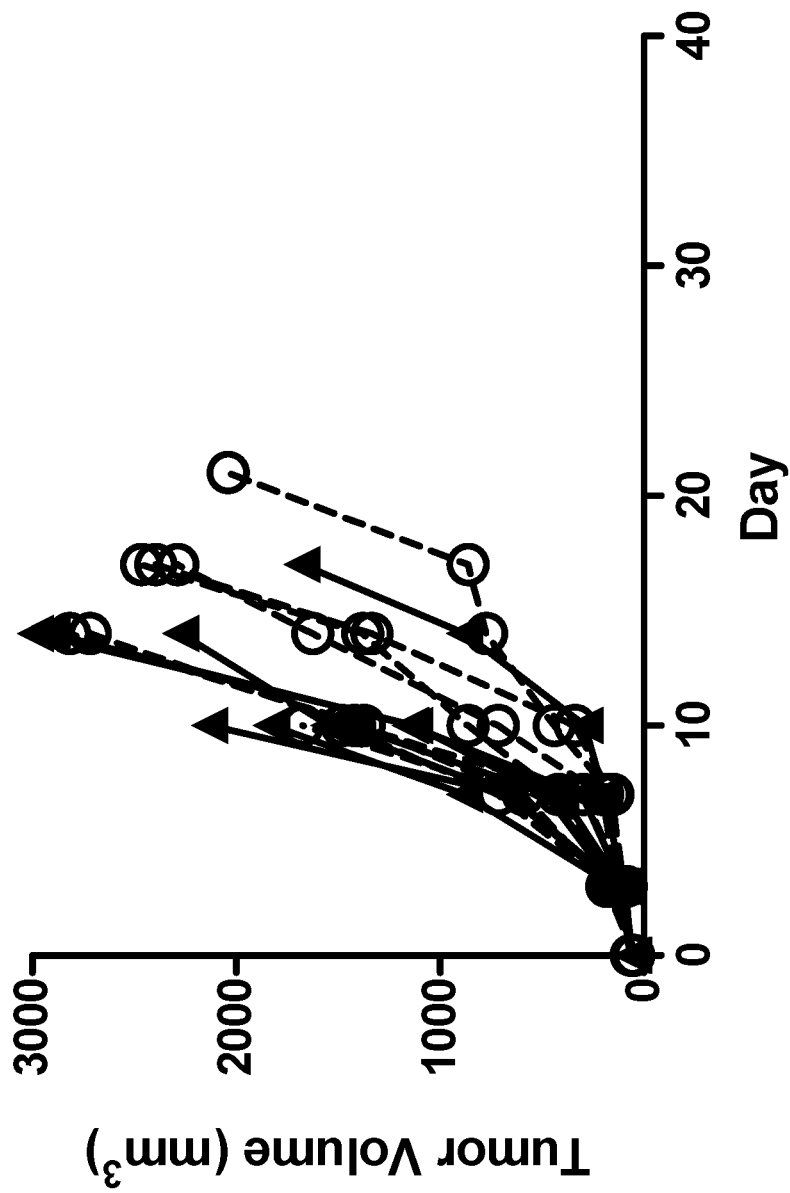
FIG. 1a: Anti-tumor activity of Compound I-263a and vehicle in mouse CT26 syngeneic tumor model

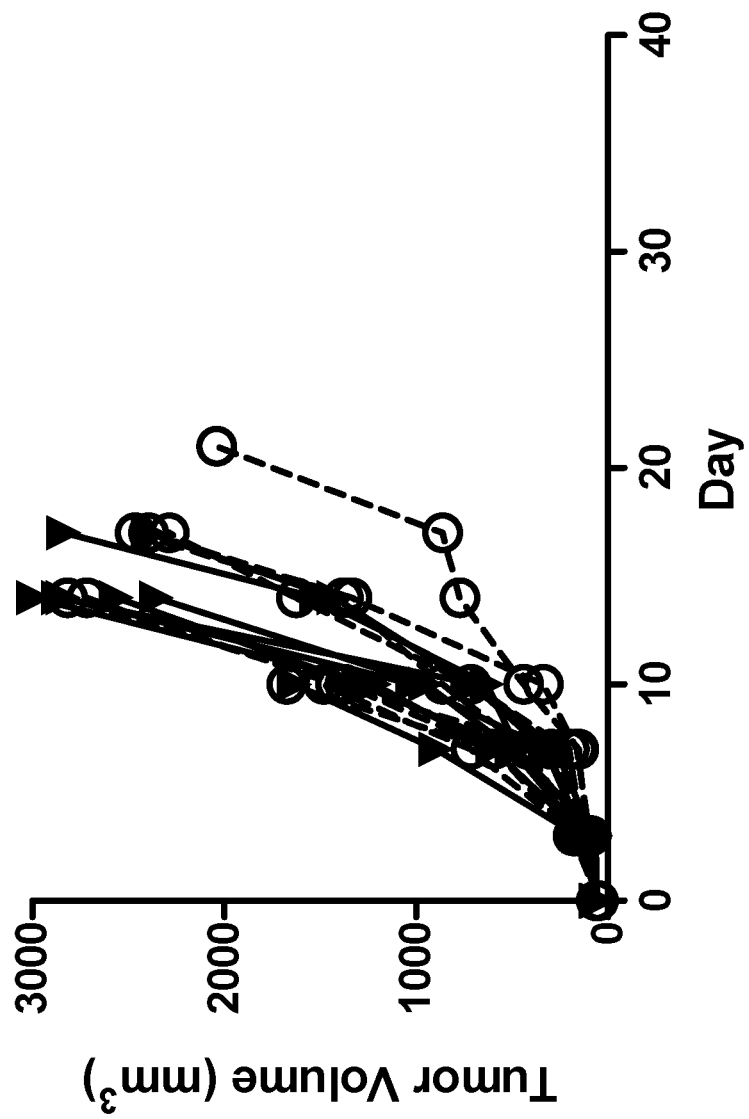
FIG. 1b: Anti-tumor activity of anti-mPD-1 and vehicle in mouse CT26 syngeneic tumor model

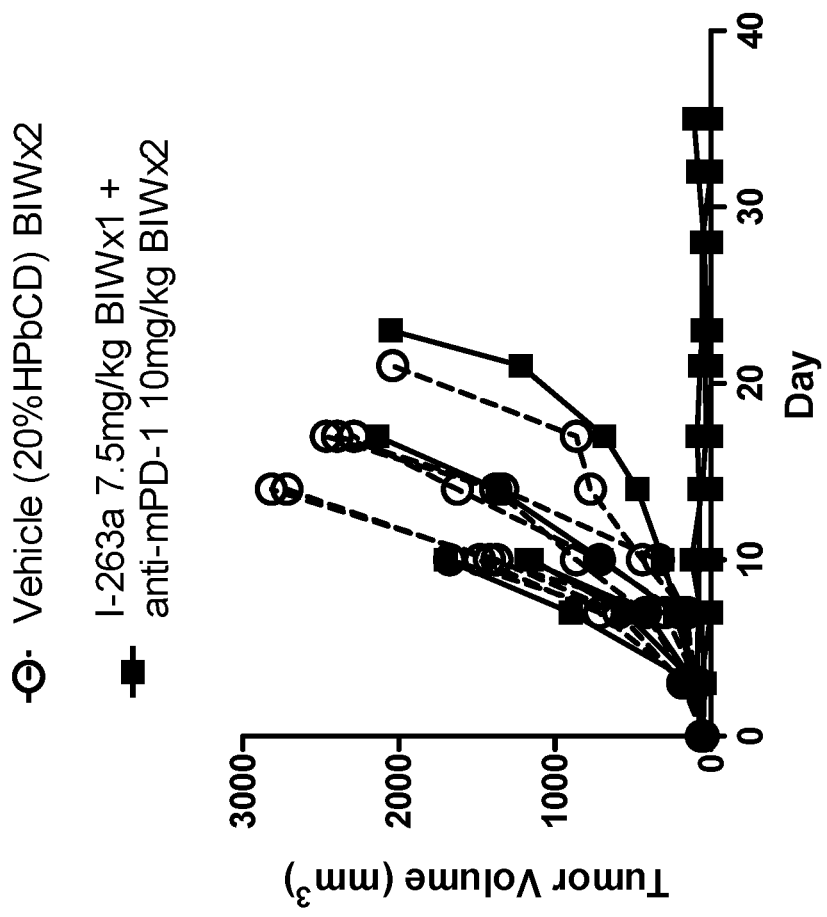
FIG. 1c: Anti-tumor activity of vehicle and combination of I-263a and anti-mPD-1 in mouse CT26 syngeneic tumor model

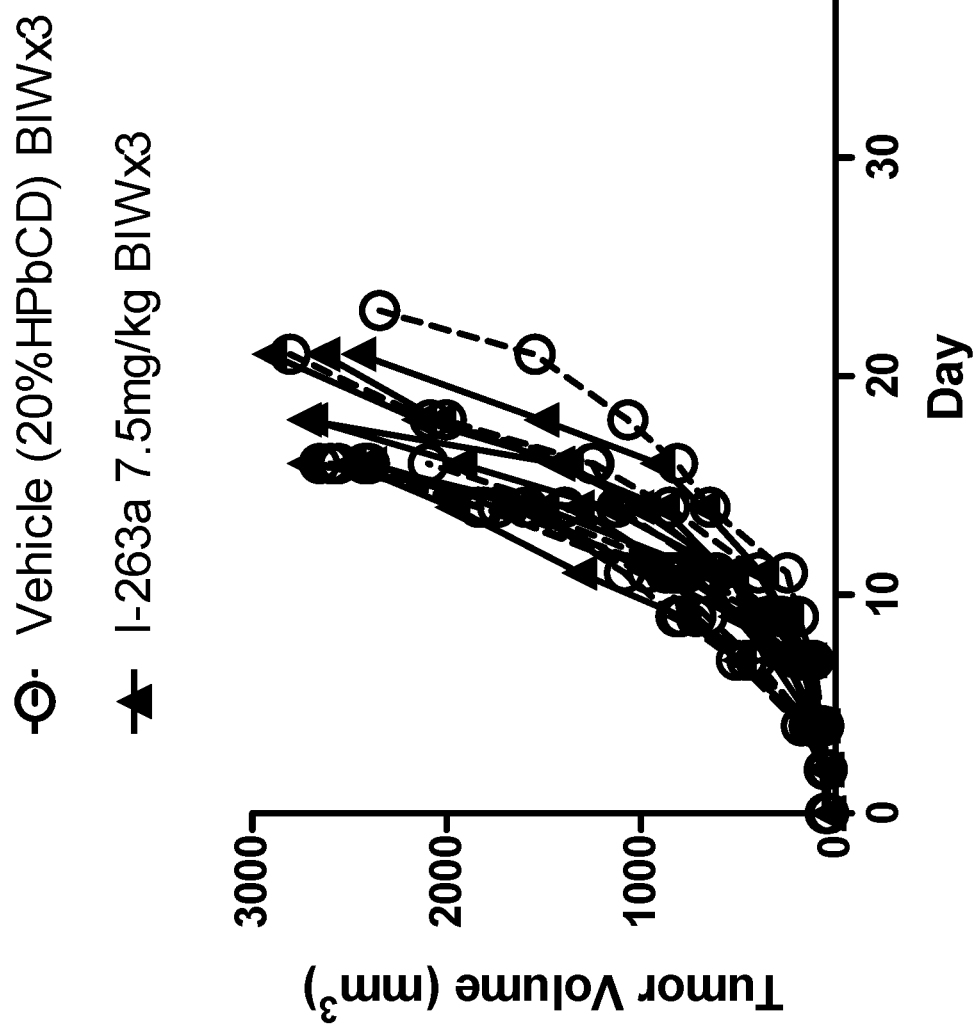
FIG. 2a: Anti-tumor activity of Compound I-263a and vehicle in mouse CT26 syngeneic tumor model

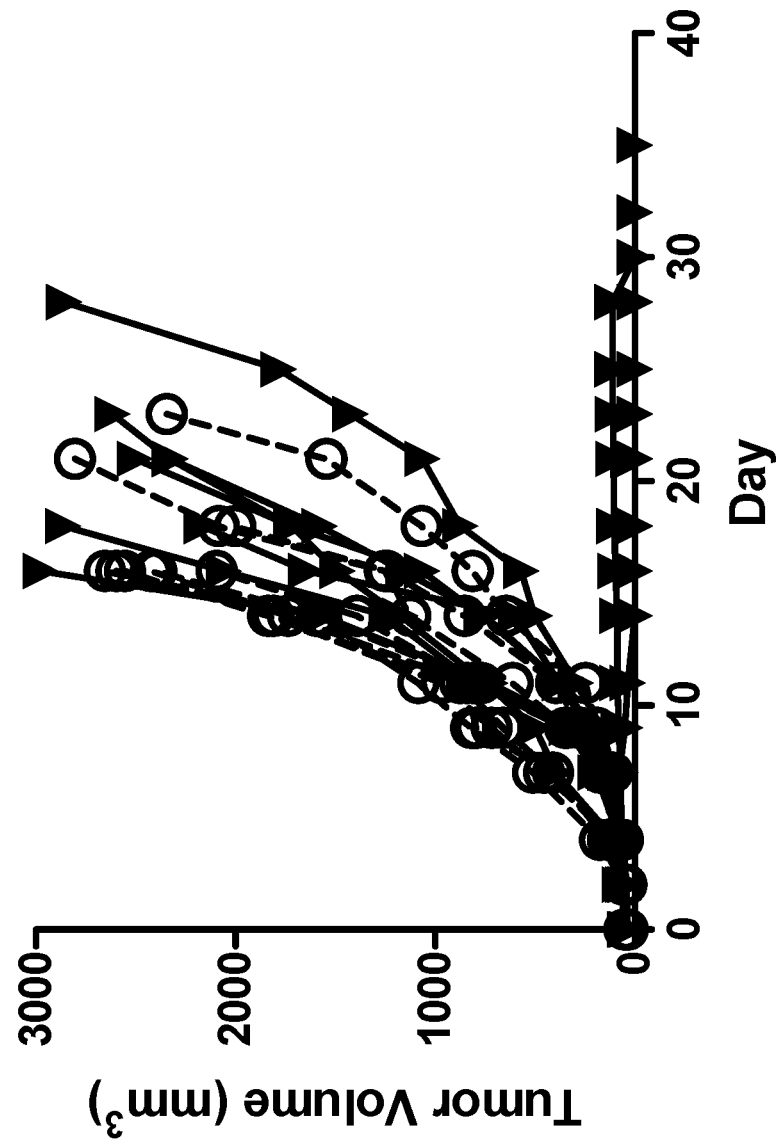
FIG. 2b: Anti-tumor activity of anti-mPD-1 and vehicle in mouse CT26 syngeneic tumor model

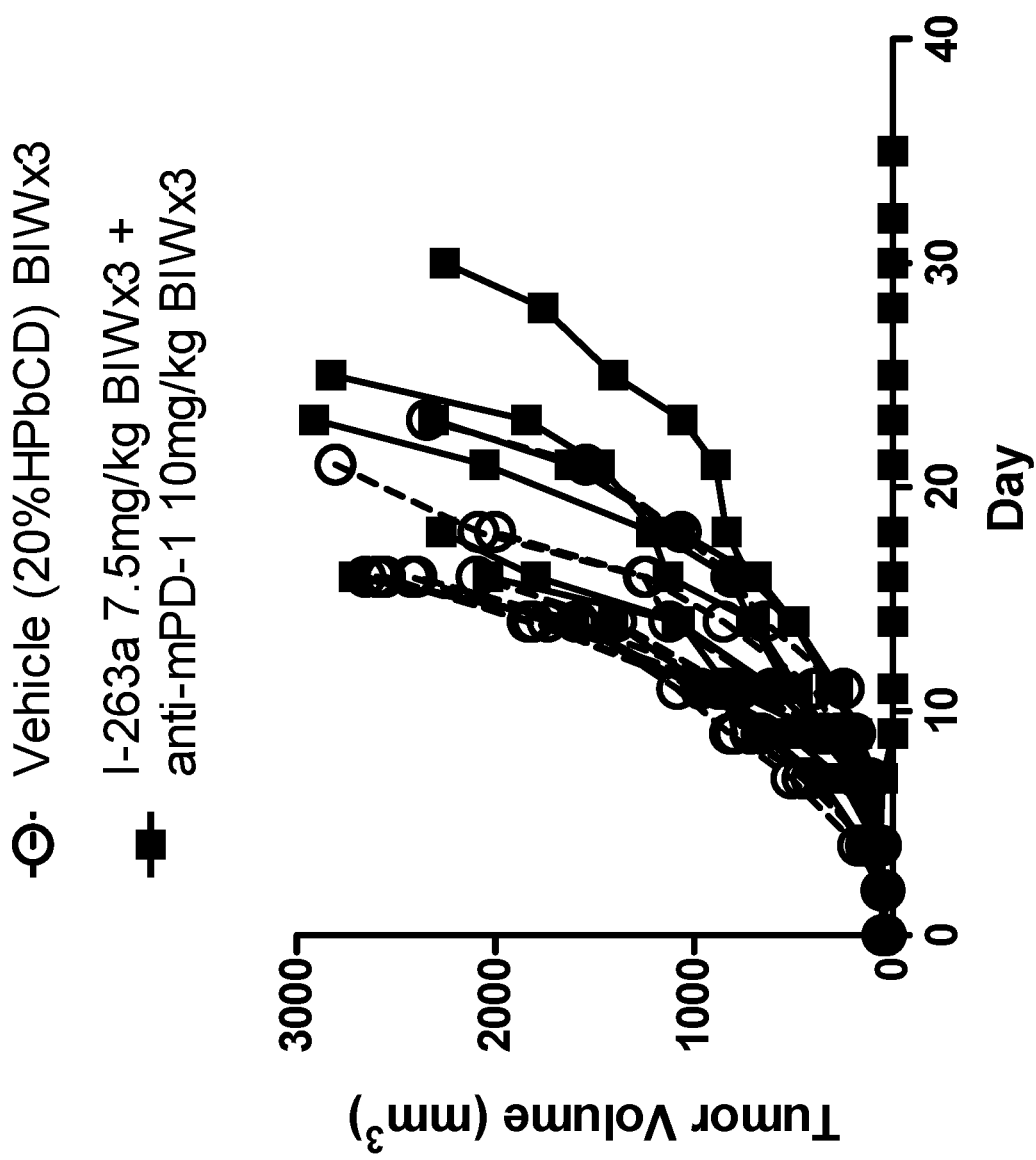
FIG. 2c: Anti-tumor activity of vehicle and combination of I-263a and anti-mPD-1 in mouse CT26 syngeneic tumor model

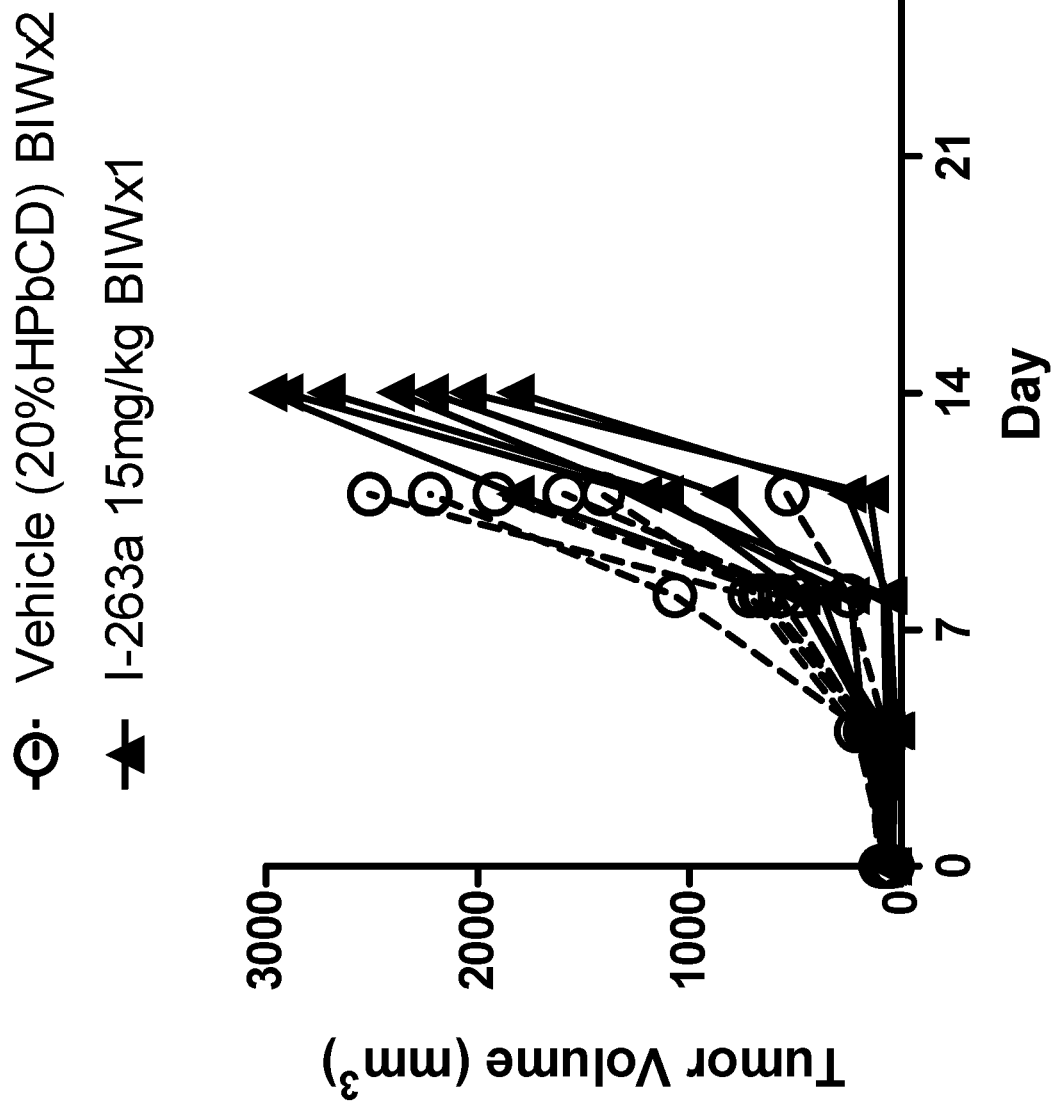
FIG. 3a: Anti-tumor activity of Compound I-263a and vehicle in mouse A20 syngeneic tumor model

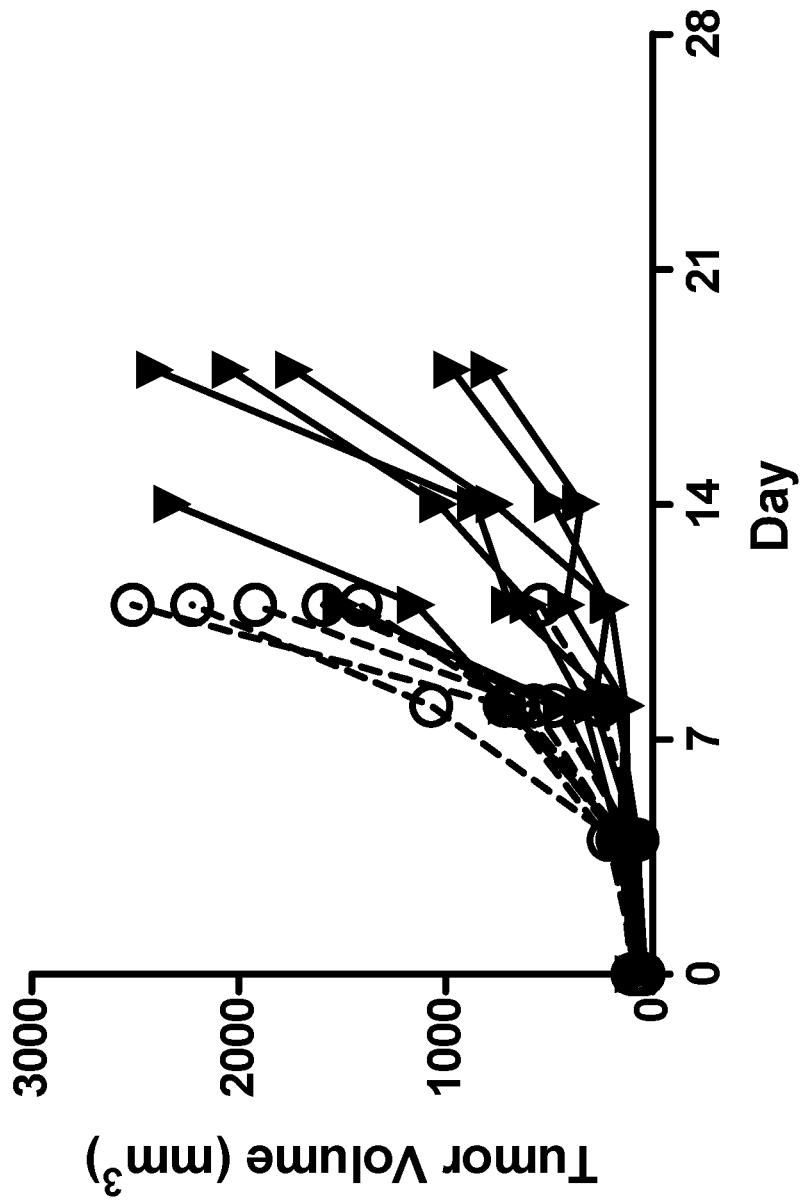
FIG. 3b: Anti-tumor activity of anti-mPD-1 and vehicle in mouse A20 syngeneic tumor model

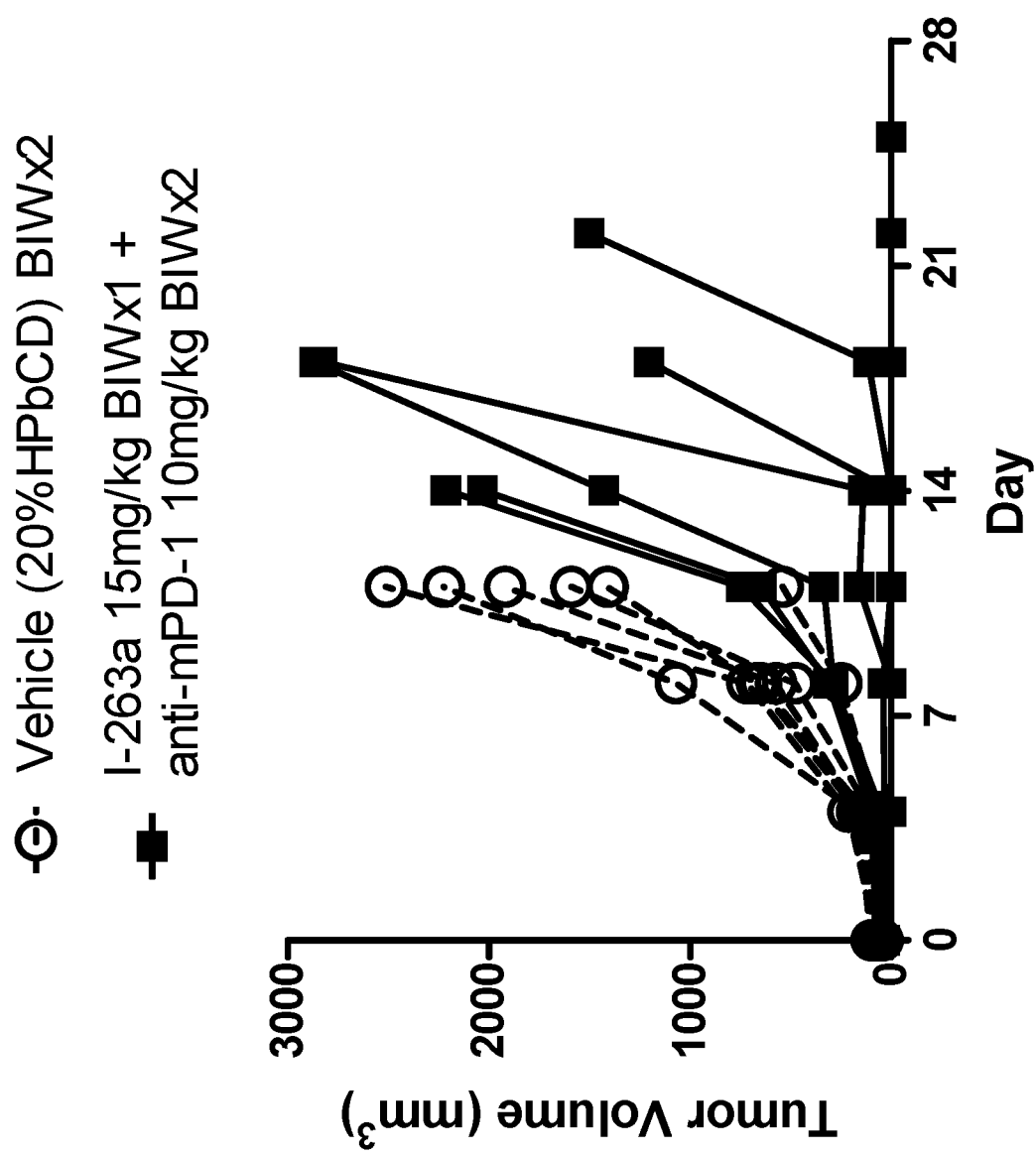
FIG. 3c: Anti-tumor activity of vehicle and combination of I-263a and anti-mPD-1 in mouse A20 syngeneic tumor model

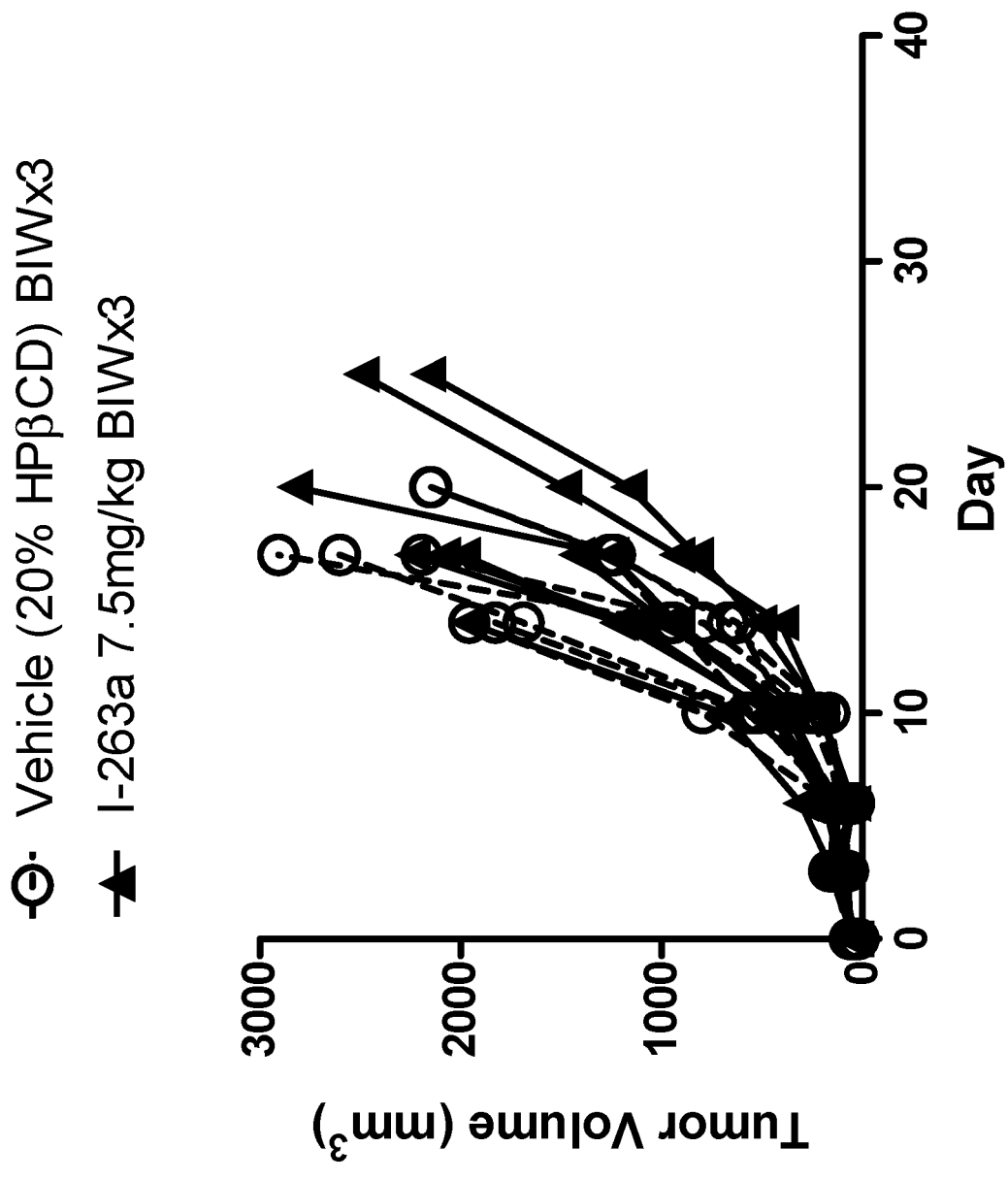
FIG. 4a: Anti-tumor activity of Compound I-263a and vehicle in mouse WEHI-3 syngeneic tumor model

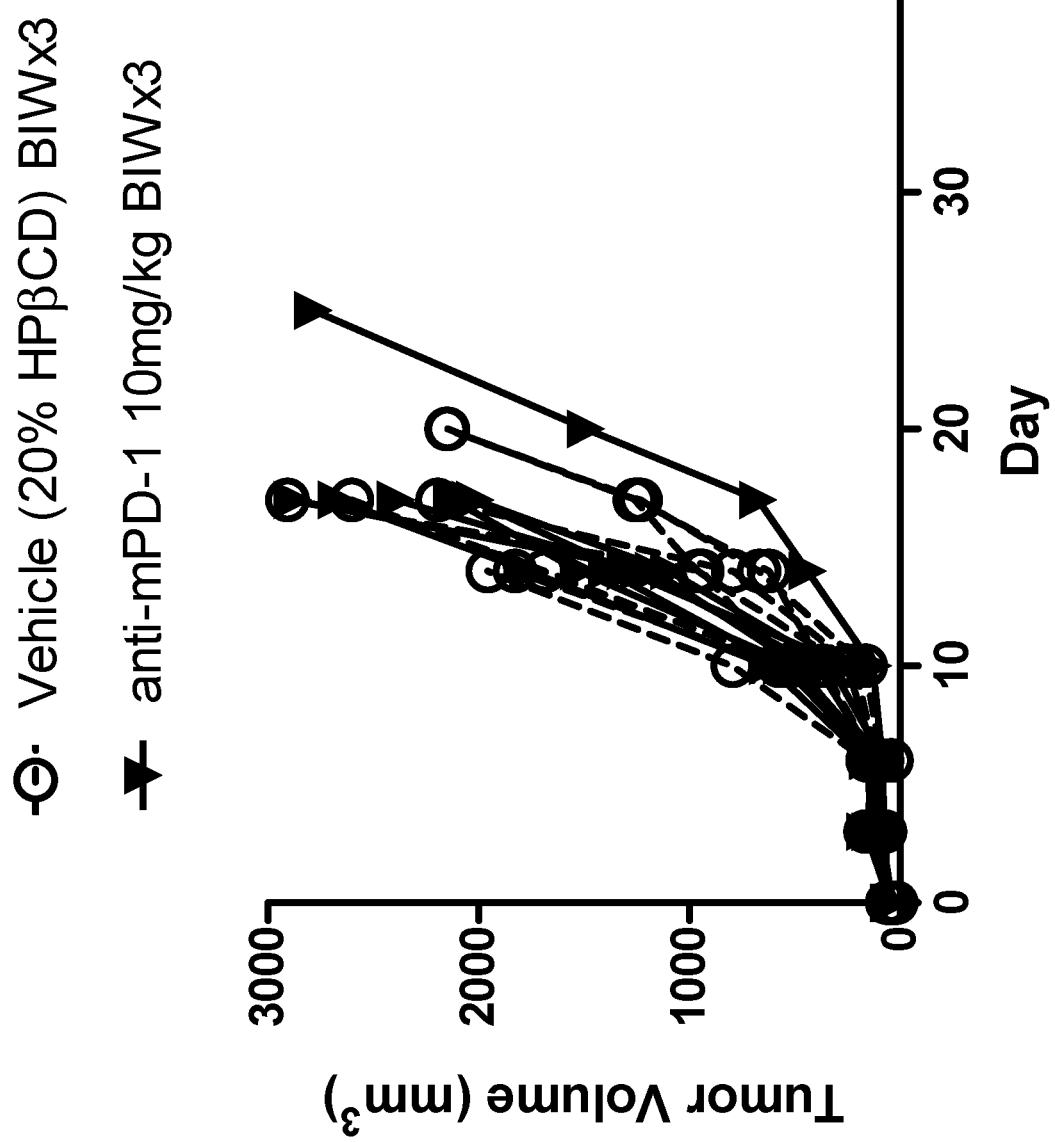
FIG. 4b: Anti-tumor activity of anti-mPD-1 and vehicle in mouse WEHI-3 syngeneic tumor model

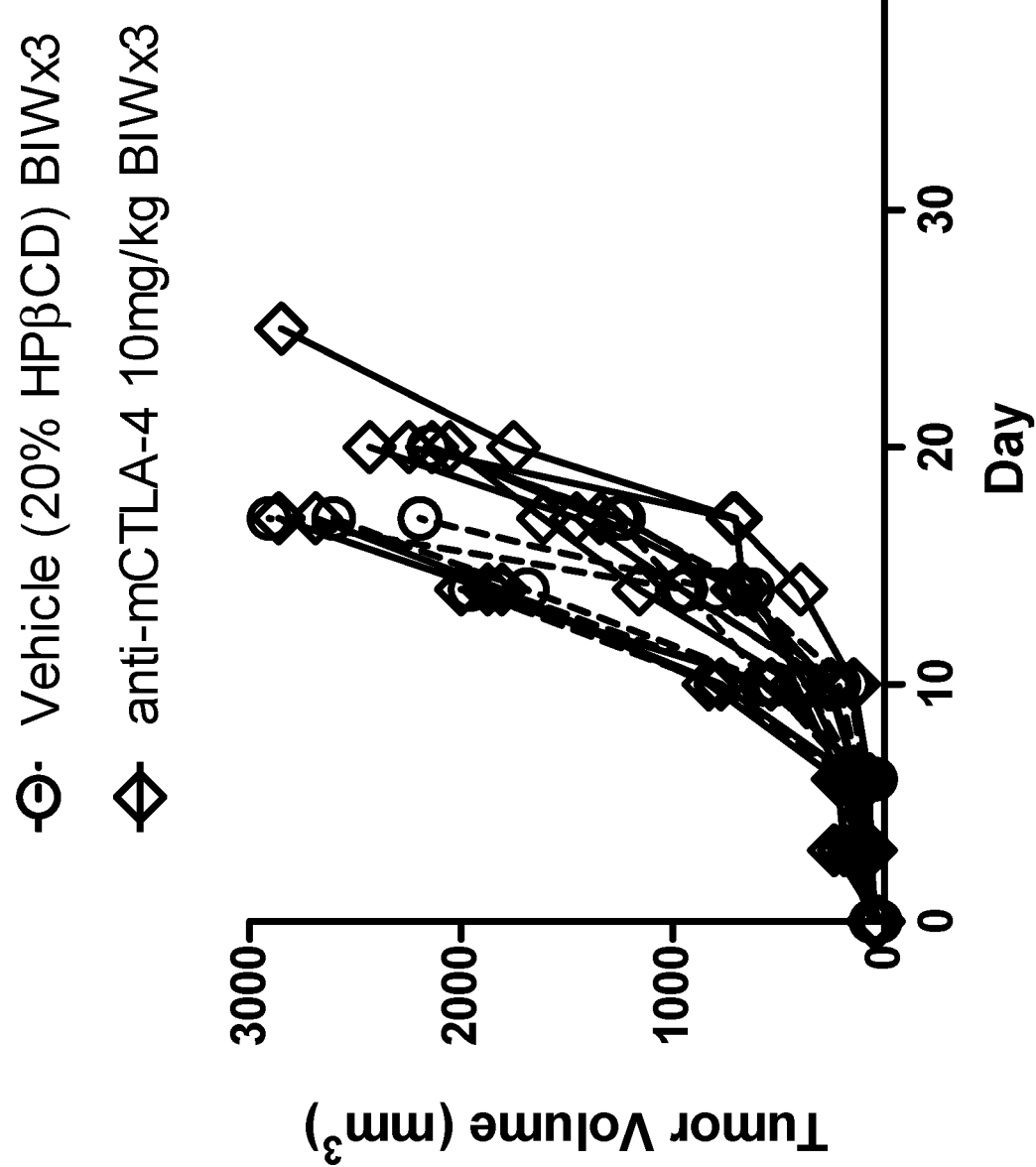
FIG. 4c: Anti-tumor activity of anti-mCTLA-4 and vehicle in mouse WEHI-3 syngeneic tumor model

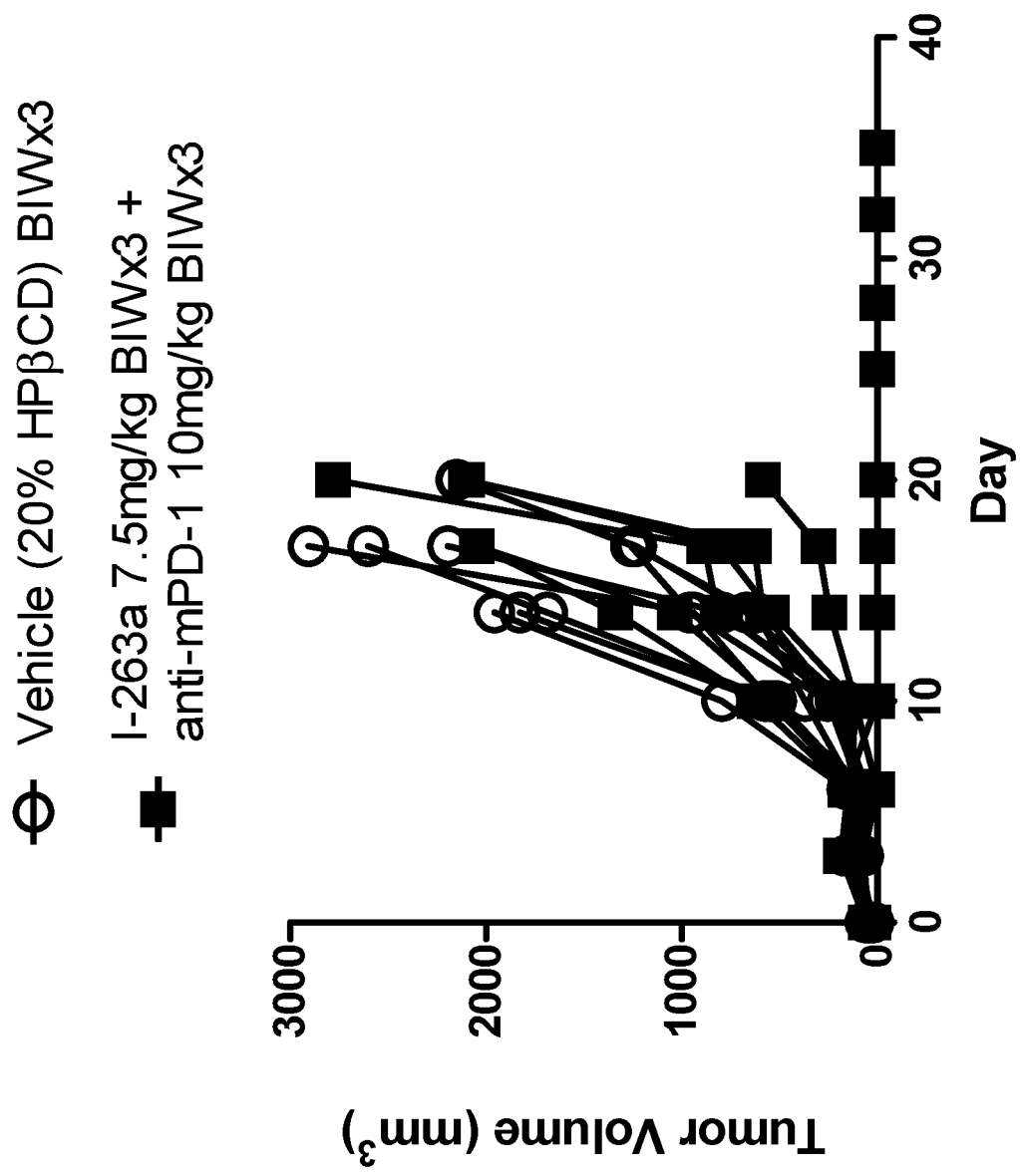
FIG. 4d: Anti-tumor activity of vehicle and combination of I-263a and anti-mPD-1 in mouse WEHI-3 syngeneic tumor model

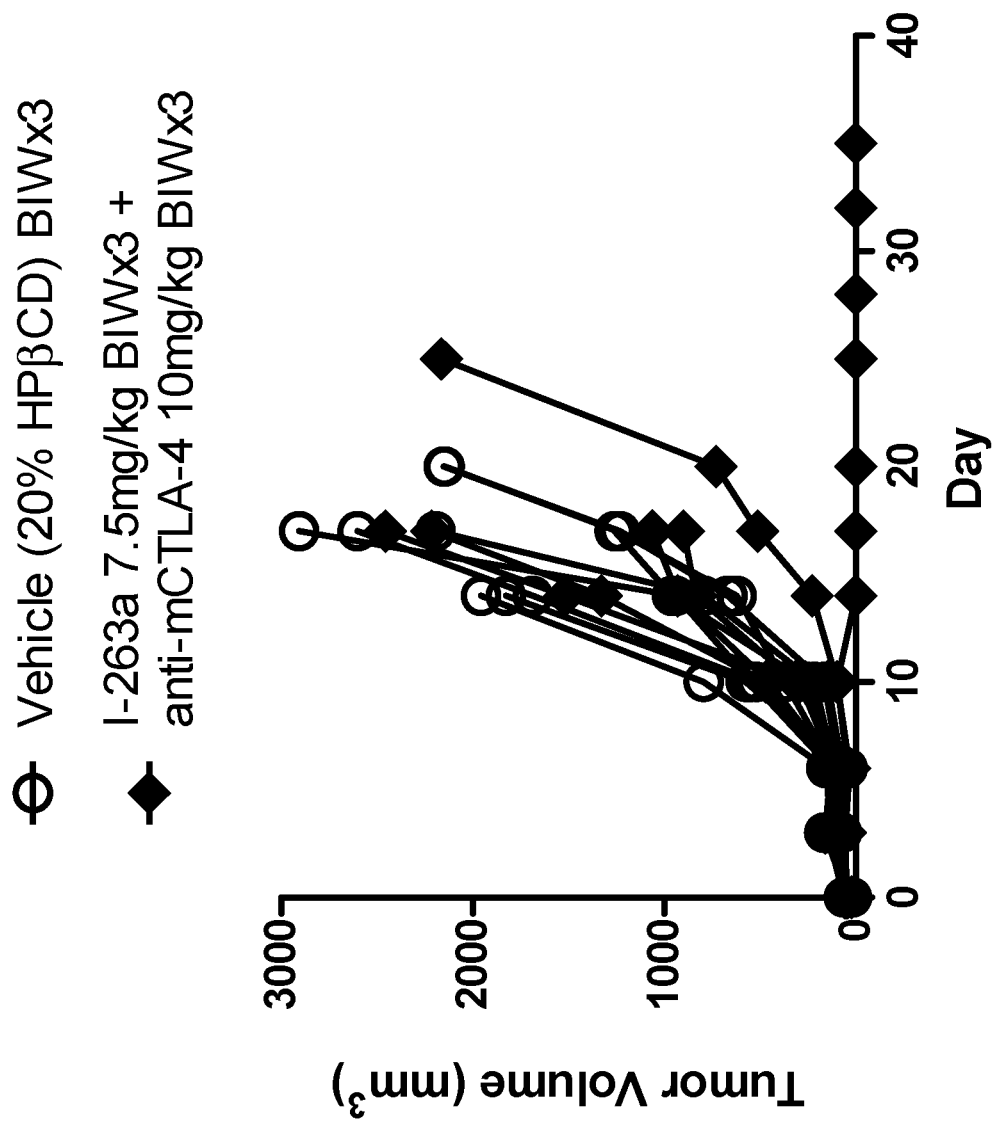
FIG. 4e: Anti-tumor activity of vehicle and combination of I-263a and anti-mCTLA-4 in mouse WEHI-3 syngeneic tumor model

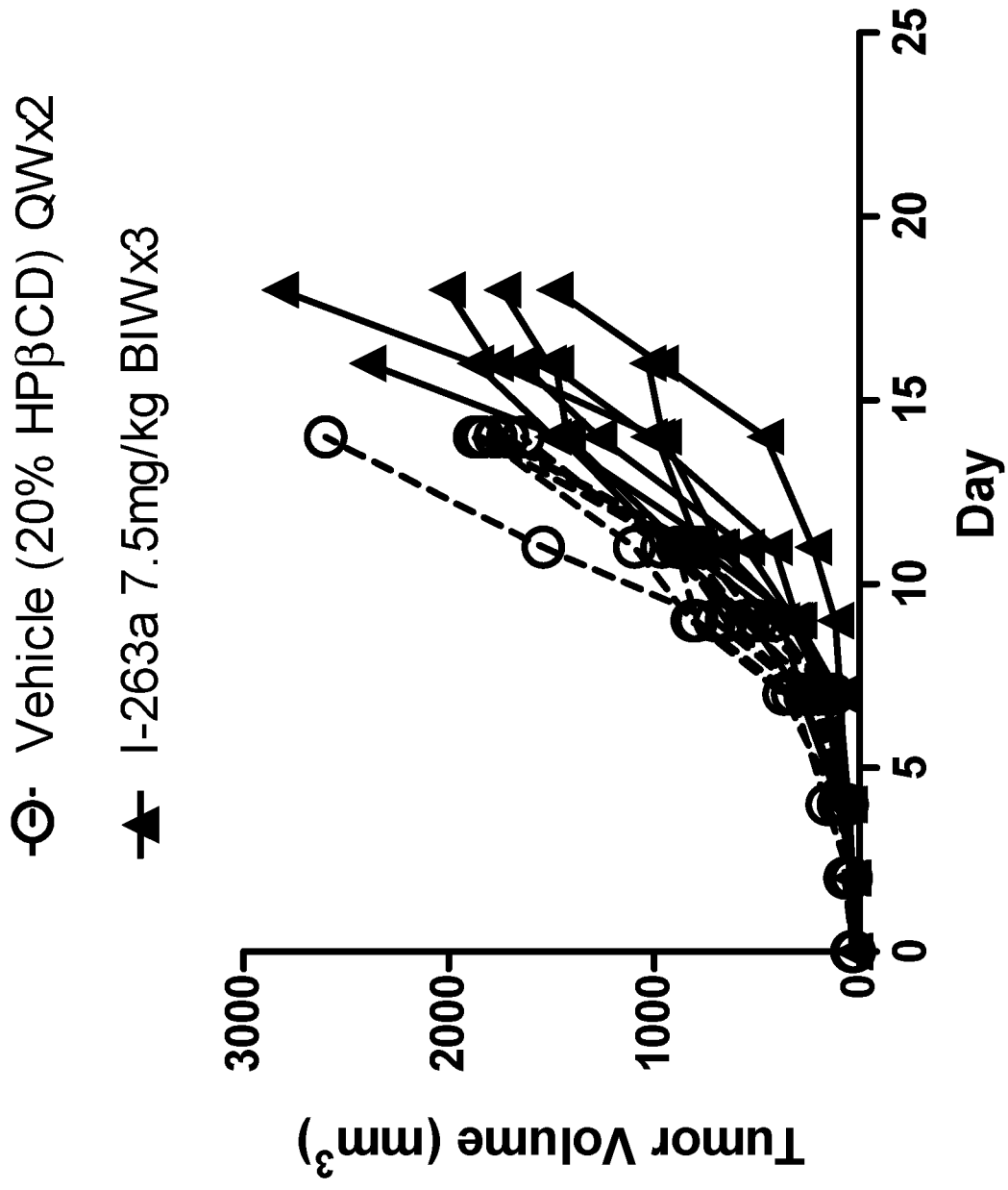
FIG. 5a: Anti-tumor activity of Compound I-263a and vehicle in mouse WEHI-3 syngeneic tumor model

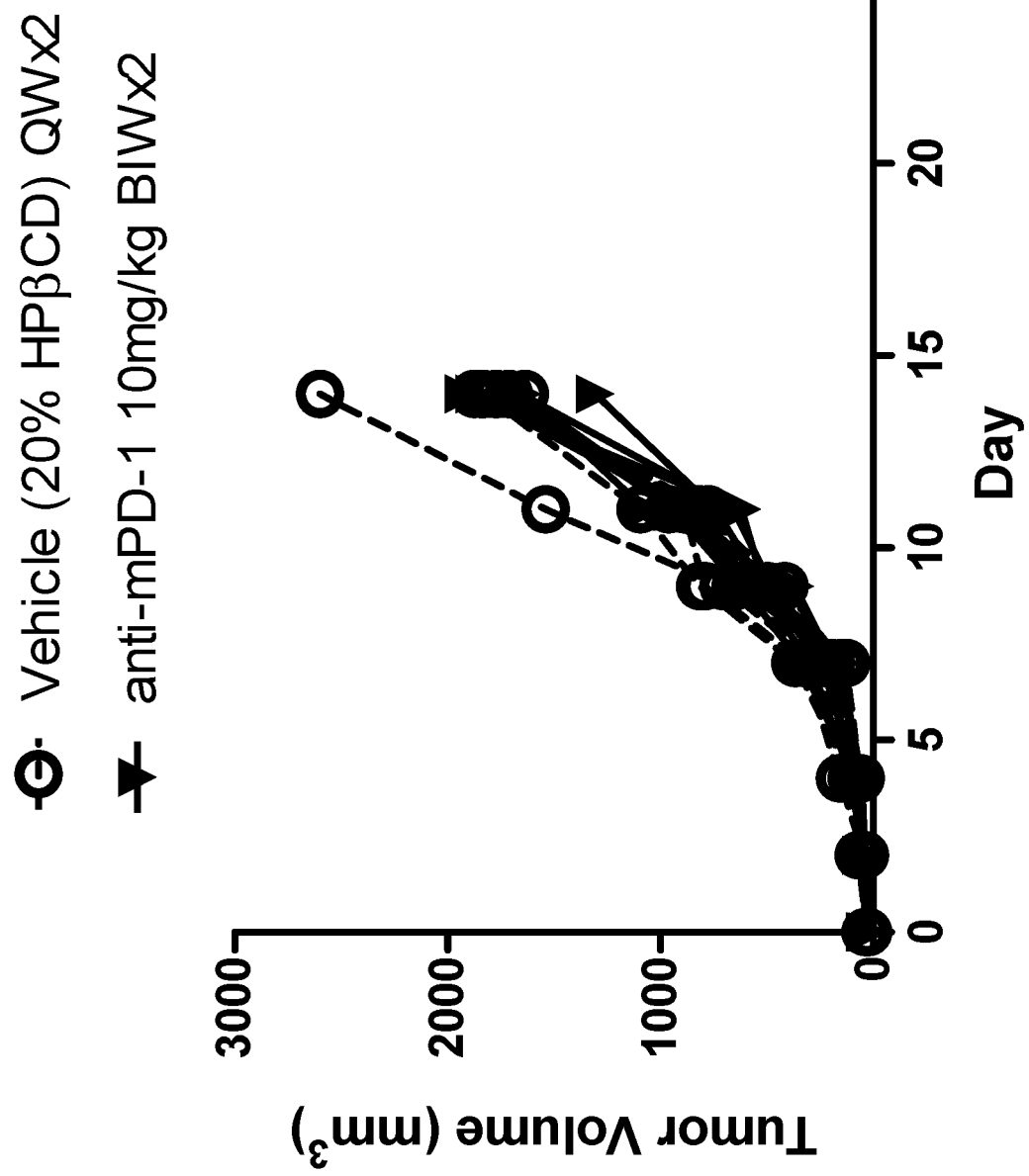
FIG. 5b: Anti-tumor activity of anti-mPD-1 and vehicle in mouse WEHI-3 syngeneic tumor model

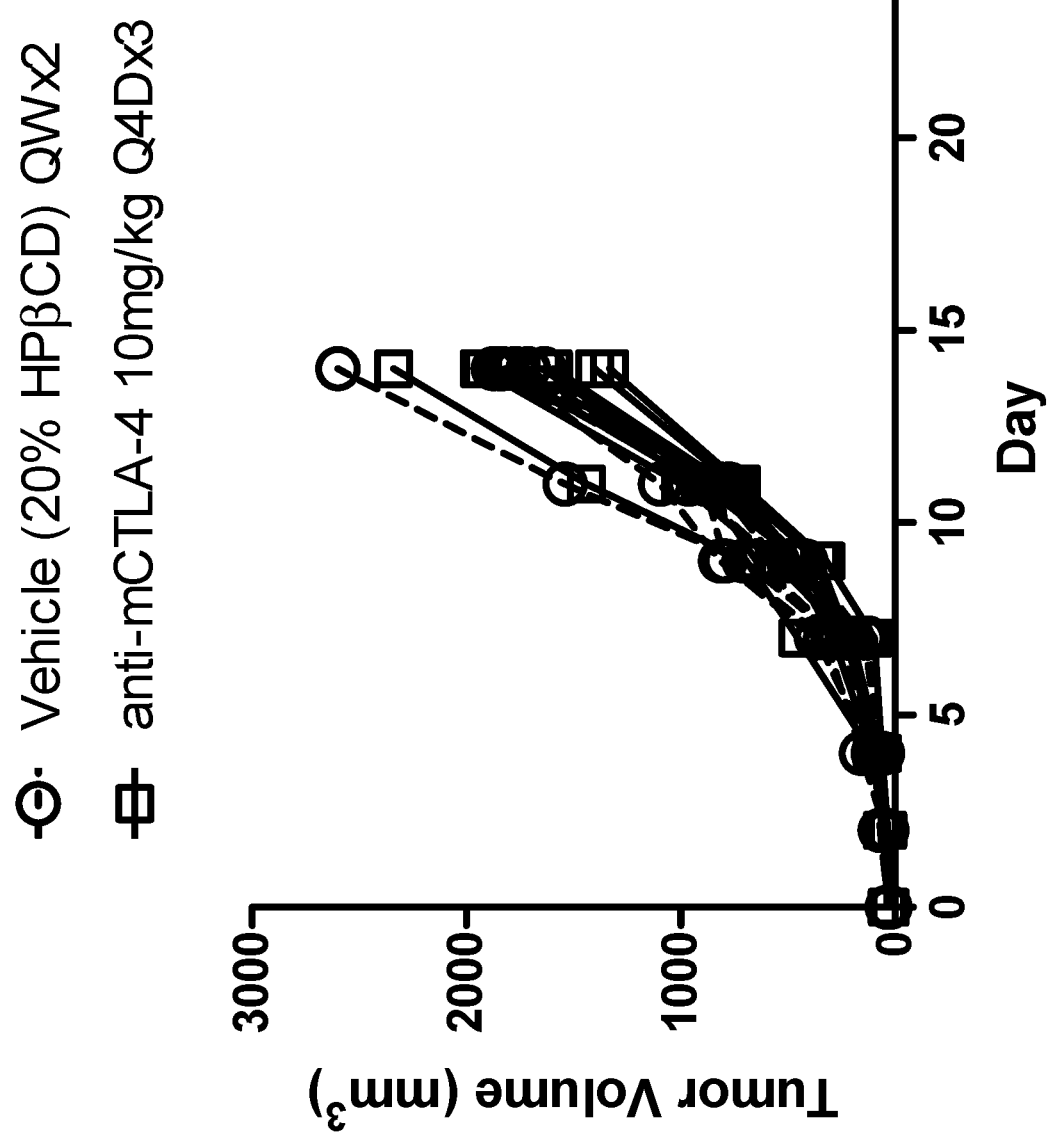
FIG. 5c: Anti-tumor activity of anti-mCTLA-4 and vehicle in mouse WEHI-3 syngeneic tumor model

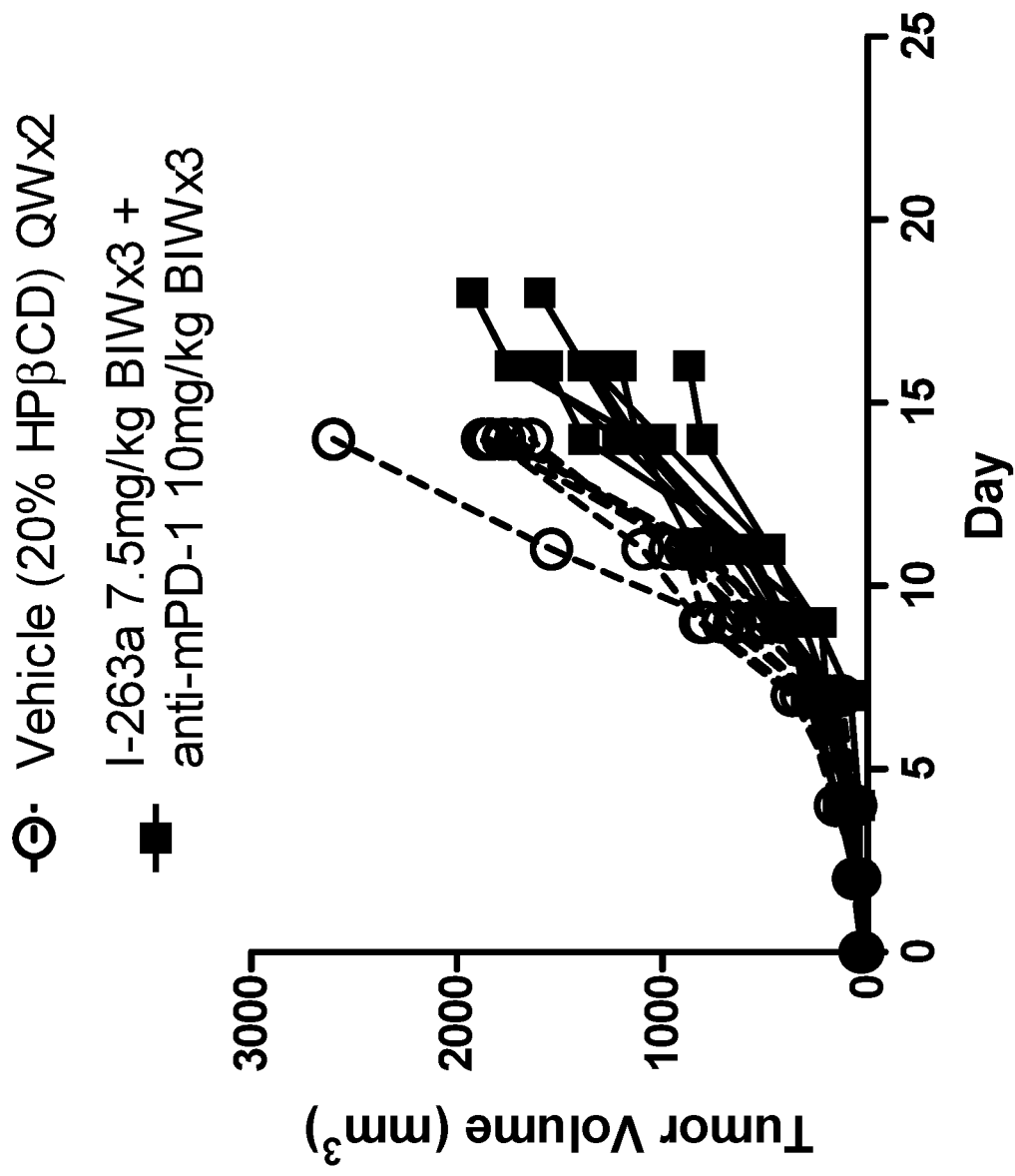
FIG. 5d: Anti-tumor activity of vehicle and combination of I-263a and anti-mPD-1 in mouse WEHI-3 syngeneic tumor model

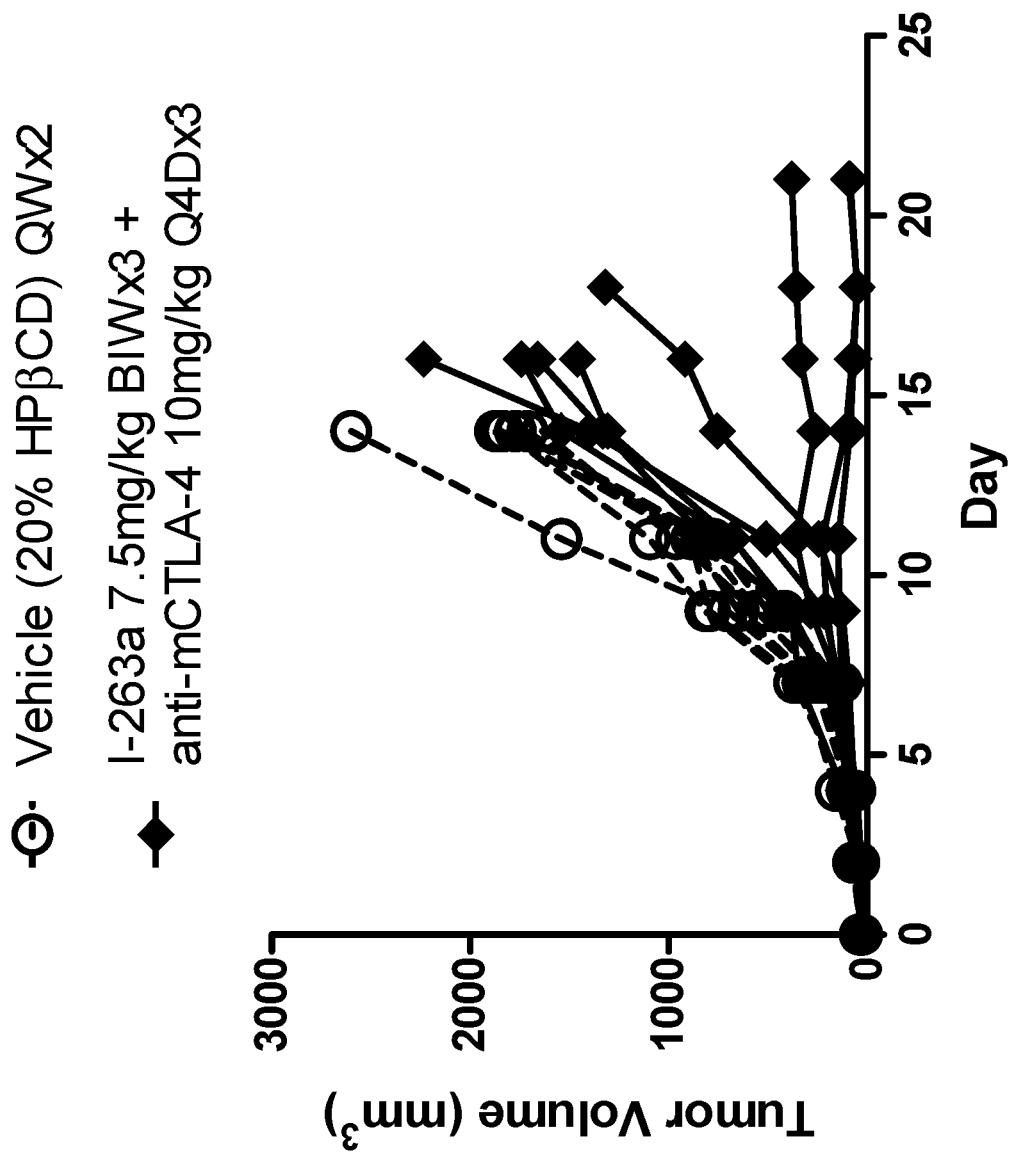
FIG. 5e: Anti-tumor activity of vehicle and combination of I-263a and anti-mCTLA-4 in mouse WEHI-3 syngeneic tumor model

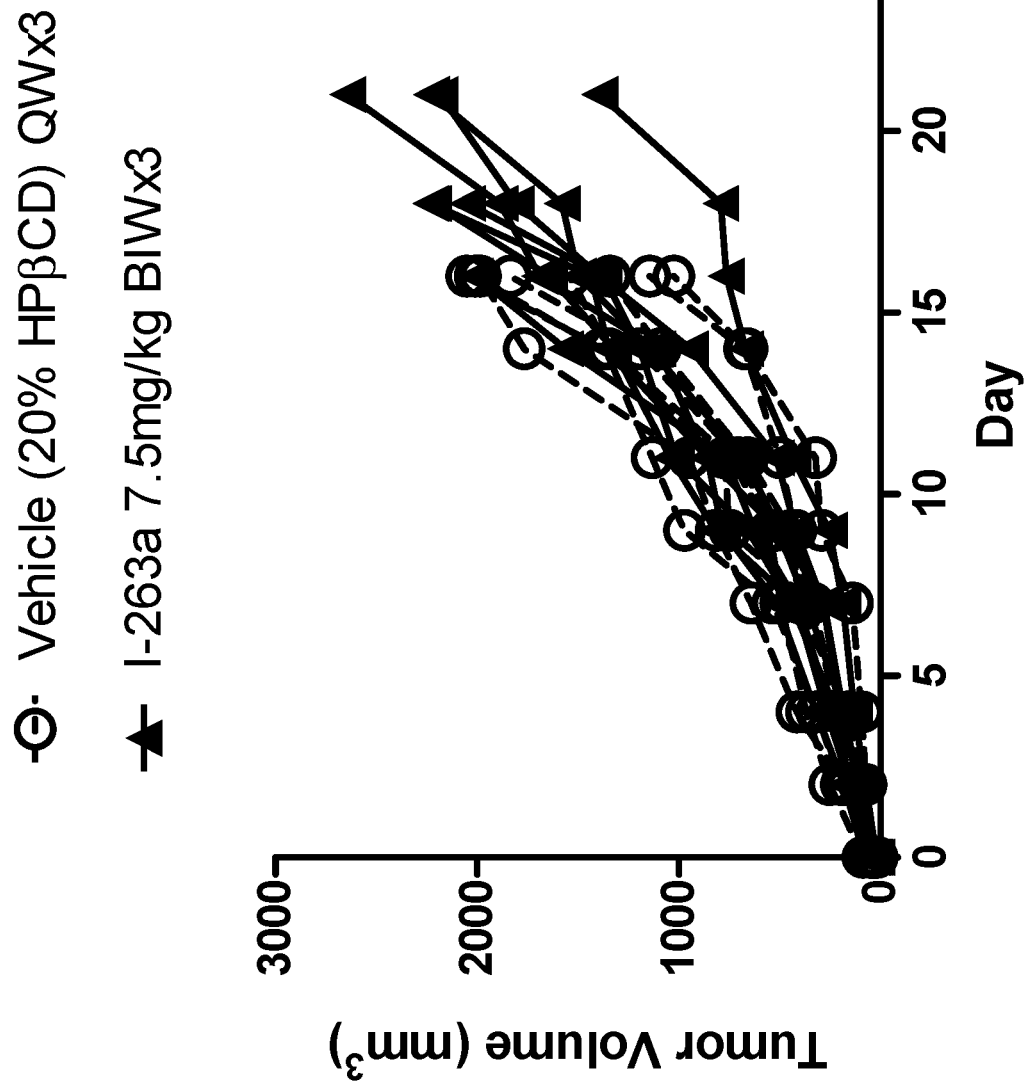
FIG. 6a: Anti-tumor activity of Compound I-263a and vehicle in mouse JC syngeneic tumor model

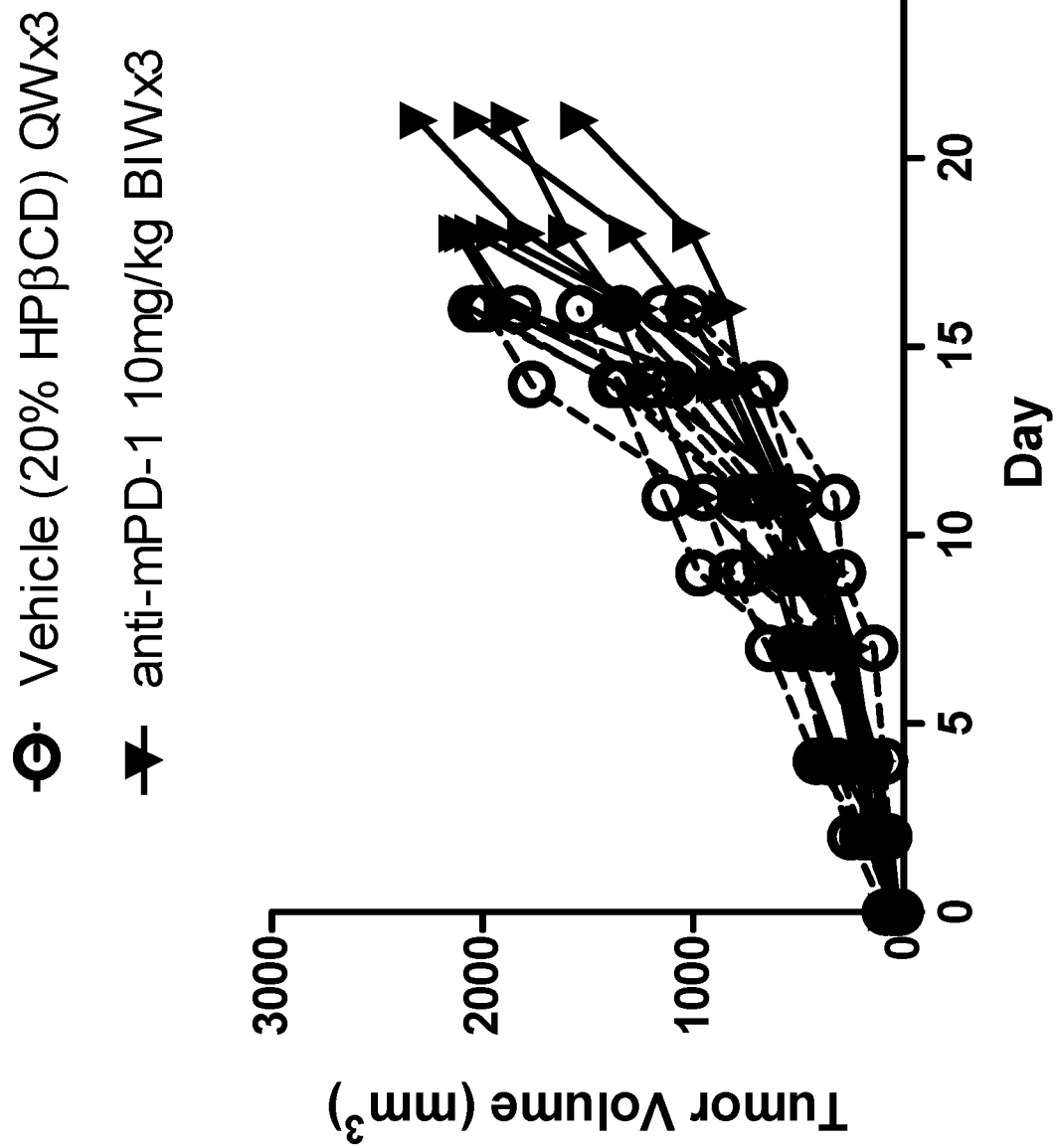
FIG. 6b: Anti-tumor activity of anti-mPD-1 and vehicle in mouse JC syngeneic tumor model

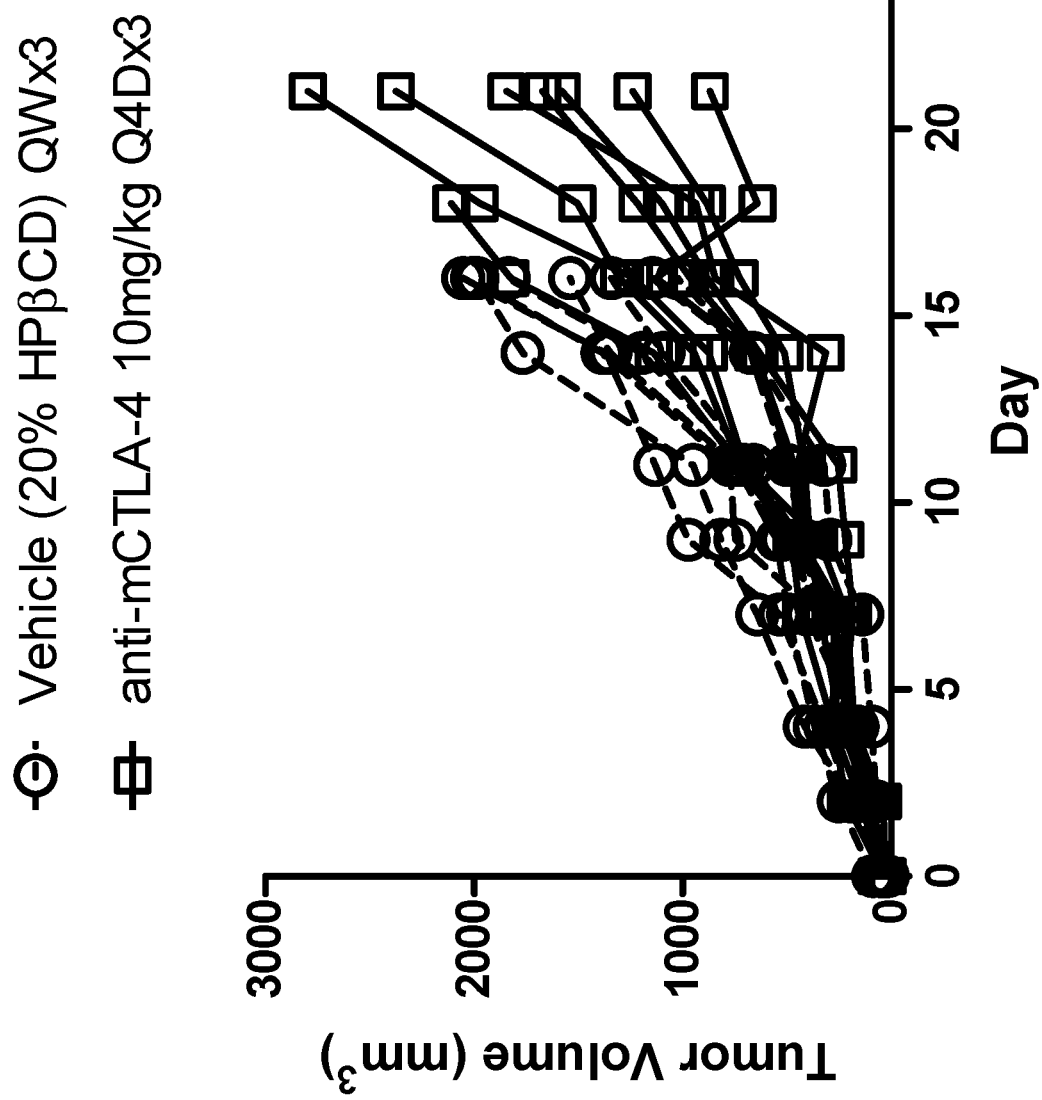
FIG. 6c: Anti-tumor activity of anti-mCTLA-4 and vehicle in mouse JC syngeneic tumor model

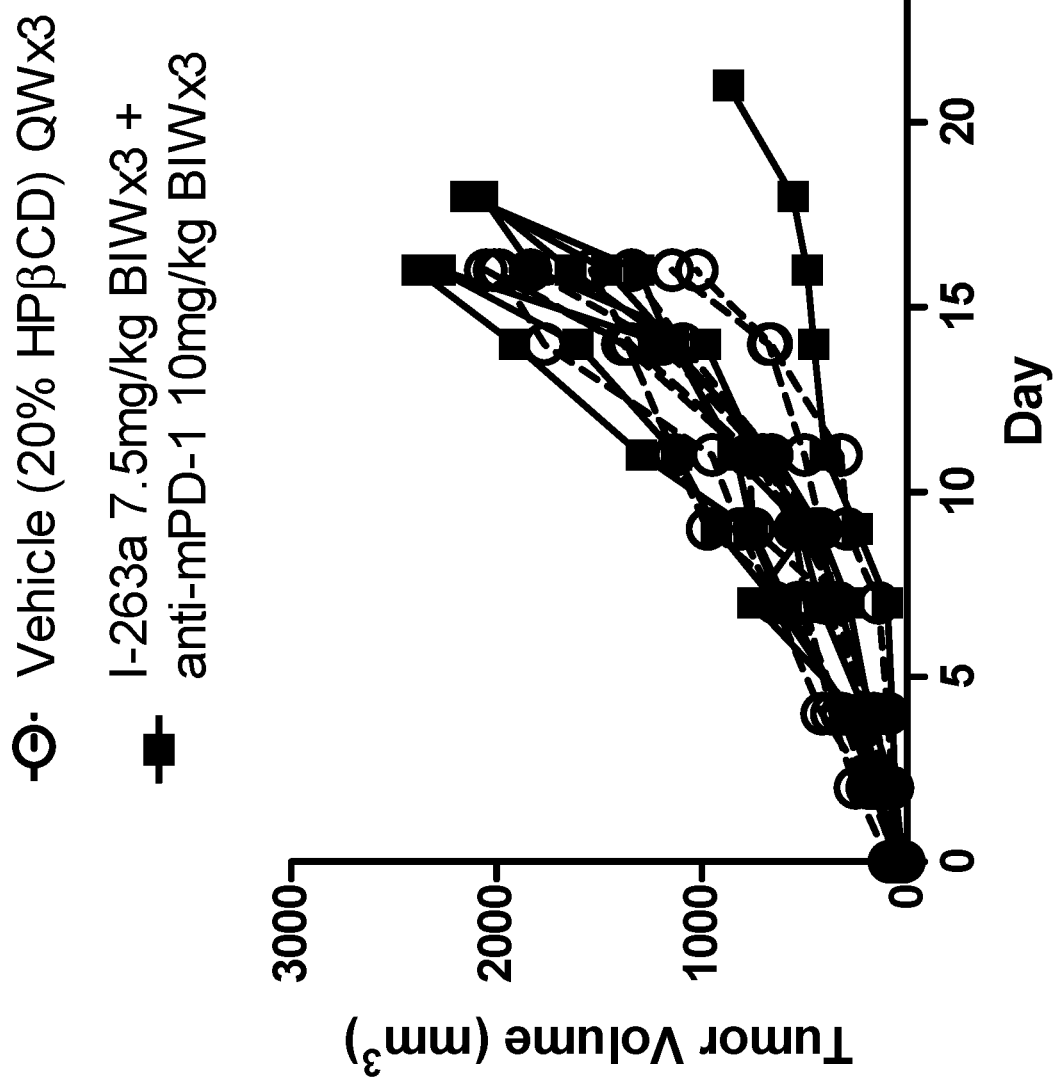
FIG. 6d: Anti-tumor activity of vehicle and combination of I-263a and anti-mPD-1 in mouse JC syngeneic tumor model

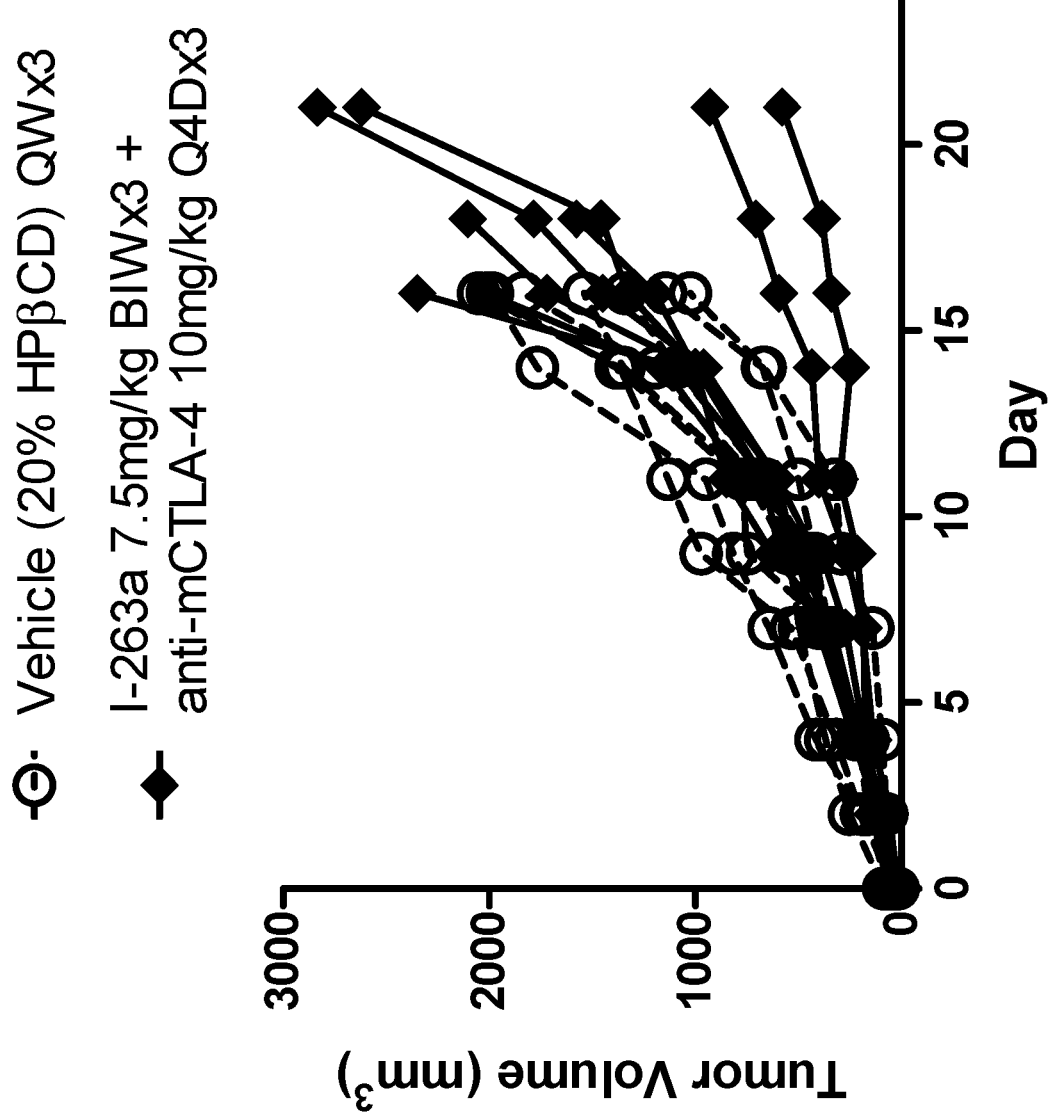
FIG. 6e: Anti-tumor activity of vehicle and combination of I-263a and anti-mCTLA-4 in mouse JC syngeneic tumor model

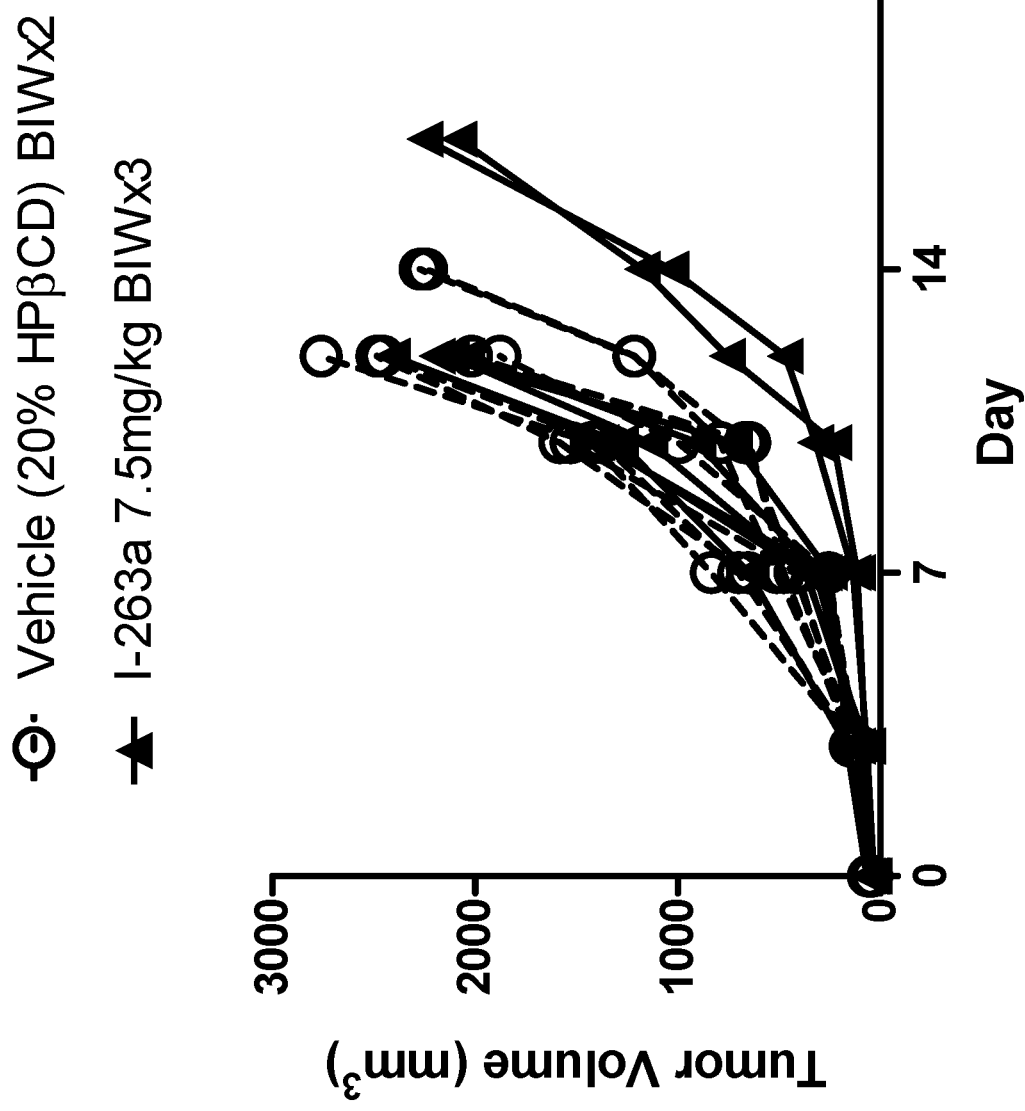
FIG. 7a: Anti-tumor activity of Compound I-263a and vehicle in mouse B16-F10 syngeneic tumor model

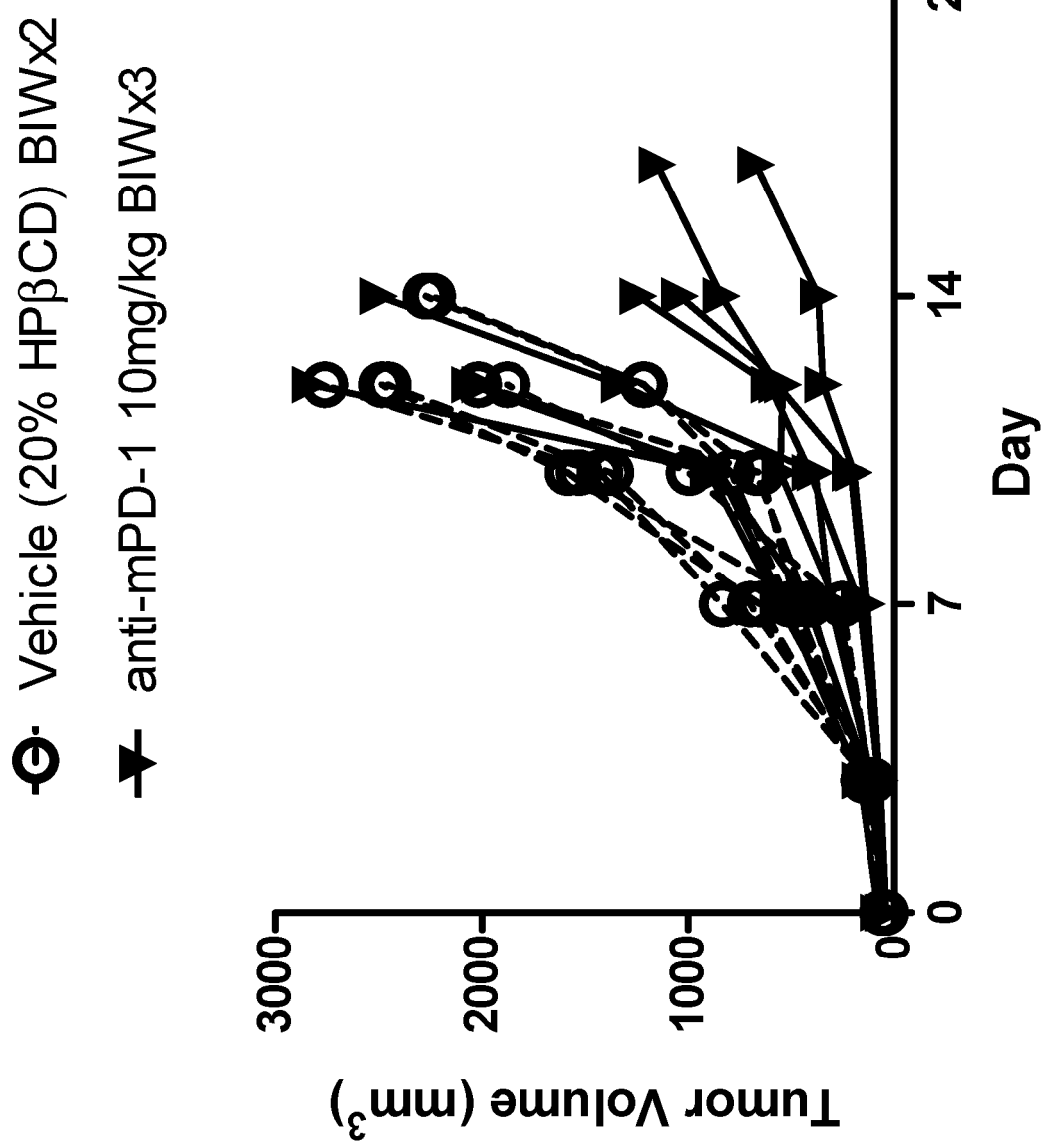
FIG. 7b: Anti-tumor activity of anti-mPD-1 and vehicle in mouse B16-F10 syngeneic tumor model

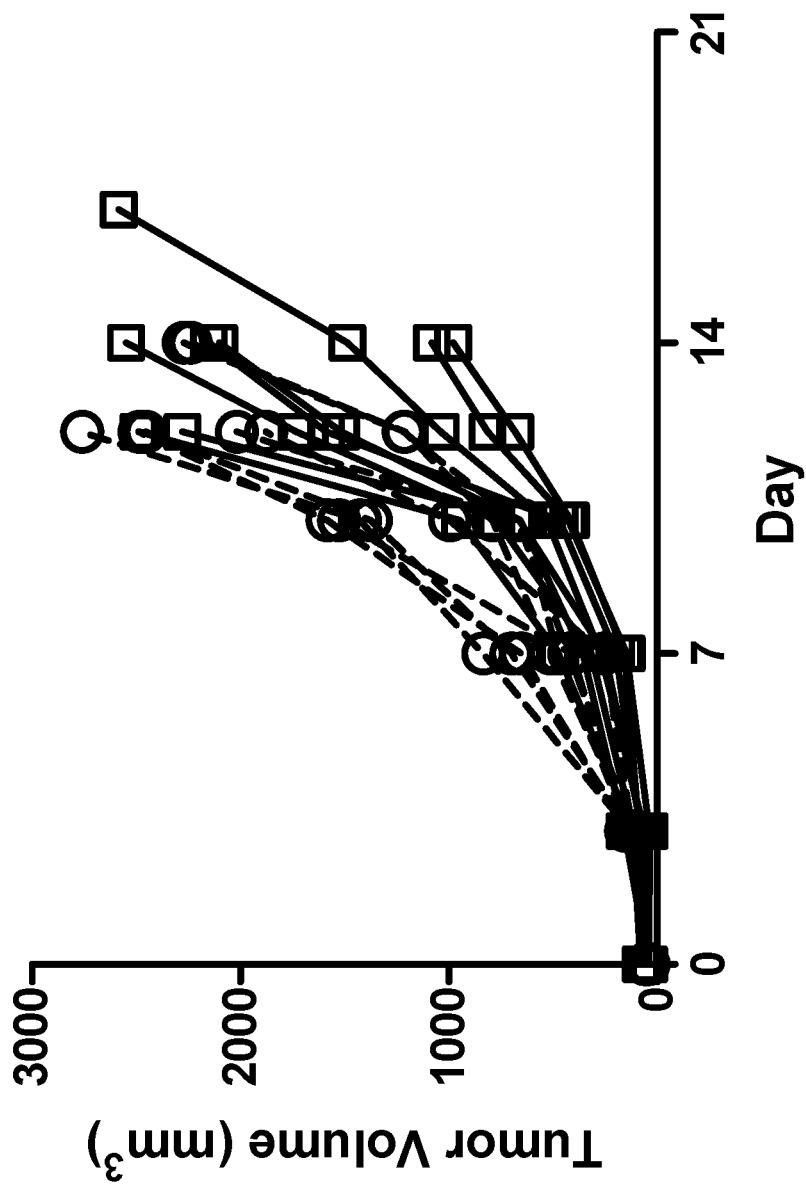
FIG. 7c: Anti-tumor activity of anti-mCTLA-4 and vehicle in mouse B16-F10 syngeneic tumor model

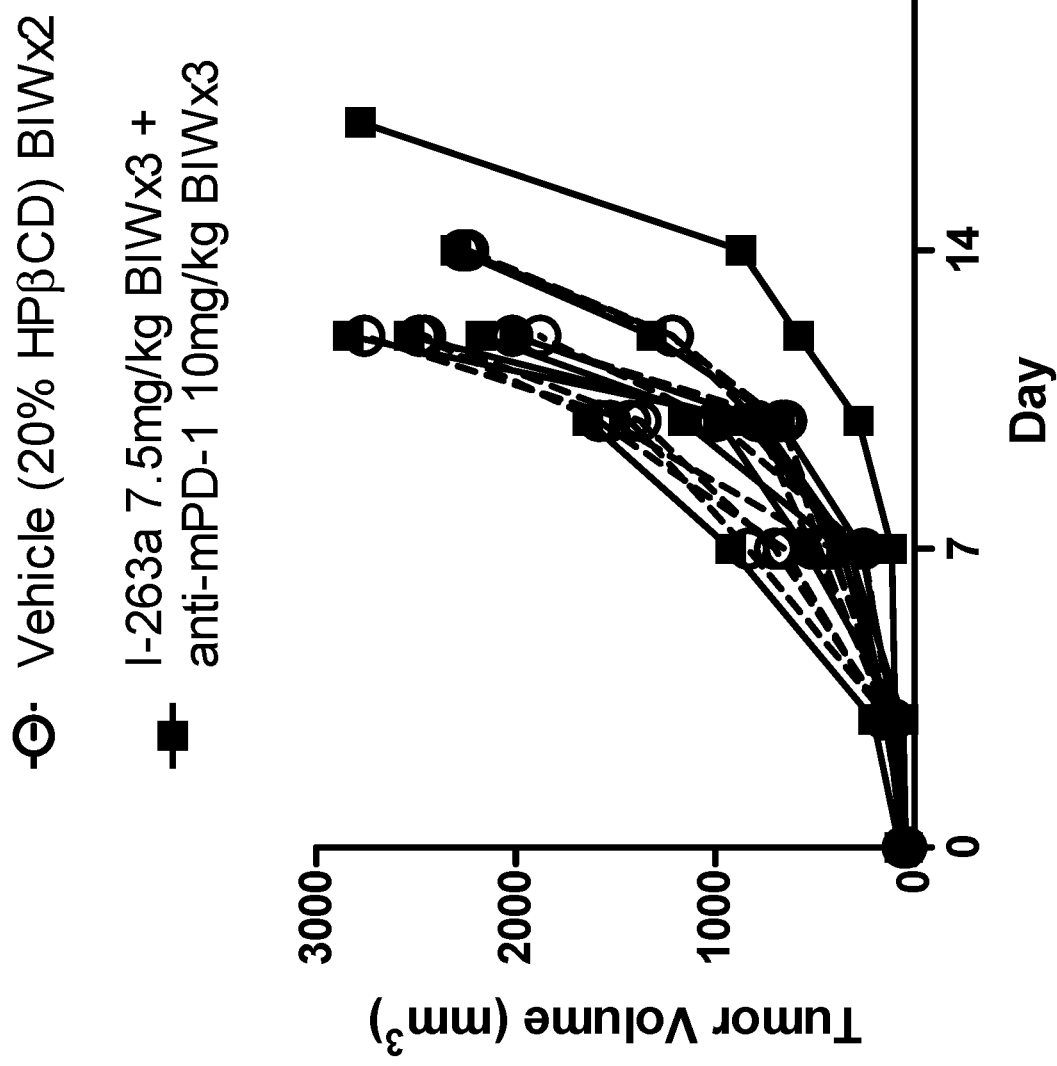
FIG. 7d: Anti-tumor activity of vehicle and combination of I-263a and anti-mPD-1 in mouse B16-F10 syngeneic tumor model

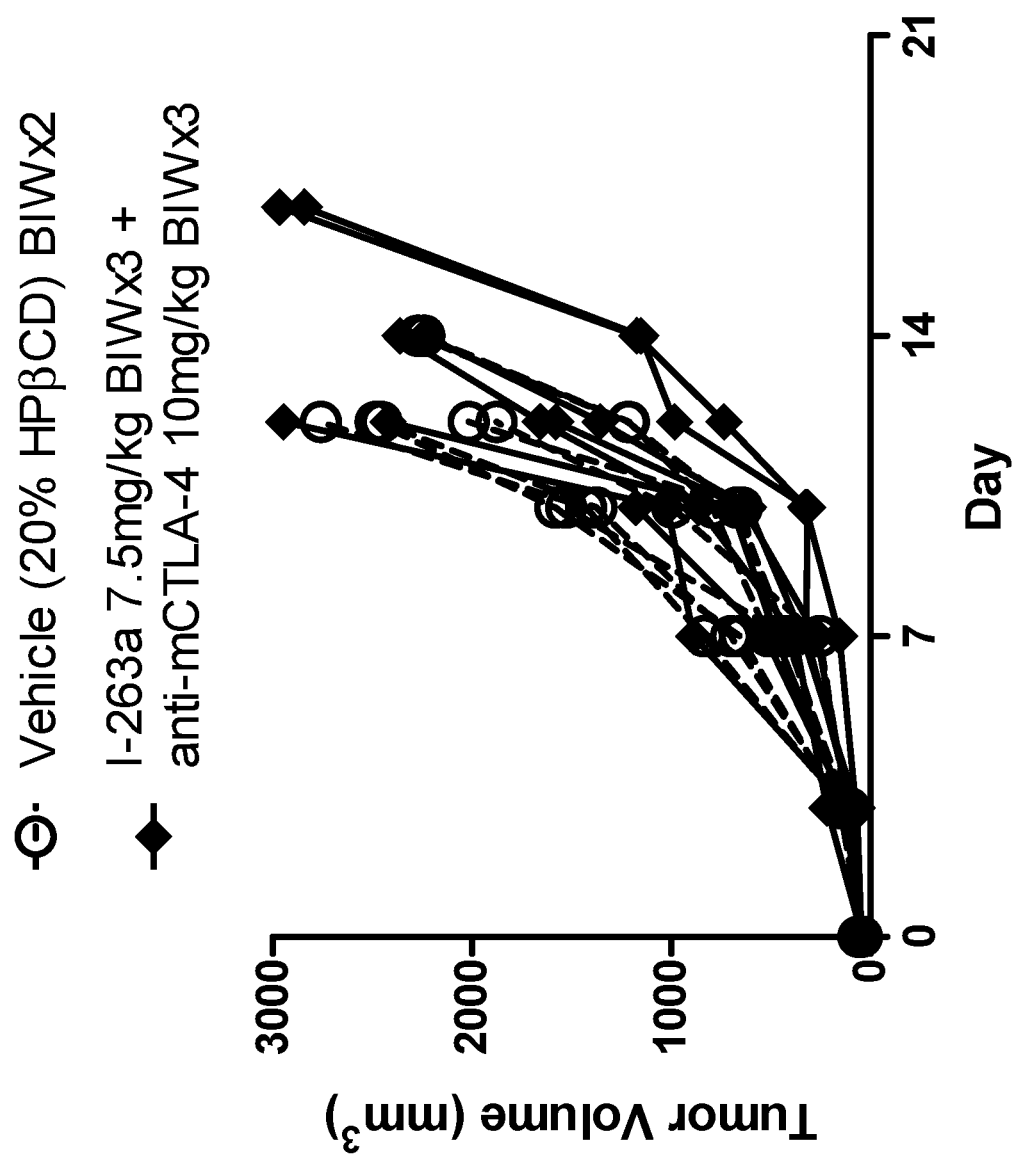
FIG. 7e: Anti-tumor activity of vehicle and combination of I-263a and anti-mCTLA-4 in mouse B16-F10 syngeneic tumor model

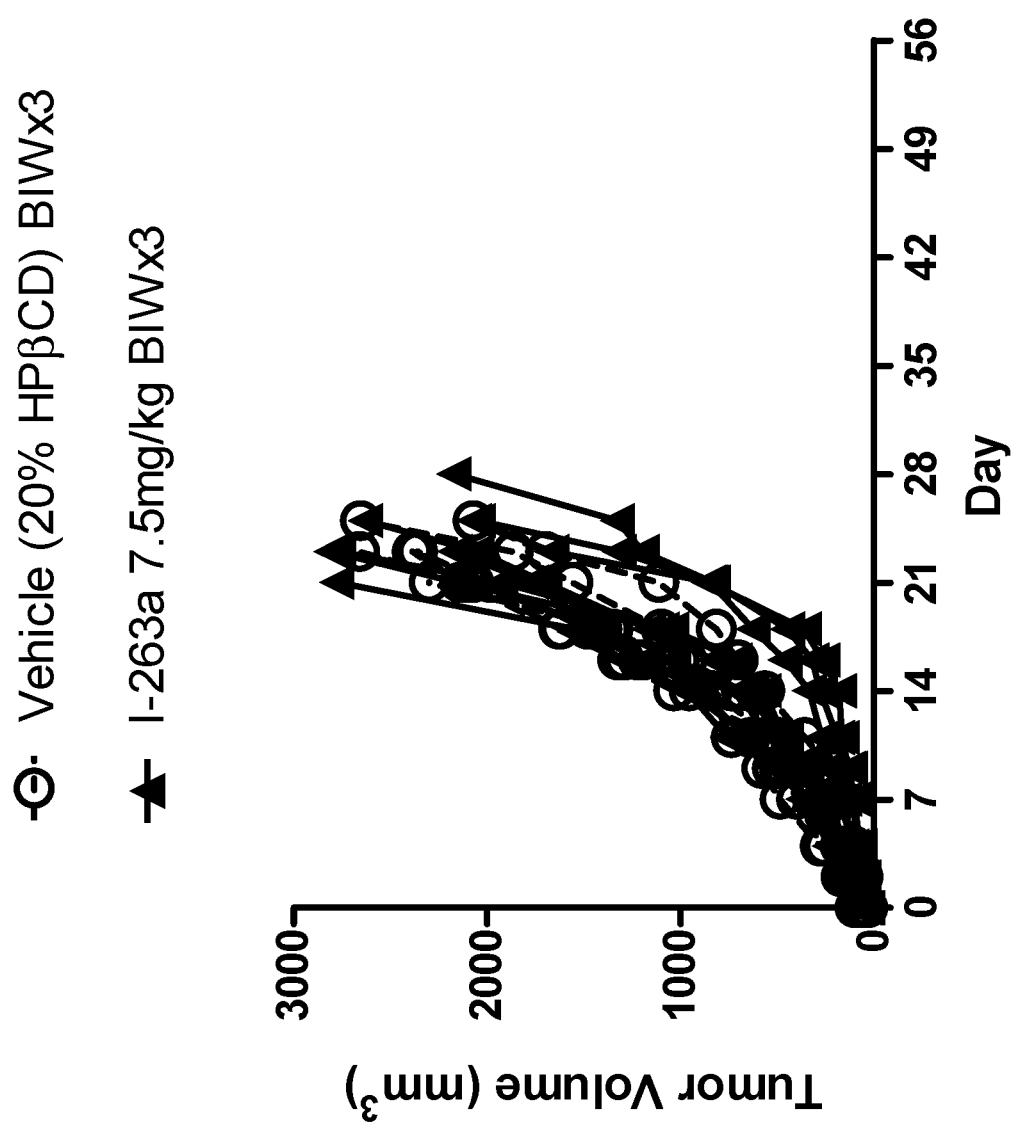
FIG. 8a: Anti-tumor activity of Compound I-263a and vehicle in mouse MC38 syngeneic tumor model

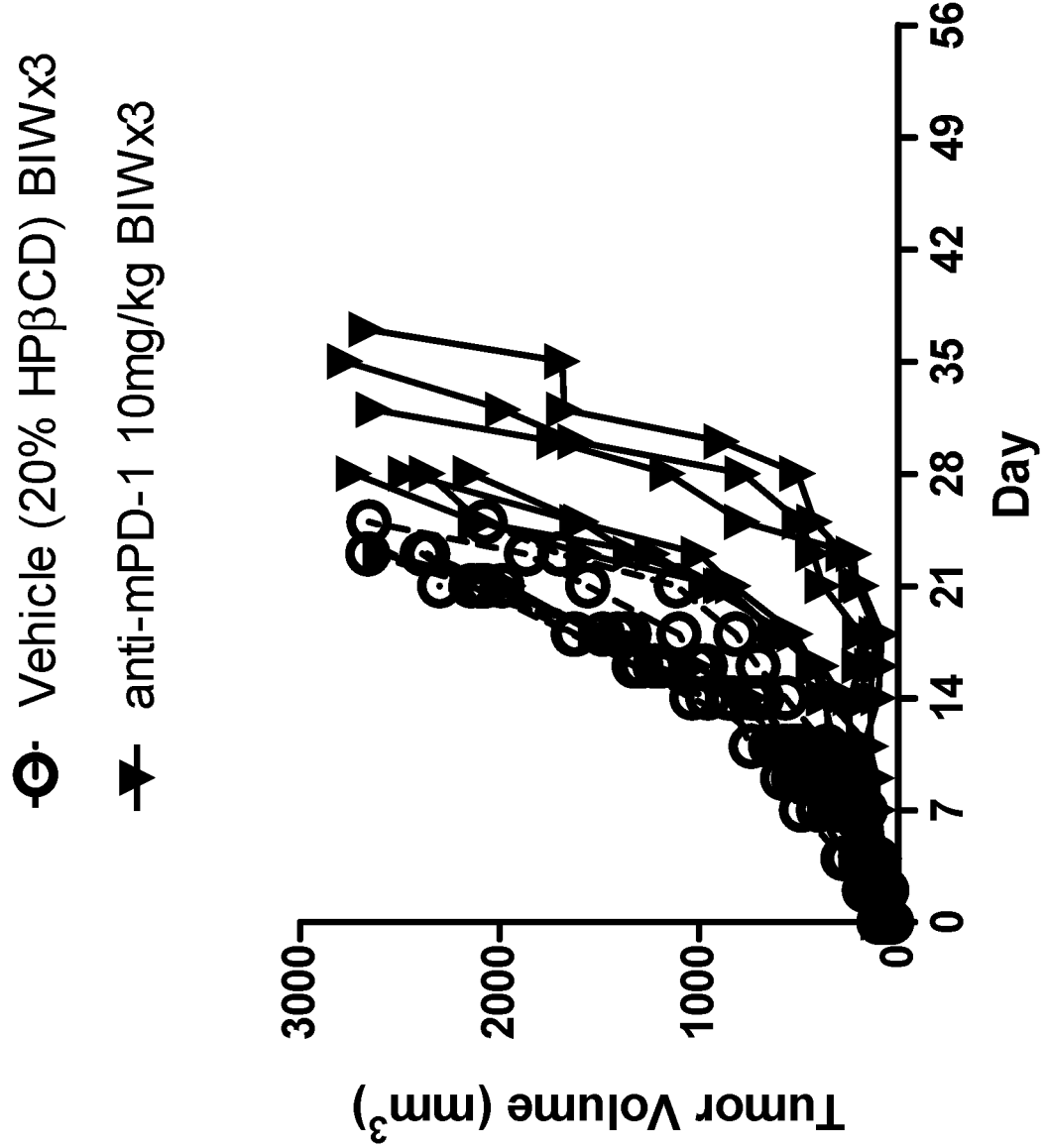
FIG. 8b: Anti-tumor activity of anti-mPD-1 and vehicle in mouse MC38 syngeneic tumor model

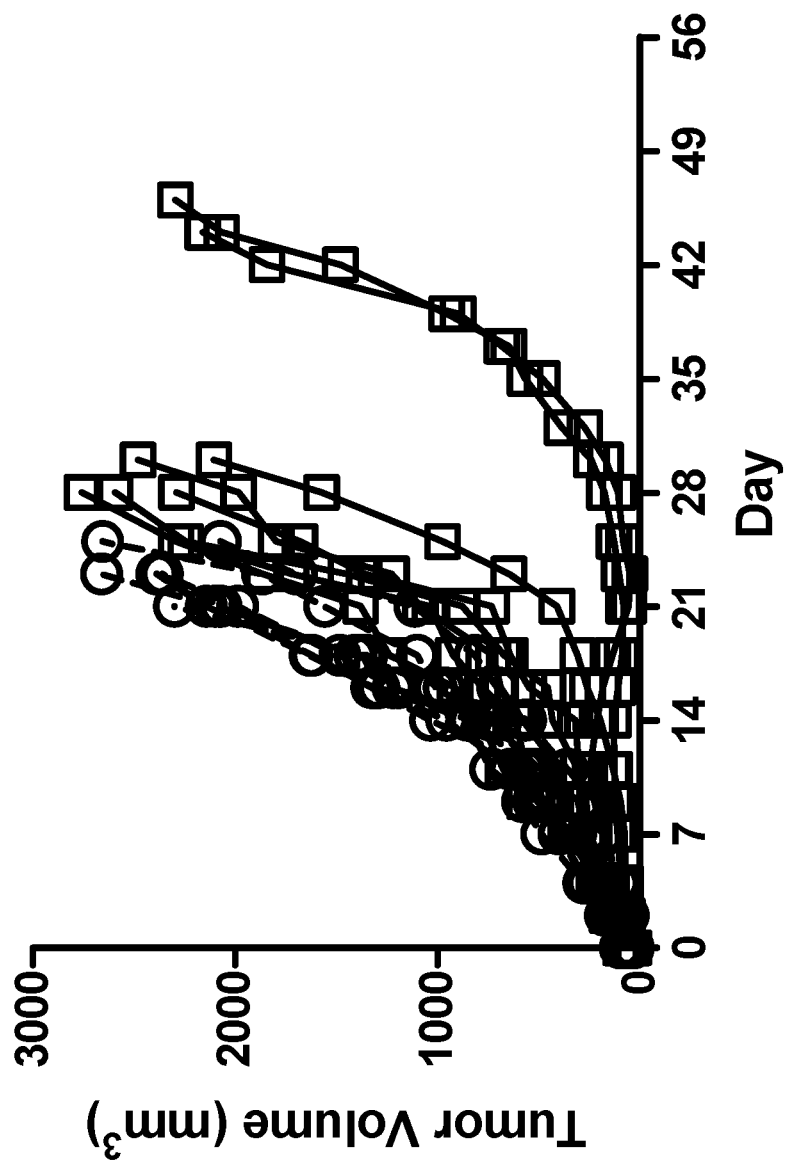
FIG. 8c: Anti-tumor activity of anti-mCTLA-4 and vehicle in mouse MC38 syngeneic tumor model

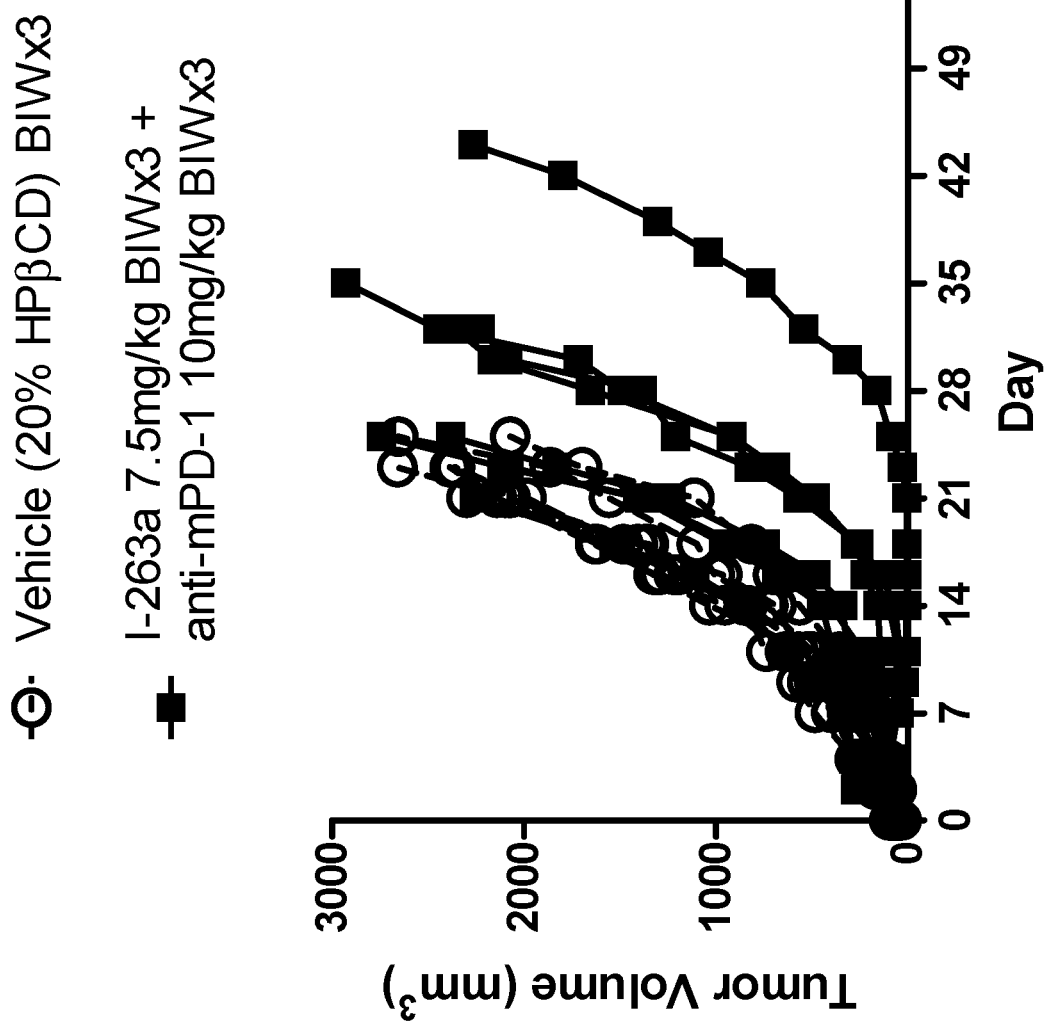
FIG. 8d: Anti-tumor activity of vehicle and a combination of I-263a and anti-mPD-1 in mouse MC38 syngeneic tumor model

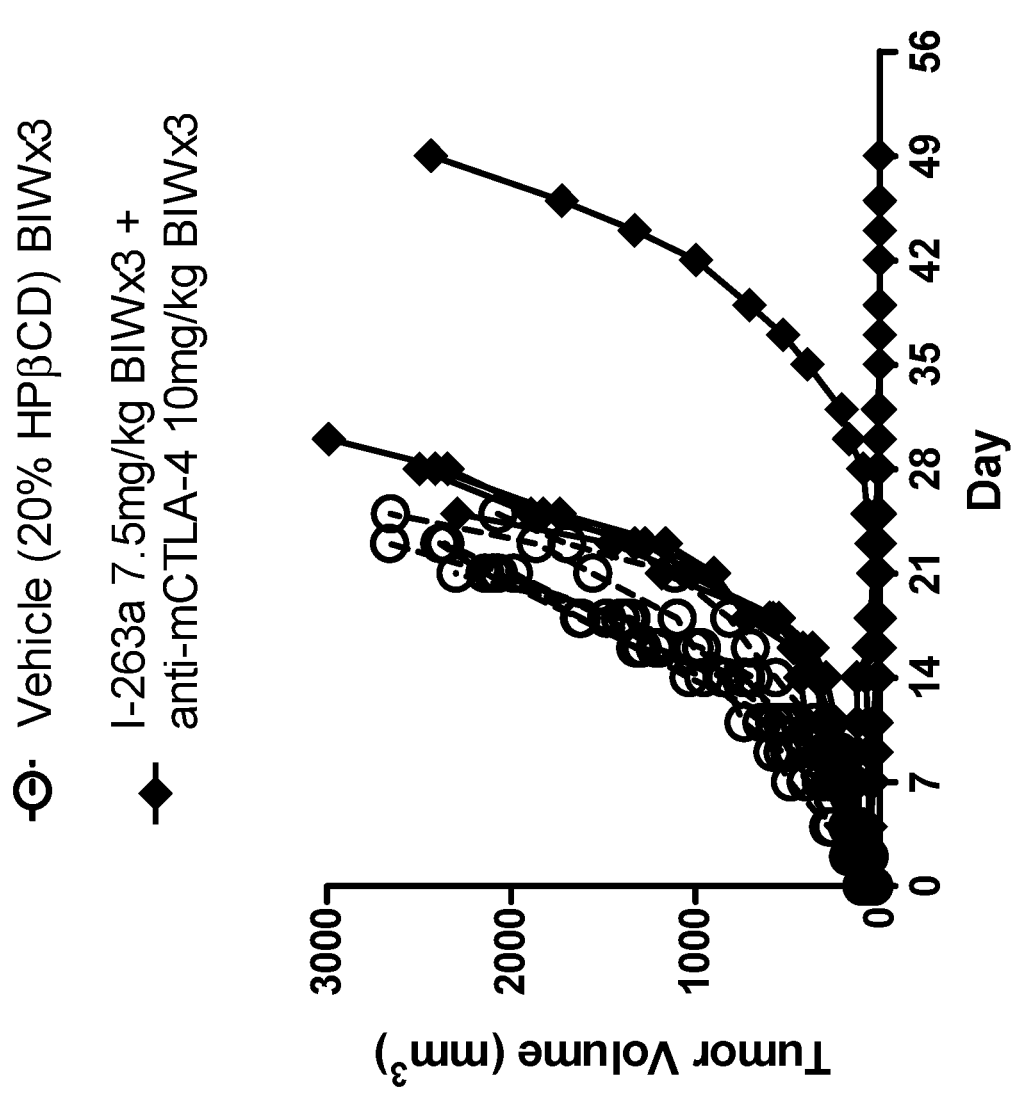
FIG. 8e: Anti-tumor activity of vehicle and a combination of I-263a and anti-mCTLA-4 in mouse MC38 syngeneic tumor model

ADMINISTRATION OF SUMO-ACTIVATING ENZYME INHIBITOR AND CHECKPOINT INHIBITORS

CROSS REFERENCE TO RELATED APPLICATIONS

The present application is a national stage application, filed under 35 U.S.C. § 371, of International Patent Application No. PCT/US2020/020171, filed on Feb. 27, 2020, which claims priority to U.S. Provisional Application No. 62/811,303, filed on Feb. 27, 2019.

FIELD

The present disclosure relates to methods of treating cancer. In particular, the present disclosure provides methods for treating various cancers by administering a small ubiquitin-like modifier (SUMO) activating enzyme (SAE) inhibitor in combination with one or more checkpoint inhibitors.

BACKGROUND

In 2012, there were an estimated 14 million cases of cancer diagnosed worldwide and about 8.2 million deaths. The global cancer burden is growing at an alarming pace; in 2030 alone, about 21.3 million new cancer cases and 13.1 million cancer deaths are expected to occur, simply due to the growth and aging of the population. Cancer is the second most common cause of death in the United States, exceeded only by heart disease, accounting for nearly one of every four deaths. The National Cancer Institute estimates that approximately 14.5 million Americans with a history of cancer were alive in 2014. Some of these individuals were cancer free, while others still had evidence of cancer and may have been undergoing treatment. Although medical advances have improved cancer survival rates, there is a continuing need for new and more effective treatment.

Cancer treatments have mainly relied on the surgery, radiotherapy, cytotoxic chemotherapies and combinations thereof. Within the last decade, however, targeted cancer therapies have opened a new era in the field of oncology. Targeted cancer therapies are drugs designed to interfere with specific molecules necessary for tumor growth and progression, and can include small molecules and larger chemical entities, such as monoclonal antibodies (mAbs).

Lung cancer is the leading cause of cancer-related mortality worldwide, with 142,670 deaths estimated in 2019 in the United States (US). Siegel, R. L., et al., *CA Cancer J Clin.* 69(1): 7-34 (2019) ("Siegel"). More than 80% of lung cancers are classified as non-small cell lung cancer (NSCLC). Although targeted therapies have redefined treatment options for patients with molecularly defined locally advanced or metastatic NSCLC (e.g., epidermal growth factor receptor [EGFR]-mutant, anaplastic lymphoma kinase [ALK]-rearranged NSCLC), these therapies are ineffective in those whose tumors lack such genetic alterations, which comprise the majority of NSCLC patients. However, immunotherapy has become integrated into the first line treatment of such patients, which has led to improvements in survival. However, despite the overall survival (OS) benefit of checkpoint inhibitors (CPI) in NSCLC, the advanced disease is incurable and will eventually progress. In the phase 1b KEYNOTE-001 trial of pembrolizumab in patients with advanced NSCLC, the 5-year OS rate in treatment-naive patients with PD-L1 expression ≥50% was 29.6%, 15.7% if PD-L1 was <50%. In patients previously treated whose PD-L1 expression levels were ≥50%, 1 to 49% and <1%, the 5-year OS rate was 25%, 12.6%, and 3.5%, respectively.

The introduction of frontline immunotherapy has changed previous treatment paradigms in NSCLC. In patients whose tumors progressed after CPI-based therapy, the choice of treatment with platinum-doublets or docetaxel depends on the chemotherapy regimen associated to the CPI in the frontline therapy. Treatment with docetaxel plus ramucirumab in second line therapy shows an overall response rate (ORR) of 23%, median progression-free survival (PFS) of 4.5 months (hazard ratio [HR]: 0.76, 95% CI 0.68-0.86), and a median OS of 10.5 months (HR: 0.86, 95% CI 0.75-0.98). Garon, E. B., et al., *Lancet* 384(9944): 665-73 (2014). The combination of a CPI with the activation of the Type I interferon (IFN) pathway may reinvigorate the pre-existing immune response and initiate a new antitumor immune response, and it has the potential to improve outcomes in NSCLC, including patients with negative PD-L1 expression tumors.

Cervical cancer is the fourth leading cause of cancer-related mortality in women worldwide, with 13,170 new cases and 4,250 deaths in 2019 in the United States. Siegel, 7-34. In contrast to patients with early-stage cervical cancer, the prognosis of patients with recurrent or metastatic disease is poor. Over the past 30 years, cisplatin-based combination chemotherapy has been shown to produce the best PFS and median OS: 5 months and 10-13 months, respectively. Moore D. H., et al., *J. Clin. Oncol.* 22(15): 3113-9 (2004); Long H. J., 3rd, et al., *J. Clin. Oncol.* 23(21): 4626-33 (2005); Monk B. J., et al., *J. Clin. Oncol.* 27(28): 4649-55 (2009). Also, the addition of bevacizumab to standard first line chemotherapy significantly improved median PFS (8.2 vs 5.9 months; HR: 0.67, 95% CI, 0.54-0.82) and median OS (17.0 vs 13.3 months; HR: 0.71, 95% CI, 0.54-0.95), compared to chemotherapy alone.

Treatment after platinum failure is a substantial challenge and currently available single-agents, such as topotecan, vinorelbine, gemcitabine, docetaxel, and nab-paclitaxel have shown unsatisfactory activity. More recently, the anti-PD-1 monoclonal antibody (mAb), pembrolizumab, received accelerated approval in June of 2018 for advanced cervical cancer with disease progression in the second line, based on the results of KEYNOTE-158 (NCT02628067), a multicenter non-randomized, open-label, multi-cohort trial. In that trial, patients were treated with pembrolizumab intravenously at a dose of 200 mg every three weeks until unacceptable toxicity or documented disease progression. Among the 98 patients, approval was based on 77 (79%) patients who had tumors that expressed PD-L1 with a combined positive score (CPS)≥1 and who had received at least one line of chemotherapy for metastatic disease.

With a median follow-up time of 11.7 months, the overall response rate (ORR) in 77 patients was 14.3% (95% CI: 7.4, 24.1), including 2.6% complete responses (CRs) and 11.7% partial responses (PRs). The estimated median duration of response (DOR) based on 11 patients with a response by independent review was not reached (range 4.1 to 18.6+ months), while 91% had a DOR of greater than or equal to 6 months.

Colorectal cancer (CRC) is the second leading cause of cancer death worldwide, with 51,020 deaths estimated during 2019 in the United States. Siegel, 7-34. Advanced stage IV metastatic disease is the initial presentation in approximately 25% of patients with CRC, and a further 25 to 50% present with early-stage disease but go on to develop metastatic disease. Despite the development of several chemotherapy regimens and the addition of EGFR/vascular endothelial growth factor A (VEGFA)-directed mAbs, the prognosis for patients with metastatic CRC remains poor, with a median 5-year survival of only 12.5% in the United States. Siegel R., et al., *CA Cancer J Clin.* 64(1): 9-29 (2014).

CRC patients that benefit from immunotherapy are patients with heavily mutated tumors that are mismatch-repair-deficient (dMMR) or that have high levels of microsatellite instability (MSI-H). In this subset of patients, the CPIs pembrolizumab, nivolumab, and the combination of nivolumab and ipilimumab received regulatory approval in the United States in 2017, 2017, and 2018, respectively. The approvals were based on data from 225 MSI-H CRC patients that progressed to fluoropyrimidine, oxaliplatin, and irinotecan containing regimens. The ORR showed by pembrolizumab, nivolumab, or the combination of ipilimumab and nivolumab were 36%, 28%, and 46%, respectively; and the DOR lasted more than six months for 78%, 67%, and 89% of the responders treated with the respective CPI. Le, D. T., et al., *New Eng. J. Med.* 372(26): 2509-20 (2015); O'Neil, B. H., et al., *PLoS One* 12(12): e0189848 (2017); Overman, M. J., et al., *Lancet Oncol.* 18(9): 1182-91 (2017); Overman, M. J., et al., *J. Clin. Oncol.* 36(8): 773-9 (2018); Le D. T., et al., *J. Clin. Oncol.* 36(15 suppl.) 3514 (2018).

Unfortunately, dMMR/MSI-H tumors represent only 5% of the metastatic CRC cases (Oliveira A. F., et al., *Front Oncol.* 9:396 (2019)) and current CPIs are ineffective in tumors that are mismatch-repair-proficient (pMMR) and microsatellite-stable (MSS) or have low levels of microsatellite instability (MSI-L). In these tumors, low tumor mutation burden and the lack of immune cell infiltration have been posited as mechanisms of immune resistance. And, once the tumor has progressed to mAb-based chemotherapeutic regimens, the two available therapeutic options, regorafenib and trifluridine-tipiracil, have shown a poor ORR of 1.6 to 3%, with a median PFS and a median OS of 2 and 7 months, respectively. Mayer, R. J., et al., *New Eng. J. Med.* 372(20): 1909-19 (2015). Van Cutsem, E., et al., *J. Clin. Oncol.* 30(28): 3499-506 (2012).

Small ubiquitin-like modifier (SUMO) activating enzyme (SAE) inhibitors are an example of small molecules that may be used for targeted therapies. SUMO is a member of the ubiquitin-like protein (Ubl) family that covalently conjugate to cellular proteins in a manner similar to ubiquitin (Ub)-conjugation (Kerscher, O. et al., *Annu Rev Cell Dev Biol.* 22:159-80 (2006)). Mammalian cells express three major SUMO isoforms: SUMO1, SUMO2, and SUMO3. SUMO2 and SUMO3 share approximately 95% amino acid sequence homology but have approximately 45% sequence homology with SUMO1 (Kamitani, T., et al., *J Biol Chem.* 273(18):11349-53 (1998)). SUMO proteins can conjugate to a single lysine residue of a protein (monosumoylation) or to a second SUMO protein that is already conjugated to a protein forming a SUMO chain (polysumoylation). Only SUMO2/3 can form such chains because they possess internal consensus SUMO modification sites (Tatham, M. H., et al., *J Biol Chem.* 276(38):35368-74 (2001)). An additional isoform, SUMO4, is found in kidney, lymph node and spleen cells, but it is not known whether SUMO4 can conjugate to cellular proteins.

SUMO1, SUMO2 and SUMO3 are activated in an ATP-dependent manner by SAE (see, for example, U.S. Patent Application Publication No. 2010/0160177 A1 (FIG. 1), U.S. Pat. No. 9,434,765 B2 (FIG. 2), and Gareau, J. R., et al., *Nat Rev Mol Cell Biol.* 11:861-871 (2010) (FIG. 1)). SAE is a heterodimer that consists of SAE1 (SUMO-activating enzyme subunit 1) and SAE2 (UBA2). SAE, like other E1 activating enzymes, uses ATP to adenylate the C-terminal glycine residue of SUMO. In a second step, a thioester intermediate is then formed between the C-terminal glycine of SUMO and a cysteine residue in SAE2. Next, SUMO is transferred from the E1 to the cysteine residue of the SUMO conjugating enzyme (E2), UBC9. Unlike the Ub pathway that contains many E2 enzymes, Ubc9 is currently the only known conjugating enzyme for SUMO and functions with SUMO1, SUMO2, and SUMO3 proteins. SUMO proteins then conjugate to the target protein, either directly or in conjunction with an E3 ligase, through isopeptide bond formation with the epsilon amino group of a lysine side chain on a target protein. Several SUMO E3 ligases, including PIAS (protein inhibitor of activated signal transducer and activator of transcription protein) proteins and Ran-binding protein 2 (RanBP2), and polycomb 2 (Pc2), have been identified (Johnson, E. S., and Gupta, A. A, *Cell.* 106(6):735-44 (2001); Pichler, A., et al., *Cell.* 108(1):109-20 (2002); Kagey, M. H., et al., *Cell.* 113(1):127-37 (2003)). Once attached to cellular targets, SUMO modulates the function, subcellular localization, complex formation and/or stability of substrate proteins (Müller, S., et al., *Nat Rev Mol Cell Biol.* 2(3):202-10 (2001)). SUMO-conjugation is reversible through the action of de-sumoylating enzymes called SENPs (Hay, R. T., *Trends Cell Biol.* 17(8):370-6 (2007)) and the SUMO proteins can then participate in additional conjugation cycles.

SAE-initiated SUMO-conjugation plays a major role in regulating diverse cellular processes, including cell cycle regulation, transcriptional regulation, cellular protein targeting, maintenance of genome integrity, chromosome segregation, and protein stability (Hay, R. T., *Mol Cell.* 18(1):1-12 (2005); Gill, G., *Genes Dev.* 18(17):2046-59 (2004)). For example, SUMO-conjugation causes changes in the subcellular localization of RanGAP1 by targeting it to the nuclear pore complex (Mahajan, R., et al., *Cell.* 88(1):97-1070 (1997)). Sumoylation counteracts ubiquitination and subsequently blocks the degradation of IκB, thereby negatively regulating NF-κB activation (Desterro, J. M., et al., *Mol Cell.* 2(2):233-9 (1998)). Sumoylation has been reported to play an important role in transcription exhibiting both repressive and stimulatory effects. Many of the transcriptional nodes that are modulated play important roles in cancer. For example, sumoylation stimulates the transcriptional activities of transcription factors such as p53 and HSF2 (Rodriguez, M. S., et al., *EMBO J.* 18(22):6455-61 (1999); Goodson, M. L., et al., *J Biol Chem.* 276(21): 18513-8 (2001)). In contrast, SUMO-conjugation represses the transcriptional activities of transcription factors such as LEF (Sachdev, S., et al., *Genes Dev.* 15(23):3088-103 (2001)) and c-Myb (Bies, J., et al., *J Biol Chem.* 277(11): 8999-9009 (2002)). Thus, SUMO-conjugation controls gene expression and growth control pathways that are important for cancer cell survival.

Altered expression of SAE pathway components have been noted in a variety of cancer types: (Moschos, S. J., et al., *Hum Pathol.* 41(9):1286-980 (2010)); including multiple myeloma (Driscoll, J. J., et al., *Blood.* 115(14):2827-34 (2010)); and breast cancer (Chen, S. F., et al., *Chin J Cancer.* 30(9):638-44 (2011)). In addition, preclinical studies indicate that Myc-driven cancers may be especially sensitive to SAE inhibition (Kessler, J. D., et al., *Science.* 335(6066): 348-53 (2012); Hoellein, A., et al., *Blood.* 124(13):2081-90 (2014)). Since SUMO-conjugation regulates essential cellular functions that contribute to the growth and survival of tumor cells, targeting SAE could represent an approach to treat proliferative disorders such as cancer. (He, X., et al., *Nature Chemical Biology.* 13: 1164-1171 (2017)). Thus, some cancers may be SAE-mediated disorders.

SAE inhibitors may also be applicable for the treatment of other diseases and conditions outside of oncology. For example, SUMO modifies proteins that play important roles in neurodegenerative diseases (Steffan, J. S., et al., *Science.* 304(5667):100-4 (2004); Dorval, V., and Fraser, P. E., *J Biol Chem.* 281(15):9919-24 (2006); Ballatore, C., et al., *Nat Rev Neurosci.* 8(9):663-72(2007)). Sumoylation also has been reported to play an important role in pathogenic viral infection, inflammation and cardiac function (Lee, H. R., et al., *J Virol.* 78(12):6527-42 (2004); Liu, B., and Shuai, K., *Mol Cell.* 35(6):731-2 (2009); Wang, J., and Schwartz, R. J., *Circ Res.* 107(1):19-29 (2010)).

In addition to small molecules, targeted therapies can include monoclonal antibodies. For example, among the many known monoclonal antibody targeted therapies are monoclonal antibodies to PD-1 (e.g., nivolumab/Opdivo®, and pembrolizumab/Keytruda®), monoclonal antibodies to PD-L1 (e.g., atezolizumab/Tecentriq®, durvalumab/Imfinzi®, and avelumab/Bavencio®), and monoclonal antibodies to CTLA-4 (e.g., ipilimumab/Yervoy®). Thus, some cancers may be PD-1-mediated disorders, PD-L1-mediated disorders, and CTLA-4-mediated disorders. Additional monoclonal antibody targeted therapies include, but are not limited to, monoclonal antibodies to CD20 (e.g. rituximab/Rituxan®) CD52 (e.g., alemtuzumab/Campath®), VEGF (e.g., bevacizumab/Avastin®), HER2 (e.g., trastuzumab/Herceptin® for treating Her2+ breast and stomach cancers), and EGFR (e.g., cetuximab/Erbitux® for treating colorectal cancer).

New combinations of therapeutic agents that provide a beneficial effect in the treatment of cancers are desirable in order to prolong patient's lives while maintaining a high quality of life. New combinations may provide an increased benefit as compared to each of the agents alone. In particular, combined treatment regimens may be helpful for patients suffering from disease conditions including proliferative disorders, autoimmune diseases, inflammatory diseases, fibrotic diseases and kidney diseases, and could potentially even decrease the rate of relapse or overcome the resistance to a particular anticancer agent sometimes seen in these patients. This is especially true in the case where the cancers may be resistant or refractory to currently available therapeutic regimens.

Thus, there is a need for new cancer treatment regimens, including combination therapies.

SUMMARY

In one aspect, the present disclosure relates to methods of treating cancer comprising administering an SAE inhibitor and a checkpoint inhibitor in combination to a subject in need of such treatment.

In one aspect, the present disclosure relates to methods of treating a patient having cancer, comprising administering to a patient in need of said treating a combination of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and a checkpoint inhibitor. Compound I-263a is also referred to herein as TAK-981.

In some embodiments, the checkpoint inhibitor is an anti-PD-1 antibody.

In some embodiments, the anti-PD-1 antibody is selected from the group consisting of nivolumab, pembrolizumab, lambrolizumab, pidilizumab, BMS-936559, and AMP-224.

In some embodiments, the checkpoint inhibitor is an anti-PD-L1 antibody.

In some embodiments, the anti-PD-L1 antibody is selected from the group consisting of atezolizumab, durvalumab, avelumab, YW243.55.S70, MEDI-4736, MSB-0010718C, LY3300054, BMS-936559, MPDL3280A, and MDX-1105.

In some embodiments, the checkpoint inhibitor is an anti-CTLA-4 antibody.

In some embodiments, the anti-CTLA-4 antibody is selected from the group consisting of ipilimumab and tremelimumab.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, is administered orally.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, is administered intravenously.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, is administered by intravenous infusion.

In some embodiments, the checkpoint inhibitor is administered intravenously.

In some embodiments, the checkpoint inhibitor is administered by intravenous infusion.

In some embodiments, the checkpoint inhibitor is administered by subcutaneous injection.

In some embodiments, the checkpoint inhibitor is administered subcutaneously.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate and the checkpoint inhibitor are administered concurrently.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate and the checkpoint inhibitor are administered sequentially in separate pharmaceutical compositions.

In some embodiments, the cancer is PD-1 positive cancer, a PD-L1 positive cancer, or a CTLA-4 positive cancer.

In some embodiments, the cancer is a solid tumor or a hematological malignancy. In some embodiments, the solid tumor is an advanced solid tumor. In some embodiments, the solid tumor is a metastatic solid tumor. In some embodiments, the solid tumor is an unresectable solid tumor.

In some embodiments, the cancer is melanoma, lung cancer, renal cancer, lymphoma, head and neck cancer, urothelial cancer, prostate cancer, bladder cancer, breast cancer, gastric cancer, colorectal cancer, leukemia, cervical cancer, microsatellite instability-high cancer, hepatocellular carcinoma, or Merkel cell carcinoma.

In some embodiments, the cancer is cervical cancer. In some embodiments, the cancer is CPI-naïve cervical cancer. In some embodiments, the cancer is squamous cell carcinoma, adenosquamous carcinoma, or adenocarcinoma of the cervix.

In some embodiments the cancer is colorectal cancer. In some embodiments, the cancer is microsatellite stable colorectal cancer (MSS-CRC). In some embodiments, the cancer is CPI-naïve MSS-CRC.

In some embodiments, the melanoma is metastatic melanoma, unresectable melanoma, or cutaneous melanoma.

In some embodiments, the lung cancer is non-small cell lung cancer (NSCLC) or small cell lung cancer.

In some embodiments, the non-small cell lung cancer is metastatic non-small cell lung cancer, metastatic squamous non-small cell lung cancer, or metastatic nonsquamous non-small cell lung cancer. In some embodiments, the non-small cell lung cancer is non-small cell lung cancer adenocarcinoma.

In some embodiments, the renal cancer is renal cell carcinoma.

In some embodiments, the lymphoma is classical Hodgkin lymphoma or primary mediastinal large B-cell lymphoma.

In some embodiments, the head and neck cancer is head and neck squamous cell carcinoma.

In some embodiments, the urothelial cancer is urothelial carcinoma.

In some embodiments, the prostate cancer is hormone-refractory prostate cancer.

In some embodiments, the gastric cancer is gastroesophageal junction adenocarcinoma.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, is administered once every two weeks, once every week, twice a week, three times a week, or daily.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, is administered twice a week.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, is administered once every week.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, is administered on days 1, 4, 8, and 11 of a 21 day cycle.

In some embodiments, the checkpoint inhibitor is administered once every twelve weeks, once every four weeks, once every three weeks, once every two weeks, once every week, twice a week, three times a week, or daily.

In some embodiments, the checkpoint inhibitor is administered once every two weeks.

In some embodiments, the checkpoint inhibitor is administered once every three weeks.

In some embodiments, the checkpoint inhibitor is administered once every four weeks.

In some embodiments, the checkpoint inhibitor is administered once every twelve weeks.

In some embodiments, the checkpoint inhibitor is administered on Day 1 of a treatment cycle.

In some embodiments, the treatment cycle is 14 days, 21 days, 28 days, or 84 days.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, and the checkpoint inhibitor are administered simultaneously once every twelve weeks, once every four weeks, once every three weeks, once every two weeks, once every week, twice a week, three times a week, daily, or on days 1, 4, 8, and 11 of a 21 day cycle.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, is administered once every two weeks, once every week, twice a week, three times a week, daily, or on days 1, 4, 8, and 11 of a 21 day cycle; and the checkpoint inhibitor is separately administered once every twelve weeks, once every four weeks, once every three weeks, once every two weeks, once every week, twice a week, three times a week, or daily.

In one aspect, the present disclosure relates to a kit comprising a medicament for use in treating cancer in a subject in need of such treatment. The kit comprises a medicament comprising an SAE inhibitor, and instructions for administering the SAE inhibitor and the one or more checkpoint inhibitors; or the kit comprises a medicament comprising the one or more checkpoint inhibitors, and instructions for administering the one or more checkpoint inhibitors and an SAE inhibitor. The kit can contain both a medicament comprising an SAE inhibitor and a medicament comprising one or more checkpoint inhibitors, and instructions for administering the SAE inhibitor and the one or more checkpoint inhibitors. The kit can also comprise one or more additional therapeutic agents.

In one aspect, the present disclosure relates to a medicament for use in treating cancer in a subject in need of such treatment. The medicament comprises an SAE inhibitor and one or more checkpoint inhibitors. The medicament can also comprise one or more additional therapeutic agents.

BRIEF DESCRIPTION OF THE FIGURES

FIG. 1a shows a plot of individual tumor volume as a function of time in a CT26 syngeneic tumor model following administration of Compound I-263a and vehicle to mice.

FIG. 1b shows a plot of individual tumor volume as a function of time in a CT26 syngeneic tumor model following administration of vehicle and an anti-mouse PD-1 ("anti-mPD-1") antibody to mice.

FIG. 1c shows a plot of individual tumor volume as a function of time in a CT26 syngeneic tumor model following administration of vehicle and a combination of Compound I-263a and an anti-mPD-1 antibody to mice.

FIG. 2a shows a plot of individual tumor volume as a function of time in a CT26 syngeneic tumor model following administration of Compound I-263a and vehicle to mice.

FIG. 2b shows a plot of individual tumor volume as a function of time in a CT26 syngeneic tumor model following administration of vehicle and an anti-mPD-1 antibody to mice.

FIG. 2c shows a plot of individual tumor volume as a function of time in a CT26 syngeneic tumor model following administration of vehicle and a combination of Compound I-263a and an anti-mPD-1 antibody to mice.

FIG. 3a shows a plot of individual tumor volume as a function of time in an A20 syngeneic tumor model following administration of Compound I-263a and vehicle to mice.

FIG. 3b shows a plot of individual tumor volume as a function of time in an A20 syngeneic tumor model following administration of vehicle and an anti-mPD-1 antibody to mice.

FIG. 3c shows a plot of individual tumor volume as a function of time in an A20 syngeneic tumor model following administration of vehicle and a combination of Compound I-263a and an anti-mPD-1 antibody to mice.

FIG. 4a shows a plot of individual tumor volume as a function of time in a WEHI-3 syngeneic tumor model following administration of Compound I-263a and vehicle to mice.

FIG. 4b shows a plot of individual tumor volume as a function of time in a WEHI-3 syngeneic tumor model following administration of an anti-mPD-1 antibody and vehicle to mice.

FIG. 4c shows a plot of individual tumor volume as a function of time in a WEHI-3 syngeneic tumor model following administration of an anti-mouse CTLA-4 ("anti-mCTLA-4") antibody and vehicle to mice.

FIG. 4d shows a plot of individual tumor volume as a function of time in a WEHI-3 syngeneic tumor model following administration of vehicle and a combination of Compound I-263a and an anti-mPD-1 antibody to mice.

FIG. 4e shows a plot of individual tumor volume as a function of time in a WEHI-3 syngeneic tumor model following administration of vehicle and a combination of Compound I-263a and an anti-mCTLA-4 antibody to mice.

FIG. 5a shows a plot of individual tumor volume as a function of time in a WEHI-3 syngeneic tumor model following administration of Compound I-263a and vehicle to mice.

FIG. 5b shows a plot of individual tumor volume as a function of time in a WEHI-3 syngeneic tumor model following administration of an anti-mPD-1 antibody and vehicle to mice.

FIG. 5c shows a plot of individual tumor volume as a function of time in a WEHI-3 syngeneic tumor model following administration of an anti-mCTLA-4 antibody and vehicle to mice.

FIG. 5d shows a plot of individual tumor volume as a function of time in a WEHI-3 syngeneic tumor model following administration of vehicle and a combination of Compound I-263a and an anti-mPD-1 antibody to mice.

FIG. 5e shows a plot of individual tumor volume as a function of time in a WEHI-3 syngeneic tumor model following administration of vehicle and a combination of Compound I-263a and an anti-mCTLA-4 antibody to mice.

FIG. 6a shows a plot of individual tumor volume as a function of time in a JC syngeneic tumor model following administration of Compound I-263a and vehicle to mice.

FIG. 6b shows a plot of individual tumor volume as a function of time in a JC syngeneic tumor model following administration of an anti-mPD-1 antibody and vehicle to mice.

FIG. 6c shows a plot of individual tumor volume as a function of time in a JC syngeneic tumor model following administration of an anti-mCTLA-4 antibody and vehicle to mice.

FIG. 6d shows a plot of individual tumor volume as a function of time in a JC syngeneic tumor model following administration of vehicle and a combination of Compound I-263a and an anti-mPD-1 antibody to mice.

FIG. 6e shows a plot of individual tumor volume as a function of time in a JC syngeneic tumor model following administration of vehicle and a combination of Compound I-263a and an anti-mCTLA-4 antibody to mice.

FIG. 7a shows a plot of individual tumor volume as a function of time in a B16-F10 syngeneic tumor model following administration of Compound I-263a and vehicle to mice.

FIG. 7b shows a plot of individual tumor volume as a function of time in a B16-F10 syngeneic tumor model following administration of an anti-mPD-1 antibody and vehicle to mice.

FIG. 7c shows a plot of individual tumor volume as a function of time in a B16-F10 syngeneic tumor model following administration of an anti-mCTLA-4 antibody and vehicle to mice.

FIG. 7d shows a plot of individual tumor volume as a function of time in a B16-F10 syngeneic tumor model following administration of vehicle and a combination of Compound I-263a and an anti-mPD-1 antibody to mice.

FIG. 7e shows a plot of individual tumor volume as a function of time in a B16-F10 syngeneic tumor model following administration of vehicle and a combination of Compound I-263a and an anti-mCTLA-4 antibody to mice.

FIG. 8a shows a plot of individual tumor volume as a function of time in a MC38 syngeneic tumor model following administration of Compound I-263a and vehicle to mice.

FIG. 8b shows a plot of individual tumor volume as a function of time in a MC38 syngeneic tumor model following administration of an anti-mPD-1 antibody and vehicle to mice.

FIG. 8c shows a plot of individual tumor volume as a function of time in a MC38 syngeneic tumor model following administration of an anti-mCTLA-4 antibody and vehicle to mice.

FIG. 8d shows a plot of individual tumor volume as a function of time in a MC38 syngeneic tumor model following administration of vehicle and a combination of Compound I-263a and an anti-mPD-1 antibody to mice.

FIG. 8e shows a plot of individual tumor volume as a function of time in a MC38 syngeneic tumor model following administration of vehicle and a combination of Compound I-263a and an anti-mCTLA-4 antibody to mice.

DETAILED DESCRIPTION

Definitions and Abbreviations

To facilitate an understanding of the present disclosure, a number of abbreviations, terms, and phrases are defined below.

AUC area under the plasma concentration versus time curve
BSA body surface area
CR complete response
MTD maximum tolerated dose
SUMO small ubiquitin-like modifier
SAE SUMO-activating enzyme
PR partial response
BIW twice weekly
QW once weekly
Q2W once every 2 weeks
QD once daily
Q Every
NSCLC non-small cell lung cancer
SCLC small cell lung cancer
MSS-CRC microsatellite stable colorectal cancer Unless defined otherwise, all technical and scientific terms used herein have the same meaning as is commonly understood by one of skill in the art to which this disclosure belongs. All patents and publications referred to herein are incorporated by reference in their entirety.

As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer" includes solid tumors and non-solid tumors, such as, for example, hematological tumors. The term "cancer" encompasses diseases of skin, tissues, organs, bone, cartilage, blood, and vessels. The term "cancer" further encompasses primary and metastatic cancers.

As used herein, the term "autoimmune disease" refers to a disorder arising from an abnormal immune response to a normal body part. The term "autoimmune disease" encompasses disorders including, but not limited to, Rheumatoid Arthritis (RA), Granulomatosis with Polyangiitis (GPA) (Wegener's Granulomatosis), and Microscopic Polyangiitis (MPA).

The term "PD-1" (also known as programmed cell death protein 1, PDCD1, CD279, SLEB2, or SLE1) refers to any native PD-1, unless otherwise indicated. The term "PD-1" encompasses "full-length," unprocessed PD-1 as well as any form of PD-1 that results from processing within the cell. The term also encompasses naturally occurring variants of PD-1, e.g., splice variants, allelic variants, and isoforms.

The term "PD-L1" (also known as programmed cell death 1 ligand) refers to any native PD-L1, unless otherwise indicated. The term "PD-L1" encompasses "full-length," unprocessed PD-L1 as well as any form of PD-L1 that results from processing within the cell. The term also encompasses naturally occurring variants of PD-L1, e.g., splice variants, allelic variants, and isoforms.

The term "CTLA-4" (also known as cytotoxic T-lymphocyte-associated antigen 4) refers to any native CTLA-4, unless otherwise indicated. The term "CTLA-4" encompasses "full-length," unprocessed CTLA-4 as well as any form of CTLA-4 that results from processing within the cell. The term also encompasses naturally occurring variants of CTLA-4, e.g., splice variants, allelic variants, and isoforms.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as, e.g., PD-1, PD-L1, or CTLA-4. In a certain embodiment, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-PD-1 antibody" or "an antibody that binds to PD-1" refers to an antibody that is capable of binding PD-1 with sufficient affinity such that the antibody is useful as a diagnostic and/or therapeutic agent in targeting PD-1. The extent of binding of an anti-PD-1 antibody to an unrelated, non-PD-1 protein is less than about 10% of the binding of the antibody to PD-1 as measured, e.g., by a radioimmunoassay (RIA). In certain embodiments, an antibody that binds to PD-1 has a dissociation constant (Kd) of $\leq 1$ µM, $\delta 100$ nM, $\leq 10$ nM, $\leq 1$ nM, or $\leq 0.1$ nM.

The term "anti-PD-L1 antibody" or "an antibody that binds to PD-L1" refers to an antibody that is capable of binding PD-L1 with sufficient affinity such that the antibody is useful as a diagnostic and/or therapeutic agent in targeting PD-L1. The extent of binding of an anti-PD-L1 antibody to an unrelated, non-PD-L1 protein is less than about 10% of the binding of the antibody to PD-L1 as measured, e.g., by a radioimmunoassay (RIA). In certain embodiments, an antibody that binds to PD-L1 has a dissociation constant (Kd) of $\leq 1$ nM, $\leq 100$ nM, $\leq 10$ nM, $\leq 1$ nM, or $\leq 0.1$ nM.

The term "anti-CTLA-4 antibody" or "an antibody that binds to CTLA-4" refers to an antibody that is capable of binding CTLA-4 with sufficient affinity such that the antibody is useful as a diagnostic and/or therapeutic agent in targeting CTLA-4. The extent of binding of an anti-CTLA-4 antibody to an unrelated, non-CTLA-4 protein is less than about 10% of the binding of the antibody to CTLA-4 as measured, e.g., by a radioimmunoassay (RIA). In certain embodiments, an antibody that binds to CTLA-4 has a dissociation constant (Kd) of $\leq 1$ µM, $\leq 100$ nM, $\leq 10$ nM, $\leq 1$ nM, or $\leq 0.1$ nM.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

As used herein, the term "effective amount" or "therapeutically effective amount" refers to an amount of a compound, or combination of one or more compounds that, when administered (either sequentially or simultaneously)

elicits the desired biological or medicinal response, e.g., either destroys the target cancer cells or slows or arrests the progression of the cancer in a patient. The therapeutically effective amount may vary depending upon the intended application (in vitro or in vivo), or the patient and disease condition being treated, e.g., the weight and age of the patient, the severity of the disease condition, the manner of administration and the like, which may readily be determined by one skilled in the art. The term also applies to a dose that will induce a particular response in target cells, e.g., reduction of platelet adhesion and/or cell migration. For example, in some embodiments, the "therapeutically effective amount" as used herein refers to the amount of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, and the amount of checkpoint inhibitor that, when administered separately or in combination, have a beneficial effect. In some embodiments, the combined effect is additive. In some embodiments, the combined effect is synergistic. Further, it will be recognized by one skilled in the art that in the case of combination therapy, the amount of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof and/or the amount of the checkpoint inhibitor may be used in a "sub-therapeutic amount", i.e., less than the therapeutically effective amount of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, or the checkpoint inhibitor alone.

In any form or composition, the administered dose(s) or the therapeutically effective (total) amount may be expressed as amount(s) of therapeutic substance(s) per patient as either based on (i) BSA, e.g., as mg/m$^2$, or (ii) amount, e.g., as mg.

The term "about" refers to approximately, in the region of, roughly, or around. When the term "about" is used in conjunction with a number or a numerical range, it means that the number or numerical range referred to is an approximation within experimental variability (or within statistical experimental error), and thus the number or numerical range may vary from, for example, between 1% and 15% of the stated number or numerical range. In general, the term "about" is used herein to modify a numerical value above and below the stated value by a variance of ±10%.

As used herein, "patient" generally means a mammal (e.g., human) who has been diagnosed with, exhibits symptoms of, or is otherwise believed to be afflicted with a disease, disorder, or condition (such as cancer).

As used herein, "body surface area" (BSA) is calculated using a standard nomogram, e.g., $$BSA(m^2) = \sqrt{\frac{Ht(cm) \times Wt(kg)}{3600}} \text{ or}$$

$$BSA = \sqrt{\frac{Ht(in) \times Wt(lb)}{3131}}.$$

The term "combination administration," "administered in combination," and "administering a combination" refers to administering of more than one pharmaceutically active ingredients (including, but not limited to, [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, and a checkpoint inhibitor as disclosed herein) to a patient. Combination administration may refer to simultaneous administration or may refer to sequential administration of the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, and a checkpoint inhibitor as disclosed herein.

The terms "simultaneous" and "simultaneously" refer to the administration of the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, and a checkpoint inhibitor as disclosed herein, to a patient at the same time, or at two different time points that are separated by no more than 2 hours. The simultaneous administration of the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, and a checkpoint inhibitor may be in a single dosage form or in separate dosage forms.

The terms "sequential" and "sequentially" refer to the administration of the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, and a checkpoint inhibitor as disclosed herein, to a patient at two different time points that are separated by more than 2 hours, e.g., about 3 hours, about 4 hours, about 5 hours, about 8 hours, about 12 hours, 1 day, 2 days, 3 days, 4 days, 5 days, 6 days, 7 days or even longer.

The term "intermission" refers to a period that is subsequent to the administration of one or more particular pharmaceutically active ingredients to a patient in an intermittent regimen. Intermission refers to a rest period wherein a particular pharmaceutically active ingredient is not administered for at least one day.

The term "synergistic effect" refers to a situation where the combination of two or more agents produces a greater effect than the sum of the effects of each of the individual agents. The term encompasses not only a reduction in symptoms of the disorder to be treated, but also an improved side effect profile, improved tolerability, improved patient compliance, improved efficacy, or any other improved clinical outcome.

As used herein, the illustrative terms "include", "such as", "for example" and the like (and variations thereof, e.g., "includes" and "including", "examples"), unless otherwise specified, are intended to be non-limiting. That is, unless explicitly stated otherwise, such terms are intended to imply "but not limited to", e.g., "including" means including but not limited to.

Unless otherwise stated, structures depicted herein are meant to include chemical entities which differ only in the presence of one or more isotopically enriched atoms. For example, chemical entities having the present structure except for the replacement of a hydrogen atom by a deuterium or tritium, or the replacement of a carbon atom by a $^{13}$C- or $^{14}$C-enriched carbon are within the scope of the invention.

Unless stereochemical configuration is denoted, structures depicted herein are meant to include all stereochemical forms of the structure, i.e., the R and S configurations for each asymmetric center. Therefore, unless otherwise indicated, single stereochemical isomers as well as enantiomeric, racemic and diastereomeric mixtures of the present chemical entities are within the scope of the invention. When a stereochemical configuration is denoted for a compound, the diastereoisomeric or enantiomeric excess of the compound is at least 99.0%, 99.5%, 99.6%, 99.7%, 99.8% or 99.9%.

SAE Inhibitor

The present disclosure provides a combination treatment for patients with cancer or autoimmune disease. The combination treatment includes, inter alia, administering to a subject in need thereof a therapeutically effective amount of at least one SAE inhibitor.

In some embodiments, the SAE inhibitor is [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, having the following structure:

Compound I-263a

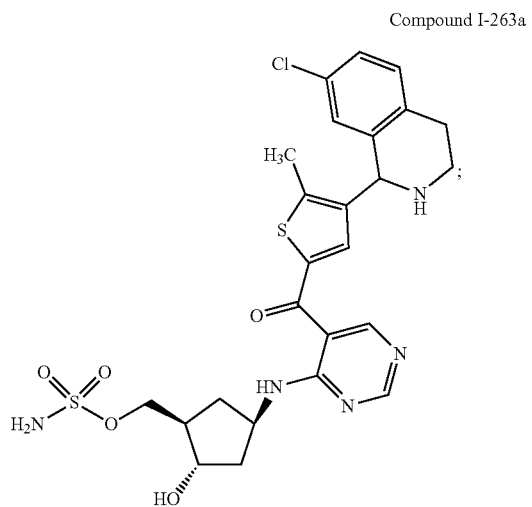 [SMILES: Cc1sc(C(=O)c2cncnc2N[C@@H]2C[C@H](COS(N)(=O)=O)[C@@H](O)C2)cc1C1NCCc2ccc(Cl)cc21]

[(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate is also referred to herein as Compound I-263a.

In some embodiments, the SAE inhibitor is [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof.

In some embodiments, the SAE inhibitor is [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or Compound I-263a.

SAE inhibitors, as disclosed herein, are described, for example, in US 2016/0009744 and U.S. Pat. No. 9,695,154. They may be prepared by methods known to one skilled in the art and/or according to the methods described in US 2016/0009744 and U.S. Pat. No. 9,695,154, which is hereby incorporated by reference in its entirety. Central to the mechanism of action of useful SAE inhibitors, such as Compound I-263a, in combinations and methods of the present disclosure is production of type 1 IFNs and induction of an innate immune response with activation of dendritic cells, natural killer (NK) cells and macrophages. Biochemical assays have demonstrated that Compound I-263a is a mechanism-based inhibitor of SUMO-activating enzyme that potently inhibits enzyme activity by forming a covalent adduct with SUMO. Strong selectivity for SUMO-activating enzyme was observed over the other closely related ubiquitin-activating enzymes, Nedd8-activating enzyme, and autophagy related 7 enzyme. Selective and potent inhibition of SUMO-activating enzyme and SUMOylation by Compound I-263a has been demonstrated in cultured mouse and human tumor cell lines and the antiproliferative activity of Compound I-263a has been determined in a panel of 7 mouse hematologic and solid tumor cell lines.

In some embodiments, the SAE inhibitor is [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a crystalline form thereof.

In some embodiments, the SAE inhibitor or a pharmaceutical salt thereof is crystalline form 1 of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, as described in U.S. published application number US 2016/0009744.

In some embodiments, the SAE inhibitor or a pharmaceutical salt thereof is crystalline form 2 of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, as described in U.S. published application number US 2016/0009744.

In some embodiments, the SAE inhibitor or a pharmaceutical salt thereof is crystalline form 3 of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, described in U.S. published application number US 2016/0009744.

Checkpoint Inhibitors

The present disclosure provides a combination treatment that includes, inter alia, administering to a subject in need thereof a therapeutically effective amount of at least one checkpoint inhibitor (e.g., nivolumab, pembrolizumab, atezolizumab, durvalumab, avelumab, and ipilimumab). In some embodiments, the checkpoint inhibitor is an anti-PD-1 antibody. In some embodiments, the checkpoint inhibitor is an anti-PD-L1 antibody. In some embodiments, the checkpoint inhibitor is an anti-CTLA-4 antibody.

PD-1 is a type I transmembrane protein that is one of the major immune checkpoint molecules (Blanket al., 2005, Cancer Immunotherapy, 54:307-314). PD-1 is primarily expressed on activated T cells, and it interacts with the ligands PD-L1 (B7-H1 or CD274) and PD-L2 (B7-DC or CD273) to induce an inhibitory signal resulting in reduced T cell proliferation, cytokine production, and cytotoxic activity (Freemanetal., 2000, J. Exp. Med., 192:1027-34).

In some embodiments, the anti-PD-1 antibody is a fully human monoclonal antibody. In some embodiments, the anti-PD-1 antibody is a humanized IgG monoclonal antibody.

In some embodiments, the anti-PD-1 antibody is a full length (intact) antibody. In some embodiments, the anti-PD-1 antibody consists of anti-PD-1 binding fragments, including, but not limited to, Fab, Fab', F(ab')$_2$, and Fv fragments, single chain Fv fragments, and single chain domain fragments.

In some embodiments, the anti-PD-1 antibody is a derivatized antibody. In some embodiments, the anti-PD-1 antibody is derivatized by glycosylation, acetylation, pegylation, phosphorylation, and amidation. In some embodiments, the anti-PD-1 antibody is derivatized by known protecting/blocking groups, proteolytic cleavage, linkage to a cellular ligand or other protein. In some embodiments, the derivatized anti-PD-1 antibody can contain one or more non-natural amino acids, e.g., using ambrx technology (See, e.g., Wolfson, 2006, Chem. Biol. 13(10):1011-2).

In some embodiments, the anti-PD-1 antibody is nivolumab.

Nivolumab is a human monoclonal antibody that blocks the interaction between PD-1 and its ligands, PD-L1 and PD-L2. Nivolumab is an IgG4 kappa immunoglobulin that has a calculated molecular mass of 146 kDa. It is expressed in a recombinant Chinese Hamster Ovary (CHO) cell line. Nivolumab is approved by the FDA for treating unresectable or metastatic melanoma, melanoma, metastatic non-small cell lung cancer, advanced renal cell carcinoma, classical Hodgkin lymphoma, squamous cell carcinoma of the head and neck, urothelial carcinoma, microsatellite instability-high (MSI-H) or mismatch repair deficient (dMMR) metastatic colorectal cancer, and hepatocellular carcinoma. Nivolumab is commercially available as Opdivo®.

In some embodiments, the anti-PD-1 antibody is pembrolizumab.

Pembrolizumab is a humanized monoclonal antibody that blocks the interaction between PD-1 and its ligands, PD-L1 and PD-L2. Pembrolizumab is an IgG4 kappa immunoglobulin with an approximate molecular mass of 149 kDa. Pembrolizumab is produced in recombinant Chinese hamster ovary (CHO) cells. Pembrolizumab is approved by the FDA for treating melanoma, non-small cell lung cancer, head and neck cancer, classical Hodgkin lymphoma, primary mediastinal large B-cell lymphoma, urothelial carcinoma, microsatellite instability-high cancer, gastric cancer, and cervical cancer. Pembrolizumab is commercially available as Keytruda®.

In some embodiments, the anti-PD-1 antibody is cemiplimab.

Cemiplimab is a human monoclonal antibody that binds to PD-1 and blocks its interaction with PD-L1 and PD-L2. Cemiplimab is an IgG4 immunoglobulin with an approximate molecular mass of 146 kDa. Cemiplimab is produced by recombinant DNA technology in Chinese hamster ovary (CHO) cell suspension. Cemiplimab is approved by the FDA for treating metastatic cutaneous squamous cell carcinoma (CSCC) or locally advanced CSCC who are not candidates for curative surgery or curative radiation. Cemiplimab is commercially available as Libtayo®.

Additional anti-PD-1 antibodies include, for example, pidilizumab (Medivation), BMS-936559 (Bristol-Myers Squibb), and AMP-224.

In some embodiments, the anti-PD-1 antibody used in the methods (and kits) described herein is nivolumab or an anti-PD-1 antibody that binds to the same epitope as nivolumab. In some embodiments, the anti-PD-1 antibody is nivolumab.

In some embodiments, the anti-PD-1 antibody used in the methods (and kits) described herein is pembrolizumab or an anti-PD-1 antibody that binds to the same epitope as pembrolizumab. In some embodiments, the anti-PD-1 antibody is pembrolizumab.

PD-L1 is a type I transmembrane protein that comprises an extracellular Ig-V like domain, an Ig-C like domain, a transmembrane domain and an intracellular C-terminus domain. PD-L1 is expressed in a broad range of cancers with a high frequency, including tumor cells and/or tumor infiltrating immune cells and can contribute to the inhibition of the anti-tumor immune response in the tumor microenvironment. In some cancers, expression of PD-L1 has been associated with reduced survival and unfavorable prognosis. PD-L1 is expressed on many cell types, including T-cells, B-cells, endothelial, epithelial, and antigen presenting cells, on cells of lung, liver and heart tissues, and on several types of tumor cells. Expression of PD-L1 on the cell surface has also been shown to be upregulated through IFN-y stimulation. There are at least 4 variants of PD-1 that have been cloned from activated human T cells, including transcripts lacking (i) exon 2, (ii) exon 3. (iii) exons 2 and 3 or (iv) exons 2 through 4. Nielsen et al., *Cell. Immunol.* 235: 109-16 (2005). The amino acid sequence of a human PD-L1 is represented in GenBank Accession No. NP 054862.1.

In some embodiments, the anti-PD-L1 antibody is a full length (intact) antibody. In some embodiments, the anti-PD-L1 antibody consists of anti-PD-L1 binding fragments, including, but not limited to, Fab, F(ab')$_2$, Fd, Fv, and dAb fragments, single chain Fv fragments, and PD-L1-binding domain immunoglobulin fusion proteins.

In some embodiments, the anti-PD-L1 antibody is atezolizumab.

Atezolizumab is a programmed cell death ligand 1 (PD-L1) blocking antibody. Atezolizumab is an Fc-engineered, humanized, non-glycosylated IgG1 kappa immunoglobulin that has a calculated molecular mass of 145 kDa. Atezolizumab is approved by the FDA for treating locally advanced or metastatic urothelial carcinoma and metastatic non-small cell lung cancer. Atezolizumab is commercially available as Tecentriq®.

In some embodiments, the anti-PD-L1 antibody is durvalumab.

Durvalumab is a programmed cell death ligand 1 (PD-L1) blocking antibody. Durvalumab is a human immunoglobulin G1 kappa (IgG1κ) monoclonal antibody that is produced by recombinant DNA technology in Chinese Hamster Ovary (CHO) cell suspension culture. Durvalumab is approved by the FDA for treating urothelial carcinoma and non-small cell lung cancer. Durvalumab is commercially available as Imfinzi®.

In some embodiments, the anti-PD-L1 antibody is avelumab.

Avelumab is a programmed death ligand-1 (PD-L1) blocking antibody. Avelumab is a human IgG1 lambda monoclonal antibody that has a molecular weight of approximately 147 kDa. Avelumab is approved by the FDA for treating metastatic Merkel cell carcinoma and locally advanced or metastatic urothelial carcinoma. Avelumab is commercially available as Bavencio®.

Additional anti-PD-L1 antibodies include, for example, YW243.55.S70 (U.S. Pat. No. 8,217,149), MEDI-4736, MSB-0010718C, LY3300054 (Eli Lilly and Co.), BMS-936559 (Bristol-Meyers Squibb), MPDL3280A, and MDX-1105.

In some embodiments, the anti-PD-L1 antibody used in the methods (and kits) described herein is atezolizumab or an anti-PD-L1 antibody that binds to the same epitope as atezolizumab. In some embodiments, the anti-PD-L1 antibody is atezolizumab.

In some embodiments, the anti-PD-L1 antibody used in the methods (and kits) described herein is durvalumab or an anti-PD-L1 antibody that binds to the same epitope as durvalumab. In some embodiments, the anti-PD-L1 antibody is durvalumab.

In some embodiments, the anti-PD-L1 antibody used in the methods (and kits) described herein is avelumab or an anti-PD-L1 antibody that binds to the same epitope as avelumab. In some embodiments, the anti-PD-L1 antibody is avelumab.

CTLA-4 is a Type I transmembrane protein encoded in humans by the CTLA-4 gene. CTLA-4 has been found to have a correlation with cancer growth and development due to its negative role in immune response. CTLA-4 is expressed at the cell surface of activated CD4+ and CD8+ T cells, and is an important negative regulator of T cells function. CTLA-4 has been shown to negatively regulate immune activation through both intrinsic and extrinsic mechanisms (Grosso and Kunkel, Cancer Immunity (2013) 13: 5). Inhibition of negative regulation by CTLA-4 has been shown to promote stimulation of adaptive immune response and T cell activation. A representative amino acid sequence of human CTLA-4 can be found under GenBank accession number: AAL07473.1, and a representative mRNA nucleic acid sequence encoding human CTLA-4 can be found under GenBank accession number: AF414120.1.

In some embodiments, the anti-CTLA-4 antibody is a full length (intact) antibody. In some embodiments, the anti-CTLA-4 antibody consists of anti-CTLA-4 binding fragments, including, but not limited to, Fab, Fab', F(ab')$_2$, Fv, and single chain fragments, a diabody, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody.

In some embodiments, the anti-CTLA-4 antibody is ipilimumab.

Ipilimumab is a recombinant, human monoclonal antibody that binds to the cytotoxic T-lymphocyte-associated antigen 4 (CTLA-4). Ipilimumab is an IgG1 kappa immunoglobulin with an approximate molecular mass of 148 kDa. Ipilimumab is produced in mammalian (Chinese hamster ovary) cell culture. Ipilimumab is approved by the FDA for treating unresectable or metastatic melanoma, adjuvant treatment of melanoma, and advanced renal cell carcinoma. Ipilimumab is commercially available as Yervoy®.

Additional anti-CTLA-4 antibodies include, for example, tremelimumab.

In some embodiments, the anti-CTLA-4 antibody used in the methods (and kits) described herein is ipilimumab or an anti-CTLA-4 antibody that binds to the same epitope as ipilimumab. In some embodiments, the anti-CTLA-4 antibody is ipilimumab.

Methods of Treating Cancer or Autoimmune Disease

In some embodiments, the present disclosure relates to a method of treating cancer in a patient by administering to a patient in need of said treating a combination of an SAE inhibitor or pharmaceutically acceptable salt thereof and one or more checkpoint inhibitors.

In some embodiments, the present disclosure relates to a method of treating cancer by administering to a patient in need of said treating a combination of an SAE inhibitor and a checkpoint inhibitor.

In some embodiments, the present disclosure relates to the use of an SAE inhibitor in combination with a checkpoint inhibitor for the treatment of cancer in a patient.

In some embodiments, the present disclosure relates to a composition comprising an SAE inhibitor for use in treating cancer in a patient, wherein the patient is also treated with a checkpoint inhibitor. In some aspects, the disclosure relates to a composition comprising SAE inhibitor for use in treating cancer in a patient, wherein the SAE inhibitor is in combination with the checkpoint inhibitor. In some embodiments, the SAE inhibitor can be administered simultaneously or sequentially with the checkpoint inhibitor.

In some embodiments, present disclosure relates to a composition comprising Compound I-263a, or a pharmaceutically acceptable salt thereof, and a checkpoint inhibitor, or a pharmaceutically acceptable salt thereof, as a co-formulation or separate formulations, wherein the administration of the formulations is simultaneous, sequential, or in alternation. In some embodiments, the present disclosure provides for the administration of Compound I-263a, or a pharmaceutically acceptable salt thereof, a checkpoint inhibitor, or a pharmaceutically acceptable salt thereof, and one or more additional therapeutic agents, or a pharmaceutically acceptable salt thereof, as a co-formulation or separate formulations, wherein the administration of the formulations is simultaneous, sequential, or in alternation.

In some embodiments, the present disclosure relates to methods of treating cancer comprising administering to a patient in need of such treatment, a therapeutically effective amount of a combination of an SAE inhibitor and a checkpoint inhibitor.

In some embodiments, the present disclosure relates to a method of treating cancer by administering to a patient a combination of Compound I-263a, or pharmaceutically acceptable salt thereof, and a checkpoint inhibitor.

In another aspect, the present disclosure relates to the use of Compound I-263a, or a pharmaceutically acceptable salt thereof, in combination with a checkpoint inhibitor for the treatment of cancer.

In some embodiments, the methods of treating cancer, as described herein, can include a combination of an SAE inhibitor, a checkpoint inhibitor, and one or more additional therapeutic agents. In some embodiments, the one or more additional therapeutic agents can be chemotherapeutic agents. In some embodiments, the one or more additional therapeutic agents can include, but are not limited to, fludarabine, cyclophosphamide, doxorubicin, vincristine, methotrexate anthracycline-based chemotherapeutic agents, prednisone, methylprednisolone, glucocorticoids, Ibritumomab tiuxetan, acetaminophen, antihistamines, and combinations thereof. In another embodiment, the checkpoint inhibitor is coadministered with human hyaluronidase.

In some embodiments, the present disclosure relates to a method of treating a disorder, wherein the disorder is cancer.

In some embodiments, the cancer is a solid tumor. In some embodiments, the solid tumor is an advanced solid tumor. In some embodiments, the solid tumor is a metastatic solid tumor. In some embodiments, the solid tumor is an unresectable solid tumor.

Non-limiting examples of solid tumors include pancreatic cancer; bladder cancer, including invasive bladder cancer; colorectal cancer, including microsatellite instability-high (MSI-H) or mismatch repair deficient (dMMR) metastatic colorectal cancer; microsatellite stable (MSS) colorectal cancer; thyroid cancer; gastric cancer; breast cancer, including metastatic breast cancer; prostate cancer, including androgen-dependent and androgen-independent prostate cancer; renal cancer, including, e.g., metastatic renal cell carcinoma and advanced renal cell carcinoma; urothelial carcinoma, including locally advanced or metastatic urothelial carcinoma; microsatellite instability-high cancer; liver cancer including e.g. hepatocellular carcinoma and intrahepatic bile duct cancer; lung and bronchus cancer including non-small cell lung cancer (NSCLC), NSCLC adenocarcinoma, squamous lung cancer, brochioloalveolar carcinoma (BAC), adenocarcinoma of the lung, and small cell lung cancer (SCLC); ovarian cancer including, e.g., progressive epithelial and primary peritoneal cancer; cervical cancer including CPI-naïve cervical cancer; squamous cell carcinoma; adenosquamous carcinoma; adenocarcinoma of the cervix; uterine cancer including e.g. uterine corpus and uterine cervix; endometrial cancer; esophageal cancer; head and neck cancer, including, e.g., squamous cell carcinoma of the head and neck, nasopharyngeal caner, oral cavity and pharynx; melanoma, including unresectable or metastatic melanoma, and adjuvant treatment of melanoma; metastatic Merkel cell carcinoma; neuroendocrine cancer, including metastatic neuroendocrine tumors; brain cancer, including, e.g., glioma/glioblastoma, anaplastic oligodendroglioma, adult glioblastoma multiforme, and adult anaplastic astrocytoma; neuroendocrine cancer, including metastatic neuroendocrine tumors; bone cancer; gastro-esophageal junction cancer, and soft tissue sarcoma.

In some embodiments, the cancer is a hematological cancer. Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's lymphoma (HL), including classical Hodgkin lymphoma; non-Hodgkin's lymphoma (NHL), including B-cell lymphoma, T-cell lymphoma, follicular lymphoma (FL), marginal zone lymphoma (MZL), mantle cell lymphoma (MCL), diffuse large B-cell lymphoma (DLBCL), primary mediastinal large B-cell lymphoma, and Burkitt lymphoma; multiple myeloma (MM); amyloidosis; Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes. In some embodiments, the cancer is chronic lymphocytic leukemia (CLL), Hodgkin's lymphoma, or non-Hodgkin's lymphoma including follicular lymphoma (FL), marginal zone lymphoma (MZL), mantle cell lymphoma (MCL), Diffuse large B-cell lymphoma (DLBCL) and Burkitt lymphoma.

In some embodiments, the cancer is melanoma, lung cancer, renal cancer, lymphoma, head and neck cancer, urothelial cancer, prostate cancer, bladder cancer, breast cancer, gastric cancer, colorectal cancer, leukemia, cervical cancer, microsatellite instability-high cancer, hepatocellular carcinoma, or Merkel cell carcinoma.

In some embodiments, the melanoma is metastatic melanoma, unresectable melanoma, or cutaneous melanoma.

In some embodiments, the lung cancer is non-small cell lung cancer or small cell lung cancer.

In some embodiments, the non-small cell lung cancer is metastatic non-small cell lung cancer, metastatic squamous non-small cell lung cancer, or metastatic nonsquamous non-small cell lung cancer. In some embodiments, the non-small cell lung cancer is non-small cell lung cancer adenocarcinoma.

In some embodiments, the cancer is cervical cancer. In some embodiments, the cancer is CPI-naïve cervical cancer. In some embodiments, the cancer is squamous cell carcinoma, adenosquamous carcinoma, or adenocarcinoma of the cervix.

In some embodiments the cancer is colorectal cancer. In some embodiments, the cancer is microsatellite stable colorectal cancer (MSS-CRC). In some embodiments, the cancer is CPI-naïve MSS-CRC.

In some embodiments, the renal cancer is renal cell carcinoma.

In some embodiments, the lymphoma is classical Hodgkin lymphoma or primary mediastinal large B-cell lymphoma.

In some embodiments, the head and neck cancer is head and neck squamous cell carcinoma.

In some embodiments, the urothelial cancer is urothelial carcinoma.

In some embodiments, the prostate cancer is hormone-refractory prostate cancer.

In some embodiments, the gastric cancer is gastroesophageal junction adenocarcinoma.

In some embodiments, the cancer is relapsed. In some embodiments, relapsed cancer is cancer which has returned after a period of time in which no cancer could be detected.

In some embodiments, the cancer is refractory. In some embodiments, refractory cancer does not respond to cancer treatment; it is also known as resistant cancer. In some embodiments, the cancer is resistant to rituximab. In some embodiments, the cancer does not respond to the treatment of rituximab. In some embodiments, the cancer is rituximab-resistant recurrent cancer. In some embodiments, the patient has become refractory to a rituximab-containing regimen. In some embodiments, the tumor is unresectable. In some embodiments, an unresectable tumor is unable to be removed by surgery. In some embodiments, the cancer has not been previously treated. In some embodiments, the cancer is locally advanced. In some embodiments, "locally advanced" refers to cancer that is somewhat extensive but still confined to one area. In some instances, "locally advanced" may refer to a small tumor that hasn't spread but has invaded nearby organs or tissues that make it difficult to remove with surgery alone. In some embodiments, the cancer is metastatic. In some embodiments, metastatic cancer is a cancer that has spread from the part of the body where it started (the primary site) to other parts of the body.

In some embodiments, the patient has an advanced metastatic or unresectable solid tumor for which at least one prior treatment regimen has failed.

In some embodiments, the patient has relapsed or refractory PD-1-positive or PD-L1-positive non-small cell lung cancer adenocarcinoma. In some embodiments, the patient has both PD-1-positive non-small cell lung cancer adenocarcinoma and relapsed or refractory non-small cell lung cancer adenocarcinoma. In some embodiments, the patient has both PD-L1-positive non-small cell lung cancer adenocarcinoma and relapsed or refractory non-small cell lung cancer adenocarcinoma.

In some embodiments, the patient has relapsed or refractory PD-1-positive or PD-L1-positive non-small cell lung cancer adenocarcinoma and has progressed on at least one prior treatment regimen.

In some embodiments, the patient has relapsed or refractory PD-1-positive or PD-L1-positive non-small cell lung cancer adenocarcinoma and is refractory to any CPI. In some embodiments, the patient has relapsed or refractory PD-1-positive or PD-L1-positive non-small cell lung cancer adenocarcinoma and has progressed on at least one prior treatment regimen and is refractory to any CPI.

In some embodiments, the patient has relapsed or refractory PD-1-positive CPI-naïve cervical cancer. In some embodiments, the patient has both PD-1-positive CPI-naïve cervical cancer and relapsed or refractory CPI-naïve cervical cancer.

In some embodiments, the patient has relapsed or refractory PD-1-positive CPI-naïve cervical cancer and has progressed on at least one prior treatment regimen.

In some embodiments, the patient has relapsed or refractory PD-1-positive CPI-naïve cervical cancer and is refractory to any CPI. In some embodiments, the patient has relapsed or refractory PD-1-positive CPI-naïve cervical cancer and has progressed on at least one prior treatment regimen and is refractory to any CPI.

In some embodiments, the patient has relapsed or refractory PD-1-positive CPI-naïve microsatellite stable colorectal cancer (MSS-CRC). In some embodiments, the patient has both PD-1-positive CPI-naïve MSS-CRC and relapsed or refractory CPI-naïve MSS-CRC.

In some embodiments, the patient has relapsed or refractory PD-1-positive CPI-naïve MSS-CRC and has progressed on at least one prior treatment regimen. In some embodiments, the patient has relapsed or refractory PD-1-positive CPI-naïve MSS-CRC and has progressed on at least two prior treatment regimens. In some embodiments, the patient has relapsed or refractory PD-1-positive CPI-naïve MSS-CRC and has progressed on three or less prior treatment regimens.

In some embodiments, the patient has relapsed or refractory PD-1-positive CPI-naïve MSS-CRC and is refractory to any CPI. In some embodiments, the patient has relapsed or refractory PD-1-positive CPI-naïve MSS-CRC and has progressed on at least one prior treatment regimen and is refractory to any CPI. In some embodiments, the patient has relapsed or refractory PD-1-positive CPI-naïve MSS-CRC and has progressed on at least two prior treatment regimens and is refractory to any CPI. In some embodiments, the patient has relapsed or refractory PD-1-positive CPI-naïve MSS-CRC and has progressed on three or less prior treatment regimens and is refractory to any CPI.

In some embodiments, the present disclosure relates to a method of treating a disorder, wherein the disorder is an autoimmune disease.

In some embodiments, the disorder is an SAE-mediated disorder. In some embodiments, the disorder is an SAE-mediated disorder other than cancer.

In some embodiments, the disorder is a PD-1-positive cancer. A PD-1-positive cancer includes a cancer where PD-1 is expressed on the cancer cells.

In some embodiments, the PD-1-positive cancer is a PD-1-positive lung cancer. In some embodiments, the PD-1-positive cancer is a PD-1-positive non-small cell lung cancer. In some embodiments, the PD-1-positive cancer is a PD-1-positive metastatic non-small cell lung cancer.

In some embodiments, the PD-1-positive cancer is a PD-1-positive cervical cancer.

In some embodiments, the PD-1-positive cancer is a PD-1-positive colorectal cancer. In some embodiments, the PD-1-positive cancer is a PD-1-positive microsatellite-stable colorectal cancer. In some embodiments, the PD-1-positive cancer is a PD-1-positive microsatellite instability-high (MSI-H) colorectal cancer. In some embodiments, the PD-1-positive cancer is a PD-1-positive mismatch repair deficient (dMMR) metastatic colorectal cancer.

In some embodiments, the PD-1-positive cancer is a PD-1-positive melanoma. In some embodiments, the PD-1-positive cancer is a PD-1-positive unresectable or metastatic melanoma.

In some embodiments, the PD-1-positive cancer is a PD-1-positive renal cancer. In some embodiments, the PD-1-positive cancer is a PD-1-positive advanced renal cell carcinoma.

In some embodiments, the PD-1-positive cancer is a PD-1-positive lymphoma. In some embodiments, the PD-1-positive cancer is a PD-1-positive classical Hodgkin lymphoma.

In some embodiments, the PD-1-positive cancer is a PD-1-positive head and neck cancer. In some embodiments, the PD-1-positive cancer is a PD-1-positive recurrent or metastatic squamous cell carcinoma of the head and neck.

In some embodiments, the PD-1-positive cancer is a PD-1-positive urothelial cancer. In some embodiments, the PD-1-positive cancer is a PD-1-positive advanced or metastatic urothelial carcinoma.

In some embodiments, the PD-1-positive cancer is a PD-1-positive hepatocellular carcinoma.

In some embodiments, the PD-1-positive cancer is a PD-1-positive squamous cell carcinoma. In some embodiments, the PD-1-positive cancer is a PD-1-positive metastatic cutaneous squamous cell carcinoma.

In some embodiments, the disorder is a PD-L1-positive cancer. A PD-L1-positive cancer includes a cancer where PD-L1 is expressed on the cancer cells.

In some embodiments, the PD-L1-positive cancer is a PD-L1-positive lung cancer. In some embodiments, the PD-L1-positive cancer is a PD-L1-positive non-small cell lung cancer. In some embodiments, the PD-L1-positive cancer is a PD-L1-positive metastatic non-small cell lung cancer. In some embodiments, the PD-L1-positive cancer is a PD-L1-positive unresectable Stage III non-small cell lung cancer.

In some embodiments, the PD-L1-positive cancer is a PD-L1-positive urothelial cancer. In some embodiments, the PD-L1-positive cancer is a PD-L1-positive advanced or metastatic urothelial cancer. In some embodiments, the PD-L1-positive cancer is a PD-L1-positive advanced or metastatic urothelial carcinoma.

In some embodiments, the PD-L1-positive cancer is a PD-L1-positive metastatic Merkel cell carcinoma.

In some embodiments, the disorder is a CTLA-4-positive cancer. A CTLA-4-positive cancer includes a cancer where CTLA-4 is expressed on the cancer cells.

In some embodiments, the CTLA-4-positive cancer is a CTLA-4-positive melanoma. In some embodiments, the CTLA-4-positive cancer is a CTLA-4-positive unresectable or metastatic melanoma. In some embodiments, the CTLA-4-positive cancer is a CTLA-4-positive cutaneous melanoma.

In some embodiments, the CTLA-4-positive cancer is a CTLA-4-positive renal cancer. In some embodiments, the CTLA-4-positive cancer is a CTLA-4-positive advanced renal cell carcinoma.

Medicament

In some embodiments, the present disclosure relates to a medicament for use in treating cancer in a patient in need of such treatment. The medicament comprises an SAE inhibitor and a checkpoint inhibitor, and is in single dosage form or in separate dosage forms.

In some embodiments, the medicaments, as described herein, can include a combination of an SAE inhibitor, a checkpoint inhibitor, and optionally one or more additional therapeutic agents.

In some embodiments, the present disclosure relates to the use of an SAE inhibitor in the manufacture of a medicament for treating cancer, wherein the SAE inhibitor is administered with a checkpoint inhibitor, and wherein the medicament is in single dosage form or in separate dosage forms.

In some embodiments, the SAE inhibitor is administered with a checkpoint inhibitor and one or more additional therapeutic agents.

In some embodiments, the present disclosure relates to the use of an SAE inhibitor for the manufacture of a medicament in treating cancer in a patient, wherein the patient is also treated with a checkpoint inhibitor, and optionally one or more additional therapeutic agents. In some embodiments, the SAE inhibitor may be administered simultaneously or sequentially with the checkpoint inhibitor. In some aspects, the present disclosure relates to the use of an SAE inhibitor for the manufacture of a medicament in treating cancer in a patient, wherein the SAE inhibitor is in combination with a checkpoint inhibitor, and optionally one or more additional therapeutic agents. In some embodiments, the SAE inhibitor is in the same composition as the checkpoint inhibitor. In some embodiments, the SAE inhibitor is in a separate composition as the checkpoint inhibitor. In some embodiments, the SAE inhibitor is in the same composition as one or more additional therapeutic agents. In some embodiments, the SAE inhibitor is in the same composition as the checkpoint inhibitor, and optionally one or more additional therapeutic agents. In some embodiments, the SAE inhibitor is in a separate composition as one or more additional therapeutic agents. In some embodiments, the SAE inhibitor is in a separate composition as the checkpoint inhibitor, and optionally one or more additional therapeutic agents.

In another aspect, the present disclosure relates to the use of Compound I-263a, or a pharmaceutically acceptable salt thereof in combination with a checkpoint inhibitor in the manufacture of a medicament for use in treating cancer. In some embodiments, the present disclosure relates to the use of Compound I-263a, or a pharmaceutically acceptable salt thereof in combination with a checkpoint inhibitor, and optionally one or more additional therapeutic agents in the manufacture of a medicament for use in treating cancer.

In another aspect, the present disclosure relates to the use of Compound I-263a, or a pharmaceutically acceptable salt thereof, in the manufacture of a medicament for treating cancer, wherein Compound I-263a or a pharmaceutically acceptable salt thereof is administered with a checkpoint inhibitor, and optionally one or more additional therapeutic agents.

In another aspect, the present disclosure relates to Compound I-263a, or a pharmaceutically acceptable salt thereof, for use as a medicament in combination with a checkpoint inhibitor, wherein Compound I-263a and the checkpoint inhibitor may be administered simultaneously or sequentially.

In another aspect, the present disclosure relates to the use of Compound I-263a, or a pharmaceutically acceptable salt thereof, and a checkpoint inhibitor, in the manufacture of a medicament for the treatment of cancer in a subject. In some embodiments, the present disclosure relates to the use of Compound I-263a, or a pharmaceutically acceptable salt thereof, and a checkpoint inhibitor, in the manufacture of a medicament for the treatment of cancer in a subject, wherein Compound I-263a is formulated to be administrable simultaneously or sequentially to the subject with an additional therapeutic agent. In some embodiments, the present disclosure relates to the use of Compound I-263a, or a pharmaceutically acceptable salt thereof, and a checkpoint inhibitor, in the manufacture of a medicament for the treatment of cancer in a subject, wherein Compound I-263a and the checkpoint inhibitor are formulated to be administrable simultaneously or sequentially to the subject with an additional therapeutic agent.

In some embodiments, the one or more additional therapeutic agents can be chemotherapeutic agents. In some embodiments, the one or more additional therapeutic agents can include, but are not limited to, fludarabine, cyclophosphamide, doxorubicin, vincristine, methotrexate anthracycline-based chemotherapeutic agents, prednisone, methylprednisolone, glucocorticoids, Ibritumomab tiuxetan, acetaminophen, antihistamines, and combinations thereof. In another embodiment, the checkpoint inhibitor is coadministered with human hyaluronidase.

Administration of the Combination

Compound I-263a or a pharmaceutically acceptable salt thereof, may be administered in combination with the checkpoint inhibitor, and optionally one or more additional therapeutic agents, in a single dosage form or as a separate dosage forms. In some embodiments, when administered as a separate dosage form, the checkpoint inhibitor may be administered prior to, at the same time as, or following administration of I-263a or a pharmaceutically acceptable salt thereof. In some embodiments, when administered as a separate dosage form, one or more doses of I-263a or a pharmaceutically acceptable salt thereof, may be administered prior to the checkpoint inhibitor. In some embodiments, the checkpoint inhibitor is administered prior to the administration of Compound I-263a or a pharmaceutically acceptable salt thereof. As used herein, the administration in "combination" of Compound I-263a or a pharmaceutically acceptable salt thereof, a checkpoint inhibitor, and optionally one or more additional therapeutic agents refers not only to simultaneous or sequential administration of the agents, but also to the administration of the agents during a single treatment cycle, as understood by one skilled in the art. When Compound I-263a or a pharmaceutically acceptable salt thereof is administered in combination with the checkpoint inhibitor, and optionally one or more additional therapeutic agents, a therapeutically effective amount of the combination is administered.

The SAE inhibitor may be administered by any method known to one skilled in the art. For example, in some embodiments, the SAE inhibitor may be administered in the form of a pharmaceutical composition of the SAE inhibitor and a pharmaceutically acceptable carrier, such as those described herein. In some embodiments, the pharmaceutical composition is suitable for oral administration. In some embodiments, the pharmaceutical composition is a tablet or a capsule that is suitable for oral administration. In some other embodiments, the pharmaceutical composition is a liquid dosage form suitable for oral administration. In some embodiments, the pharmaceutical composition is suitable for parenteral administration. In some embodiments, the pharmaceutical composition is suitable for intravenous administration. In some embodiments, the pharmaceutical composition is suitable for intravenous infusion. In some embodiments, the pharmaceutical composition is suitable for injection. In some embodiments, the pharmaceutical composition is suitable for intravenous injection. In some embodiments, the pharmaceutical composition is suitable for subcutaneous injection. In some embodiments, these compositions optionally further comprise one or more additional therapeutic agents.

The checkpoint inhibitor may be administered by any method known to one skilled in the art. In some embodiments, the checkpoint inhibitor is administered intravenously (i.v.). In some embodiments, the checkpoint inhibitor is administered subcutaneously (s.c.). In some embodiments, the checkpoint inhibitor is administered orally. For example, the checkpoint inhibitor may be administered in the form of a second composition, in some embodiments, a pharmaceutical composition of the checkpoint inhibitor and a pharmaceutically acceptable carrier, such as those described herein. In some aspects, the pharmaceutical composition is suitable for oral administration. In some embodiments, the pharmaceutical composition is a tablet or a capsule that is suitable for oral administration. In some other embodiments, the pharmaceutical composition is a liquid dosage form suitable for oral administration. In some embodiments, these compositions optionally further comprise one or more additional therapeutic agents.

In some embodiments, the checkpoint inhibitor may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. In some embodiments, the checkpoint inhibitor is administered orally, intravenously or subcutaneously. In some embodiments, the checkpoint inhibitor is administered orally. In some embodiments, the checkpoint inhibitor is administered intravenously. In some embodiments, the intravenous administration can be intravenous infusion or intravenous injection. In some embodiments, the checkpoint inhibitor is administered by an intravenous infusion. In some embodiments, the checkpoint inhibitor is administered by an intravenous injection. In some embodiments, the checkpoint inhibitor is administered by subcutaneous injection. In some embodiments, the checkpoint inhibitor is administered by intravenous infusion and then subsequently administered by subcutaneous injection. In another embodiment, the checkpoint inhibitor is coadministered with human hyaluronidase subcutaneously. These methods of administration may be designed to be short-acting, fast-releasing, or long-acting. Furthermore, the checkpoint inhibitor may be administered in a local rather than systemic means, such as administration (e.g., by injection) at a tumor site.

In some embodiments, each therapeutic agent in the combination disclosed herein (e.g., Compound I-263a and a checkpoint inhibitor) can be administered by the same route or by different routes. For example, a first therapeutic agent of the combination may be administered by intravenous injection while the other therapeutic agent or agents of the combination may be administered orally. Alternatively, for example, all therapeutic agents may be administered orally or all therapeutic agents may be administered by intravenous injection. Therapeutic agents may also be administered in alternation.

In some embodiments, the checkpoint inhibitor may also be administered by nasal aerosol or inhalation. The checkpoint inhibitor may be prepared according to techniques well known in the art and may be prepared as solutions in saline, employing benzyl alcohol or other suitable preservatives, absorption promoters to enhance bioavailability, fluorocarbons, and/or other conventional solubilizing or dispersing agents.

The amounts or suitable doses of the methods of this disclosure depends upon a number of factors, including the nature of the severity of the condition to be treated, the particular inhibitor, the route of administration and the age, weight, general health, and response of the individual patient. In some embodiments, the suitable dose level is one that achieves a therapeutic response as measured by tumor regression, or other standard measures of disease progression, progression free survival or overall survival. In some embodiments, the suitable dose level is one that achieves this therapeutic response and also minimizes any side effects associated with the administration of the therapeutic agent. The suitable dose levels may be ones that prolong the therapeutic response and/or prolong life.

It will be understood that a suitable dose of the SAE inhibitor, the checkpoint inhibitor, and optionally one or more additional therapeutic agents may be taken at any time of the day or night. In some embodiments, a suitable dose of each agent is taken in the morning. In some other embodiments, a suitable dose of each agent is taken in the evening. In some embodiments, a suitable dose of each of the agents is taken both in the morning and the evening. It will be understood that a suitable dose of each agent may be taken with or without food. In some embodiments a suitable dose of an agent is taken with a meal. In some embodiments a suitable dose of an agent is taken while fasting.

In some embodiments, Compound I-263a or a pharmaceutically acceptable salt thereof is administered on a daily schedule. In some embodiments, Compound I-263a or a pharmaceutically acceptable salt thereof is administered every other day. In some embodiments, Compound I-263a or a pharmaceutically acceptable salt thereof is administered once every three days. In some embodiments, Compound I-263a or a pharmaceutically acceptable salt thereof is administered on a twice-weekly schedule. In some embodiments, Compound I-263a or a pharmaceutically acceptable salt thereof is administered on a three times a week schedule. In some embodiments, Compound I-263a or a pharmaceutically acceptable salt thereof is administered on a weekly schedule. In some embodiments, Compound I-263a or a pharmaceutically acceptable salt thereof is administered on a once every two weeks schedule.

In some embodiments, Compound I-263a or a pharmaceutically acceptable salt thereof is administered at least 3 times on alternate days within a 7-day cycle. In some embodiments, Compound I-263a or a pharmaceutically acceptable salt thereof is administered on day 1 and day 4 of a 7-day cycle. In some embodiments, Compound I-263a or a pharmaceutically acceptable salt thereof is administered on consecutive days in a 7-day cycle followed by an intermission. In some embodiments, Compound I-263a or a pharmaceutically acceptable salt thereof is administered for 2 consecutive days followed by an intermission of 5 consecutive days for at least one 7-day cycle. In some embodiments, Compound I-263a or a pharmaceutically acceptable salt thereof is administered for 3 consecutive days followed by an intermission of 4 consecutive days for at least one 7-day cycle. In some embodiments, Compound I-263a or a pharmaceutically acceptable salt thereof is administered for 4 consecutive days followed by an intermission of 3 consecutive days for at least one 7-day cycle. In some embodiments, Compound I-263a or a pharmaceutically acceptable salt thereof is administered for 5 consecutive days followed by an intermission of 2 consecutive days for at least one 7-day cycle. In some embodiments, there will be periods of rest between one or more of the 7-day treatment cycles. In some embodiments, there will be a 7-day rest between one or more of the 7-day treatment cycles.

The present description contemplates administration of the SAE inhibitor for one or more treatment cycles, for example, 1, 2, 3, 4, 5, 6, or more, treatment cycles. In some embodiments, a treatment cycle is about 7 days to about 56 days, or more. In some embodiments, a treatment cycle is 7 days, 14 days, 21 days, 28 days, 35 days, 42 days, 49 days, or 56 days. In some embodiments, a treatment cycle is 21 days or 28 days. In some embodiments, there will be periods of rest within or between one or more of the treatment cycles. For example, in some embodiments, there will be a period of rest at the end of the treatment cycle. In some embodiments, there will be a period of rest between the second and third treatment cycle but not the first and second treatment cycle. In another embodiment, there might be a period of rest between the first and second treatment cycle but not the second and third treatment cycle. Dosing schedules include, for example, administering the SAE inhibitor once during a treatment schedule, e.g., on day 1 of a 21 day cycle, twice during a treatment cycle, e.g., on days 1 and 15 of a 21 day cycle or on days 1 and 15 of a 28 day cycle, three times during a treatment cycle, e.g., on days 1, 8 and 15 of a 21 day cycle or on days 1, 8 and 15 of a 28 day cycle, and four times during a treatment cycle, e.g., on days 1, 4, 8, and 11 of a 21 day cycle or of on days 1, 4, 8, and 11 of a 28 day cycle. Other dosage schedules are encompassed by the present invention.

In some embodiments, Compound I-263a or a pharmaceutically acceptable salt thereof is administered within a 21-day cycle. In some embodiments, Compound I-263a or a pharmaceutically acceptable salt thereof is administered at least two times within a 21-day cycle. In some embodiments, Compound I-263a or a pharmaceutically acceptable salt thereof is administered at least four times within a 21-day cycle. In some embodiments, Compound I-263a or a pharmaceutically acceptable salt thereof is administered on day 1 within a 21-day cycle. In some embodiments, Compound I-263a or a pharmaceutically acceptable salt thereof is administered on day 4 within a 21-day cycle. In some embodiments, Compound I-263a or a pharmaceutically acceptable salt thereof is administered on day 8 within a 21-day cycle. In some embodiments, Compound I-263a or a pharmaceutically acceptable salt thereof is administered on day 11 within a 21-day cycle. In some embodiments, Compound I-263a or a pharmaceutically acceptable salt thereof is administered on days 1, 4, 8, and 11 within a 21-day cycle.

In some embodiments, Compound I-263a or a pharmaceutically acceptable salt thereof is administered for a duration of 1 year or less. In some embodiments, Compound I-263a or a pharmaceutically acceptable salt thereof is administered for a duration of 1 year or more. In some embodiments, Compound I-263a or a pharmaceutically acceptable salt thereof is administered for a duration of 24 months or less. In some embodiments, Compound I-263a or a pharmaceutically acceptable salt thereof is administered for a duration of 24 months or more.

In some embodiments, Compound I-263a or a pharmaceutically acceptable salt thereof is administered once a week. In some embodiments, Compound I-263a or a pharmaceutically acceptable salt thereof is administered once a week for two weeks. In some embodiments, Compound I-263a or a pharmaceutically acceptable salt thereof is administered once a week for two weeks within a 21-day cycle.

In some embodiments, the amount of Compound I-263a or a pharmaceutically acceptable salt thereof that is administered on each day of dosing is about 0.5 mg to about 200 mg. In some embodiments, the amount of Compound I-263a or a pharmaceutically acceptable salt thereof that is administered on each day of dosing is about 0.5 mg to about 100 mg. In some embodiments, the amount of Compound I-263a or a pharmaceutically acceptable salt thereof that is administered on each day of dosing is about 0.5 mg to about 50 mg. In some embodiments, the amount of Compound I-263a or a pharmaceutically acceptable salt thereof that is administered on each day of dosing is about 0.5 mg to about 10 mg. In some embodiments, the amount of Compound I-263a or a pharmaceutically acceptable salt thereof that is administered on each day of dosing is about 0.5 mg to about 5 mg. In some embodiments, the amount of Compound I-263a or a pharmaceutically acceptable salt thereof that is administered on each day of dosing is about 1 mg to about 3 mg. In some embodiments, the amount of Compound I-263a or a pharmaceutically acceptable salt thereof that is administered on each day of dosing is about 2 mg to about 5 mg. In some embodiments, the amount of Compound I-263a or a pharmaceutically acceptable salt thereof that is administered on each day of dosing is about 5 mg to about 10 mg. In some embodiments, the amount of Compound I-263a or a pharmaceutically acceptable salt thereof that is administered on each day of dosing is about 5 mg to about 15 mg. In some embodiments, the amount of Compound I-263a or a pharmaceutically acceptable salt thereof that is administered on each day of dosing is about 10 mg to about 20 mg. In some embodiments, the amount of Compound I-263a or a pharmaceutically acceptable salt thereof that is administered on each day of dosing is about 15 mg to about 25 mg. In some embodiments, the amount of Compound I-263a or a pharmaceutically acceptable salt thereof that is administered on each day of dosing is between about 20 mg to about 30 mg. In some embodiments, the amount of Compound I-263a or a pharmaceutically acceptable salt thereof that is administered on each day of dosing is between about 25 mg to about 35 mg. In some embodiments, the amount of Compound I-263a or a pharmaceutically acceptable salt thereof that is administered on each day of dosing is between about 30 mg to about 40 mg. In some embodiments, the amount of Compound I-263a or a pharmaceutically acceptable salt thereof that is administered on each day of dosing is between about 35 mg to about 45 mg. In some embodiments, the amount of Compound I-263a or a pharmaceutically acceptable salt thereof that is administered on each day of dosing is between about 40 mg to about 50 mg. In some embodiments, the amount of Compound I-263a or a pharmaceutically acceptable salt thereof that is administered on each day of dosing is between about 55 mg to about 65 mg. In some embodiments, the amount of Compound I-263a or a pharmaceutically acceptable salt thereof that is administered on each day of dosing is between about 50 mg to about 100 mg. In some embodiments, the amount of Compound I-263a or a pharmaceutically acceptable salt thereof that is administered on each day of dosing is between about 90 mg to about 150 mg. In some embodiments, the amount of Compound I-263a or a pharmaceutically acceptable salt thereof that is administered on each day of dosing is between about 140 mg to about 200 mg. In some embodiments, the amount of Compound I-263a or a pharmaceutically acceptable salt thereof that is administered on each day of dosing is about 0.5 mg. In some embodiments, the amount of Compound I-263a or a pharmaceutically acceptable salt thereof that is administered on each day of dosing is about 1 mg. In some embodiments, the amount of Compound I-263a or a pharmaceutically acceptable salt thereof that is administered on each day of dosing is about 2 mg. In some embodiments, the amount of Compound I-263a or a pharmaceutically acceptable salt thereof that is administered on each day of dosing is about 3 mg. In some embodiments, the amount of Compound I-263a or a pharmaceutically acceptable salt thereof that is administered on each day of dosing is about 4 mg. In some embodiments, the amount of Compound I-263a or a pharmaceutically acceptable salt thereof that is administered on each day of dosing is about 6 mg. In some embodiments, the amount of Compound I-263a or a pharmaceutically acceptable salt thereof that is administered on each day of dosing is about 8 mg. In some embodiments, the amount of Compound I-263a or a pharmaceutically acceptable salt thereof that is administered on each day of dosing is about 10 mg. In some embodiments, the amount of Compound I-263a or a pharmaceutically acceptable salt thereof that is administered on each day of dosing is about 12 mg. All dosing amounts refer to the amount of Compound I-263a administered, and do not include the weight amount of any pharmaceutically acceptable salt.

In some embodiments, the amount of Compound I-263a or a pharmaceutically acceptable salt thereof that is administered on each day of dosing is about 1 mg. In some embodiments, the amount of Compound I-263a or a pharmaceutically acceptable salt thereof that is administered on each day of dosing is about 3 mg. In some embodiments, the amount of Compound I-263a or a pharmaceutically acceptable salt thereof that is administered on each day of dosing is about 6 mg. In some embodiments, the amount of Compound I-263a or a pharmaceutically acceptable salt thereof that is administered on each day of dosing is about 10 mg. In some embodiments, the amount of Compound I-263a or a pharmaceutically acceptable salt thereof that is administered on each day of dosing is about 15 mg. In some embodiments, the amount of Compound I-263a or a pharmaceutically acceptable salt thereof that is administered on each day of dosing is about 25 mg. In some embodiments, the amount of Compound I-263a or a pharmaceutically acceptable salt thereof that is administered on each day of dosing is about 40 mg. In some embodiments, the amount of Compound I-263a or a pharmaceutically acceptable salt thereof that is administered on each day of dosing is about 60 mg. In some embodiments, the amount of Compound I-263a or a pharmaceutically acceptable salt thereof that is administered on each day of dosing is about 90 mg. In some embodiments, the amount of Compound I-263a or a pharmaceutically acceptable salt thereof that is administered on each day of dosing is about 120 mg. In some embodiments, the amount of Compound I-263a or a pharmaceutically acceptable salt thereof that is administered on each day of dosing is about 160 mg.

In some embodiments, the Compound I-263a or a pharmaceutically acceptable salt thereof is administered as an intravenous (IV) infusion. In some embodiments, the Compound I-263a or a pharmaceutically acceptable salt thereof is administered as a 60±10 minute IV infusion. In some embodiments, the Compound I-263a or a pharmaceutically acceptable salt thereof is administered as a 300 minute or less IV infusion. In some embodiments, the Compound I-263a or a pharmaceutically acceptable salt thereof is administered as a 60 minute to 300 minute IV infusion.

In some embodiments, the checkpoint inhibitor is administered on a daily schedule. In some embodiments, the checkpoint inhibitor is administered every other day. In some embodiments, the checkpoint inhibitor is administered once every three days. In some embodiments, the checkpoint inhibitor is administered on a twice-weekly schedule. In some embodiments, the checkpoint inhibitor is administered on a three times a week schedule. In some embodiments, the checkpoint inhibitor is administered on a weekly schedule. In some embodiments, the checkpoint inhibitor is administered on a once every two weeks schedule. In some embodiments, the checkpoint inhibitor is administered on a once every three weeks schedule. In some embodiments, the checkpoint inhibitor is administered on a once every four weeks schedule. In some embodiments, the checkpoint inhibitor is administered on a once every eight weeks schedule. In some embodiments, the checkpoint inhibitor is administered on a once every twelve weeks schedule.

In some embodiments, the checkpoint inhibitor is administered at least 3 times on alternate days within a 7-day cycle. In some embodiments, the checkpoint inhibitor is administered on day 1 of a treatment cycle. In some embodiments, the checkpoint inhibitor is administered on day 1 and day 4 of a 7-day cycle. In some embodiments, the checkpoint inhibitor is administered on consecutive days in a 7-day cycle followed by an intermission. In some embodiments, the checkpoint inhibitor is administered for 2 consecutive days followed by an intermission of 5 consecutive days for at least one 7-day cycle. In some embodiments, the checkpoint inhibitor is administered for 3 consecutive days followed by an intermission of 4 consecutive days for at least one 7-day cycle. In some embodiments, the checkpoint inhibitor is administered for 4 consecutive days followed by an intermission of 3 consecutive days for at least one 7-day cycle. In some embodiments, the checkpoint inhibitor is administered for 5 consecutive days followed by an intermission of 2 consecutive days for at least one 7-day cycle.

The present description contemplates administration of the checkpoint inhibitor for one or more treatment cycles, for example, 1, 2, 3, 4, 5, 6, or more, treatment cycles. In some embodiments, a treatment cycle is about 7 days to about 84 days, or more. In some embodiments, a treatment cycle is 7 days, 14 days, 21 days, 28 days, 35 days, 42 days, 49 days, 56 days, or 84 days. In some embodiments, a treatment cycle is 21 days or 28 days. In some embodiments, there will be periods of rest within or between one or more of the treatment cycles. For example, in some embodiments, there will be a period of rest at the end of the treatment cycle. In some embodiments, there will be a period of rest between the second and third treatment cycle but not the first and second treatment cycle. In another embodiment, there might be a period of rest between the first and second treatment cycle but not the second and third treatment cycle. Dosing schedules include, for example, administering the checkpoint inhibitor once during a treatment schedule, e.g., on day 1 of a 21 day cycle, twice during a treatment cycle, e.g., on days 1 and 15 of a 21 day cycle or on days 1 and 15 of a 28 day cycle, three times during a treatment cycle, e.g., on days 1, 8 and 15 of a 21 day cycle or on days 1, 8 and 15 of a 28 day cycle, and four times during a treatment cycle, e.g., on days 1, 4, 8, and 11 of a 21 day cycle or of on days 1, 4, 8, and 11 of a 28 day cycle. Other dosage schedules are encompassed by the present invention.

In some embodiments, the checkpoint inhibitor is administered as an intravenous (IV) infusion. In some embodiments, the checkpoint inhibitor is administered as a 30±10 minute IV infusion.

In some embodiments, the checkpoint inhibitor is administered within a 21-day cycle. In some embodiments, the checkpoint inhibitor is administered on day 1 of a 21-day cycle.

In some embodiments, Compound I-263a or a pharmaceutically acceptable salt thereof is administered on the same day as the checkpoint inhibitor. In some embodiments, Compound I-263a or a pharmaceutically acceptable salt thereof is administered before the checkpoint inhibitor when both are administered on the same day. In some embodiments, the checkpoint inhibitor is administered before Compound I-263a or a pharmaceutically acceptable salt thereof when both are administered on the same day.

In some embodiments, the dose of Compound I-263a or a pharmaceutically acceptable salt thereof is delayed from 1 to 3 days within a 21-day cycle. In some embodiments, the dose of the checkpoint inhibitor is delayed from 1 to 3 days within a 21-day cycle. In some embodiments, the dose of both Compound I-263a or a pharmaceutically acceptable salt thereof and the checkpoint inhibitor are delayed from 1 to 3 days within a 21-day cycle.

In some embodiments, the checkpoint inhibitor is administered by subcutaneous injection. In some embodiments, the checkpoint inhibitor is administered by intravenous infusion followed by one or more subsequent subcutaneous injections. In some embodiments, the intravenous infusion and one or more subsequent subcutaneous injections are administered according to the dosing schedules and methods disclosed herein.

In some embodiments, the amount of the anti-PD-1 antibody that is administered on each day of dosing is about 0.5 mg to about 1000 mg. In some embodiments, the amount of the anti-PD-1 antibody that is administered on each day of dosing is about 0.5 mg to about 900 mg. In some embodiments, the amount of the anti-PD-1 antibody that is administered on each day of dosing is about 0.5 mg to about 800 mg. In some embodiments, the amount of the anti-PD-1 antibody that is administered on each day of dosing is about 0.5 mg to about 700 mg. In some embodiments, the amount of the anti-PD-1 antibody that is administered on each day of dosing is about 0.5 mg to about 600 mg. In some embodiments, the amount of the anti-PD-1 antibody that is administered on each day of dosing is about 0.5 mg to about 500 mg. In some embodiments, the amount of the anti-PD-1 antibody that is administered on each day of dosing is about 1 mg to about 500 mg. In some embodiments, the amount of the anti-PD-1 antibody that is administered on each day of dosing is about 10 mg to about 500 mg. In some embodiments, the amount of the anti-PD-1 antibody that is administered on each day of dosing is about 50 mg to about 500 mg. In some embodiments, the amount of the anti-PD-1 antibody that is administered on each day of dosing is about 100 mg to about 500 mg. In some embodiments, the amount of the anti-PD-1 antibody that is administered on each day of dosing is about 150 mg to about 500 mg. In some embodiments, the amount of the anti-PD-1 antibody that is administered on each day of dosing is about 200 mg to about 500 mg. In some embodiments, the amount of the anti-PD-1 antibody that is administered on each day of dosing is about 220 mg to about 500 mg. In some embodiments, the amount of the anti-PD-1 antibody that is administered on each day of dosing is about 240 mg to about 500 mg. In some embodiments, the amount of the anti-PD-1 antibody that is administered on each day of dosing is about 260 mg to about 500 mg. In some embodiments, the amount of the anti-PD-1 antibody that is administered on each day of dosing is about 280 mg to about 500 mg. In some embodiments, the amount of the anti-PD-1 antibody that is administered on each day of dosing is about 300 mg to about 500 mg. In some embodiments, the amount of the anti-PD-1 antibody that is administered on each day of dosing is about 320 mg to about 500 mg. In some embodiments, the amount of the anti-PD-1 antibody that is administered on each day of dosing is about 340 mg to about 500 mg. In some embodiments, the amount of the anti-PD-1 antibody that is administered on each day of dosing is about 360 mg to about 500 mg. In some embodiments, the amount of the anti-PD-1 antibody that is administered on each day of dosing is about 380 mg to about 500 mg. In some embodiments, the amount of the anti-PD-1 antibody that is administered on each day of dosing is about 400 mg to about 500 mg. In some embodiments, the amount of the anti-PD-1 antibody that is administered on each day of dosing is about 200 mg to about 480 mg. In some embodiments, the amount of the anti-PD-1 antibody that is administered on each day of dosing is about 200 mg to about 460 mg. In some embodiments, the amount of the anti-PD-1 antibody that is administered on each day of dosing is about 200 mg to about 440 mg. In some embodiments, the amount of the anti-PD-1 antibody that is administered on each day of dosing is about 200 mg to about 420 mg. In some embodiments, the amount of the anti-PD-1 antibody that is administered on each day of dosing is about 200 mg to about 400 mg. In some embodiments, the amount of the anti-PD-1 antibody that is administered on each day of dosing is about 200 mg to about 380 mg. In some embodiments, the amount of the anti-PD-1 antibody that is administered on each day of dosing is about 200 mg to about 360 mg. In some embodiments, the amount of the anti-PD-1 antibody that is administered on each day of dosing is about 200 mg to about 340 mg. In some embodiments, the amount of the anti-PD-1 antibody that is administered on each day of dosing is about 200 mg to about 320 mg. In some embodiments, the amount of the anti-PD-1 antibody that is administered on each day of dosing is about 200 mg to about 300 mg.

In some embodiments, the amount of the anti-PD-1 antibody that is administered on each day of dosing is about 100 mg. In some embodiments, the amount of the anti-PD-1 antibody that is administered on each day of dosing is about 120 mg. In some embodiments, the amount of the anti-PD-1 antibody that is administered on each day of dosing is about 140 mg. In some embodiments, the amount of the anti-PD-1 antibody that is administered on each day of dosing is about 160 mg. In some embodiments, the amount of the anti-PD-1 antibody that is administered on each day of dosing is about 180 mg. In some embodiments, the amount of the anti-PD-1 antibody that is administered on each day of dosing is about 200 mg. In some embodiments, the amount of the anti-PD-1 antibody that is administered on each day of dosing is about 220 mg. In some embodiments, the amount of the anti-PD-1 antibody that is administered on each day of dosing is about 240 mg. In some embodiments, the amount of the anti-PD-1 antibody that is administered on each day of dosing is about 260 mg. In some embodiments, the amount of the anti-PD-1 antibody that is administered on each day of dosing is about 280 mg. In some embodiments, the amount of the anti-PD-1 antibody that is administered on each day of dosing is about 300 mg. In some embodiments, the amount of the anti-PD-1 antibody that is administered on each day of dosing is about 320 mg. In some embodiments, the amount of the anti-PD-1 antibody that is administered on each day of dosing is about 340 mg. In some embodiments, the amount of the anti-PD-1 antibody that is administered on each day of dosing is about 360 mg. In some embodiments, the amount of the anti-PD-1 antibody that is administered on each day of dosing is about 380 mg. In some embodiments, the amount of the anti-PD-1 antibody that is administered on each day of dosing is about 400 mg. In some embodiments, the amount of the anti-PD-1 antibody that is administered on each day of dosing is about 420 mg. In some embodiments, the amount of the anti-PD-1 antibody that is administered on each day of dosing is about 440 mg. In some embodiments, the amount of the anti-PD-1 antibody that is administered on each day of dosing is about 460 mg. In some embodiments, the amount of the anti-PD-1 antibody that is administered on each day of dosing is about 480 mg. In some embodiments, the amount of the anti-PD-1 antibody that is administered on each day of dosing is about 500 mg. In some embodiments, the amount of the anti-PD-1 antibody that is administered on each day of dosing is about 600 mg. In some embodiments, the amount of the anti-PD-1 antibody that is administered on each day of dosing is about 700 mg. In some embodiments, the amount of the anti-PD-1 antibody that is administered on each day of dosing is about 800 mg. In some embodiments, the amount of the anti-PD-1 antibody that is administered on each day of dosing is about 900 mg. In some embodiments, the amount of the anti-PD-1 antibody that is administered on each day of dosing is about 1000 mg.

In some embodiments, the amount of the anti-PD-1 antibody that is administered on each day of dosing is about 0.5 mg/kg to about 10 mg/kg. In some embodiments, the amount of the anti-PD-1 antibody that is administered on each day of dosing is about 0.5 mg/kg to about 7.5 mg/kg. In some embodiments, the amount of the anti-PD-1 antibody that is administered on each day of dosing is about 0.5 mg/kg to about 5 mg/kg. In some embodiments, the amount of the anti-PD-1 antibody that is administered on each day of dosing is about 1 mg/kg to about 4 mg/kg. In some embodiments, the amount of the anti-PD-1 antibody that is administered on each day of dosing is about 1 mg/kg to about 3 mg/kg. In some embodiments, the amount of the anti-PD-1 antibody that is administered on each day of dosing is about 0.5 mg/kg. In some embodiments, the amount of the anti-PD-1 antibody that is administered on each day of dosing is about 1 mg/kg. In some embodiments, the amount of the anti-PD-1 antibody that is administered on each day of dosing is about 1.5 mg/kg. In some embodiments, the amount of the anti-PD-1 antibody that is administered on each day of dosing is about 2 mg/kg. In some embodiments, the amount of the anti-PD-1 antibody that is administered on each day of dosing is about 2.5 mg/kg. In some embodiments, the amount of the anti-PD-1 antibody that is administered on each day of dosing is about 3 mg/kg. In some embodiments, the amount of the anti-PD-1 antibody that is administered on each day of dosing is about 3.5 mg/kg. In some embodiments, the amount of the anti-PD-1 antibody that is administered on each day of dosing is about 4 mg/kg. In some embodiments, the amount of the anti-PD-1 antibody that is administered on each day of dosing is about 4.5 mg/kg. In some embodiments, the amount of the anti-PD-1 antibody that is administered on each day of dosing is about 5 mg/kg. In some embodiments, the amount of the anti-PD-1 antibody that is administered on each day of dosing is about 7.5 mg/kg. In some embodiments, the amount of the anti-PD-1 antibody that is administered on each day of dosing is about 10 mg/kg.

In some embodiments, the anti-PD-1 antibody is nivolumab, or a pharmaceutically acceptable salt thereof. In some embodiments, the anti-PD-1 antibody is pembrolizumab, or a pharmaceutically acceptable salt thereof. In some embodiments, the anti-PD-1 antibody is cemiplimab, or a pharmaceutically acceptable salt thereof.

In some embodiments, the administration of nivolumab, pembrolizumab, and cemiplimab is in accordance with its prescribing information as approved by the health authorities, such as those issued by the FDA, or the EMA, which are incorporated here by their entirety.

In some embodiments, the amount of the anti-PD-L1 antibody that is administered on each day of dosing is about 0.5 mg to about 2000 mg. In some embodiments, the amount of the anti-PD-L1 antibody that is administered on each day of dosing is about 0.5 mg to about 1800 mg. In some embodiments, the amount of the anti-PD-L1 antibody that is administered on each day of dosing is about 0.5 mg to about 1600 mg. In some embodiments, the amount of the anti-PD-L1 antibody that is administered on each day of dosing is about 0.5 mg to about 1400 mg. In some embodiments, the amount of the anti-PD-L1 antibody that is administered on each day of dosing is about 0.5 mg to about 1200 mg. In some embodiments, the amount of the anti-PD-L1 antibody that is administered on each day of dosing is about 0.5 mg to about 1000 mg. In some embodiments, the amount of the anti-PD-L1 antibody that is administered on each day of dosing is about 1 mg to about 2000 mg. In some embodiments, the amount of the anti-PD-L1 antibody that is administered on each day of dosing is about 10 mg to about 2000 mg. In some embodiments, the amount of the anti-PD-L1 antibody that is administered on each day of dosing is about 100 mg to about 2000 mg. In some embodiments, the amount of the anti-PD-L1 antibody that is administered on each day of dosing is about 200 mg to about 2000 mg. In some embodiments, the amount of the anti-PD-L1 antibody that is administered on each day of dosing is about 400 mg to about 2000 mg. In some embodiments, the amount of the anti-PD-L1 antibody that is administered on each day of dosing is about 600 mg to about 2000 mg. In some embodiments, the amount of the anti-PD-L1 antibody that is administered on each day of dosing is about 800 mg to about 2000 mg. In some embodiments, the amount of the anti-PD-L1 antibody that is administered on each day of dosing is about 1000 mg to about 2000 mg. In some embodiments, the amount of the anti-PD-L1 antibody that is administered on each day of dosing is about 1200 mg to about 2000 mg. In some embodiments, the amount of the anti-PD-L1 antibody that is administered on each day of dosing is about 1500 mg to about 2000 mg. In some embodiments, the amount of the anti-PD-L1 antibody that is administered on each day of dosing is about 1000 mg to about 2000 mg. In some embodiments, the amount of the anti-PD-L1 antibody that is administered on each day of dosing is about 1000 mg to about 1800 mg. In some embodiments, the amount of the anti-PD-L1 antibody that is administered on each day of dosing is about 1000 mg to about 1600 mg. In some embodiments, the amount of the anti-PD-L1 antibody that is administered on each day of dosing is about 1000 mg to about 1400 mg. In some embodiments, the amount of the anti-PD-L1 antibody that is administered on each day of dosing is about 1000 mg to about 1200 mg. In some embodiments, the amount of the anti-PD-L1 antibody that is administered on each day of dosing is about 1200 mg to about 1400 mg. In some embodiments, the amount of the anti-PD-L1 antibody that is administered on each day of dosing is about 1100 mg to about 1300 mg. In some embodiments, the amount of the anti-PD-L1 antibody that is administered on each day of dosing is about 1100 mg to about 1200 mg. In some embodiments, the amount of the anti-PD-L1 antibody that is administered on each day of dosing is about 1200 mg to about 1300 mg.

In some embodiments, the amount of the anti-PD-L1 antibody that is administered on each day of dosing is about 100 mg. In some embodiments, the amount of the anti-PD-L1 antibody that is administered on each day of dosing is about 200 mg. In some embodiments, the amount of the anti-PD-L1 antibody that is administered on each day of dosing is about 300 mg. In some embodiments, the amount of the anti-PD-L1 antibody that is administered on each day of dosing is about 400 mg. In some embodiments, the amount of the anti-PD-L1 antibody that is administered on each day of dosing is about 500 mg. In some embodiments, the amount of the anti-PD-L1 antibody that is administered on each day of dosing is about 600 mg. In some embodiments, the amount of the anti-PD-L1 antibody that is administered on each day of dosing is about 700 mg. In some embodiments, the amount of the anti-PD-L1 antibody that is administered on each day of dosing is about 800 mg. In some embodiments, the amount of the anti-PD-L1 antibody that is administered on each day of dosing is about 900 mg. In some embodiments, the amount of the anti-PD-L1 antibody that is administered on each day of dosing is about 1000 mg. In some embodiments, the amount of the anti-PD-L1 antibody that is administered on each day of dosing is about 1100 mg. In some embodiments, the amount of the anti-PD-L1 antibody that is administered on each day of dosing is about 1200 mg. In some embodiments, the amount of the anti-PD-L1 antibody that is administered on each day of dosing is about 1300 mg. In some embodiments, the amount of the anti-PD-L1 antibody that is administered on each day of dosing is about 1400 mg. In some embodiments, the amount of the anti-PD-L1 antibody that is administered on each day of dosing is about 1500 mg. In some embodiments, the amount of the anti-PD-L1 antibody that is administered on each day of dosing is about 1600 mg. In some embodiments, the amount of the anti-PD-L1 antibody that is administered on each day of dosing is about 1700 mg. In some embodiments, the amount of the anti-PD-L1 antibody that is administered on each day of dosing is about 1800 mg. In some embodiments, the amount of the anti-PD-L1 antibody that is administered on each day of dosing is about 1900 mg. In some embodiments, the amount of the anti-PD-L1 antibody that is administered on each day of dosing is about 2000 mg. In some embodiments, the amount of the anti-PD-L1 antibody that is administered on each day of dosing is about 2500 mg. In some embodiments, the amount of the anti-PD-L1 antibody that is administered on each day of dosing is about 3000 mg.

In some embodiments, the amount of the anti-PD-L1 antibody that is administered on each day of dosing is about 0.5 mg/kg to about 20 mg/kg. In some embodiments, the amount of the anti-PD-L1 antibody that is administered on each day of dosing is about 1 mg/kg to about 20 mg/kg. In some embodiments, the amount of the anti-PD-L1 antibody that is administered on each day of dosing is about 5 mg/kg to about 20 mg/kg. In some embodiments, the amount of the anti-PD-L1 antibody that is administered on each day of dosing is about 5 mg/kg to about 15 mg/kg. In some embodiments, the amount of the anti-PD-L1 antibody that is administered on each day of dosing is about 5 mg/kg to about 10 mg/kg. In some embodiments, the amount of the anti-PD-L1 antibody that is administered on each day of dosing is about 6 mg/kg to about 10 mg/kg. In some embodiments, the amount of the anti-PD-L1 antibody that is administered on each day of dosing is about 7 mg/kg to about 10 mg/kg. In some embodiments, the amount of the anti-PD-L1 antibody that is administered on each day of dosing is about 8 mg/kg to about 10 mg/kg. In some embodiments, the amount of the anti-PD-L1 antibody that is administered on each day of dosing is about 9 mg/kg to about 10 mg/kg. In some embodiments, the amount of the anti-PD-L1 antibody that is administered on each day of dosing is about 10 mg/kg to about 15 mg/kg. In some embodiments, the amount of the anti-PD-L1 antibody that is administered on each day of dosing is about 10 mg/kg to about 14 mg/kg. In some embodiments, the amount of the anti-PD-L1 antibody that is administered on each day of dosing is about 10 mg/kg to about 13 mg/kg. In some embodiments, the amount of the anti-PD-L1 antibody that is administered on each day of dosing is about 10 mg/kg to about 12 mg/kg. In some embodiments, the amount of the anti-PD-L1 antibody that is administered on each day of dosing is about 10 mg/kg to about 11 mg/kg. In some embodiments, the amount of the anti-PD-L1 antibody that is administered on each day of dosing is about 1 mg/kg. In some embodiments, the amount of the anti-PD-L1 antibody that is administered on each day of dosing is about 2 mg/kg. In some embodiments, the amount of the anti-PD-L1 antibody that is administered on each day of dosing is about 3 mg/kg. In some embodiments, the amount of the anti-PD-L1 antibody that is administered on each day of dosing is about 4 mg/kg. In some embodiments, the amount of the anti-PD-L1 antibody that is administered on each day of dosing is about 5 mg/kg. In some embodiments, the amount of the anti-PD-L1 antibody that is administered on each day of dosing is about 6 mg/kg. In some embodiments, the amount of the anti-PD-L1 antibody that is administered on each day of dosing is about 7 mg/kg. In some embodiments, the amount of the anti-PD-L1 antibody that is administered on each day of dosing is about 8 mg/kg. In some embodiments, the amount of the anti-PD-L1 antibody that is administered on each day of dosing is about 9 mg/kg. In some embodiments, the amount of the anti-PD-L1 antibody that is administered on each day of dosing is about 10 mg/kg. In some embodiments, the amount of the anti-PD-L1 antibody that is administered on each day of dosing is about 11 mg/kg. In some embodiments, the amount of the anti-PD-L1 antibody that is administered on each day of dosing is about 12 mg/kg. In some embodiments, the amount of the anti-PD-L1 antibody that is administered on each day of dosing is about 13 mg/kg. In some embodiments, the amount of the anti-PD-L1 antibody that is administered on each day of dosing is about 14 mg/kg. In some embodiments, the amount of the anti-PD-L1 antibody that is administered on each day of dosing is about 15 mg/kg. In some embodiments, the amount of the anti-PD-L1 antibody that is administered on each day of dosing is about 16 mg/kg. In some embodiments, the amount of the anti-PD-L1 antibody that is administered on each day of dosing is about 17 mg/kg. In some embodiments, the amount of the anti-PD-L1 antibody that is administered on each day of dosing is about 18 mg/kg. In some embodiments, the amount of the anti-PD-L1 antibody that is administered on each day of dosing is about 19 mg/kg. In some embodiments, the amount of the anti-PD-L1 antibody that is administered on each day of dosing is about 20 mg/kg.

In some embodiments, the anti-PD-L1 antibody is atezolizumab, or a pharmaceutically acceptable salt thereof. In some embodiments, the anti-PD-L1 antibody is durvalumab, or a pharmaceutically acceptable salt thereof. In some embodiments, the anti-PD-L1 antibody is avelumab, or a pharmaceutically acceptable salt thereof.

In some embodiments, the administration of atezolizumab, durvalumab, and avelumab is in accordance with its prescribing information as approved by the health authorities, such as those issued by the FDA, or the EMA, which are incorporated here by their entirety.

In some embodiments, the amount of the anti-CTLA-4 antibody that is administered on each day of dosing is about 0.5 mg to about 2000 mg. In some embodiments, the amount of the anti-CTLA-4 antibody that is administered on each day of dosing is about 1 mg to about 2000 mg. In some embodiments, the amount of the anti-CTLA-4 antibody that is administered on each day of dosing is about 10 mg to about 2000 mg. In some embodiments, the amount of the anti-CTLA-4 antibody that is administered on each day of dosing is about 50 mg to about 2000 mg. In some embodiments, the amount of the anti-CTLA-4 antibody that is administered on each day of dosing is about 100 mg to about 2000 mg. In some embodiments, the amount of the anti-CTLA-4 antibody that is administered on each day of dosing is about 1 mg. In some embodiments, the amount of the anti-CTLA-4 antibody that is administered on each day of dosing is about 10 mg. In some embodiments, the amount of the anti-CTLA-4 antibody that is administered on each day of dosing is about 100 mg. In some embodiments, the amount of the anti-CTLA-4 antibody that is administered on each day of dosing is about 200 mg. In some embodiments, the amount of the anti-CTLA-4 antibody that is administered on each day of dosing is about 400 mg. In some embodiments, the amount of the anti-CTLA-4 antibody that is administered on each day of dosing is about 600 mg. In some embodiments, the amount of the anti-CTLA-4 antibody that is administered on each day of dosing is about 800 mg. In some embodiments, the amount of the anti-CTLA-4 antibody that is administered on each day of dosing is about 1000 mg. In some embodiments, the amount of the anti-CTLA-4 antibody that is administered on each day of dosing is about 1200 mg. In some embodiments, the amount of the anti-CTLA-4 antibody that is administered on each day of dosing is about 1400 mg. In some embodiments, the amount of the anti-CTLA-4 antibody that is administered on each day of dosing is about 1600 mg. In some embodiments, the amount of the anti-CTLA-4 antibody that is administered on each day of dosing is about 1800 mg. In some embodiments, the amount of the anti-CTLA-4 antibody that is administered on each day of dosing is about 2000 mg.

In some embodiments, the amount of the anti-CTLA-4 antibody that is administered on each day of dosing is about 0.5 mg/kg to about 20 mg/kg. In some embodiments, the amount of the anti-CTLA-4 antibody that is administered on each day of dosing is about 1 mg/kg to about 20 mg/kg. In some embodiments, the amount of the anti-CTLA-4 antibody that is administered on each day of dosing is about 1 mg/kg to about 18 mg/kg. In some embodiments, the amount of the anti-CTLA-4 antibody that is administered on each day of dosing is about 1 mg/kg to about 16 mg/kg. In some embodiments, the amount of the anti-CTLA-4 antibody that is administered on each day of dosing is about 1 mg/kg to about 14 mg/kg. In some embodiments, the amount of the anti-CTLA-4 antibody that is administered on each day of dosing is about 1 mg/kg to about 12 mg/kg. In some embodiments, the amount of the anti-CTLA-4 antibody that is administered on each day of dosing is about 1 mg/kg to about 10 mg/kg. In some embodiments, the amount of the anti-CTLA-4 antibody that is administered on each day of dosing is about 1 mg/kg. In some embodiments, the amount of the anti-CTLA-4 antibody that is administered on each day of dosing is about 2 mg/kg. In some embodiments, the amount of the anti-CTLA-4 antibody that is administered on each day of dosing is about 3 mg/kg. In some embodiments, the amount of the anti-CTLA-4 antibody that is administered on each day of dosing is about 4 mg/kg. In some embodiments, the amount of the anti-CTLA-4 antibody that is administered on each day of dosing is about 5 mg/kg. In some embodiments, the amount of the anti-CTLA-4 antibody that is administered on each day of dosing is about 6 mg/kg. In some embodiments, the amount of the anti-CTLA-4 antibody that is administered on each day of dosing is about 7 mg/kg. In some embodiments, the amount of the anti-CTLA-4 antibody that is administered on each day of dosing is about 8 mg/kg. In some embodiments, the amount of the anti-CTLA-4 antibody that is administered on each day of dosing is about 9 mg/kg. In some embodiments, the amount of the anti-CTLA-4 antibody that is administered on each day of dosing is about 10 mg/kg. In some embodiments, the amount of the anti-CTLA-4 antibody that is administered on each day of dosing is about 11 mg/kg. In some embodiments, the amount of the anti-CTLA-4 antibody that is administered on each day of dosing is about 12 mg/kg. In some embodiments, the amount of the anti-CTLA-4 antibody that is administered on each day of dosing is about 13 mg/kg. In some embodiments, the amount of the anti-CTLA-4 antibody that is administered on each day of dosing is about 14 mg/kg. In some embodiments, the amount of the anti-CTLA-4 antibody that is administered on each day of dosing is about 15 mg/kg. In some embodiments, the amount of the anti-CTLA-4 antibody that is administered on each day of dosing is about 16 mg/kg. In some embodiments, the amount of the anti-CTLA-4 antibody that is administered on each day of dosing is about 17 mg/kg. In some embodiments, the amount of the anti-CTLA-4 antibody that is administered on each day of dosing is about 18 mg/kg. In some embodiments, the amount of the anti-CTLA-4 antibody that is administered on each day of dosing is about 19 mg/kg. In some embodiments, the amount of the anti-CTLA-4 antibody that is administered on each day of dosing is about 20 mg/kg.

In some embodiments, the anti-CTLA-4 antibody is ipilimumab, or a pharmaceutically acceptable salt thereof.

In some embodiments, the administration of ipilimumab is in accordance with its prescribing information as approved by the health authorities, such as those issued by the FDA, or the EMA, which are incorporated here by their entirety.

Pharmaceutical Compositions

The SAE inhibitors and the checkpoint inhibitors used in the methods and kits described herein can be formulated into pharmaceutical compositions suitable for administration. The pharmaceutical compositions may comprise pharmaceutically acceptable excipients. A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21$^{st}$ Ed., A. R. Gennaro (Lippincott, Williams & Wilkins, Baltimore, MD), 2006; incorporated by reference in its entirety)

Any of the therapeutic agents described herein may be in the form of a pharmaceutically acceptable salt. In some embodiments, such salts are derived from inorganic or organic acids or bases. For reviews of suitable salts, see, e.g., Berge et al., *J. Pharm. Sci.,* 1977, 66, 1-19 and *Remington: The Science and Practice of Pharmacy,* 20th Ed., A. Gennaro (ed.), Lippincott Williams & Wilkins (2000).

Examples of suitable acid addition salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts; alkali metal salts, such as sodium and potassium salts; alkaline earth metal salts, such as calcium and magnesium salts; salts with organic bases, such as dicyclohexylamine salts, N-methyl-D-glucamine; and salts with amino acids such as arginine, lysine, and the like.

For example, Berge lists the following FDA-approved commercially marketed salts: anions acetate, besylate (benzenesulfonate), benzoate, bicarbonate, bitartrate, bromide, calcium edetate (ethylenediaminetetraacetate), camsylate (camphorsulfonate), carbonate, chloride, citrate, dihydrochloride, edetate (ethylenediaminetetraacetate), edisylate (1,2-ethanedisulfonate), estolate (lauryl sulfate), esylate (ethanesulfonate), fumarate, gluceptate (glucoheptonate), gluconate, glutamate, glycollylarsanilate (glycollamidophenylarsonate), hexylresorcinate, hydrabamine (N,N'-di(dehydroabietyl)-ethylenediamine), hydrobromide, hydrochloride, hydroxynaphthoate, iodide, isethionate (2-hydroxyethanesulfonate), lactate, lactobionate, malate, maleate, mandelate, mesylate (methanesulfonate), methylbromide, methylnitrate, methylsulfate, mucate, napsylate (2-naphthalenesulfonate), nitrate, pamoate (embonate), pantothenate, phosphate/diphosphate, polygalacturonate, salicylate, stearate, subacetate, succinate, sulfate, tannate, tartrate, teoclate (8-chlorotheophyllinate) and triethiodide; organic cations benzathine (N,N'-dibenzylethylenediamine), chloroprocaine, choline, diethanolamine, ethylenediamine, meglumine (N-methylglucamine) and procaine; and metallic cations aluminum, calcium, lithium, magnesium, potassium, sodium and zinc.

Berge additionally lists the following non-FDA-approved commercially marketed (outside the United States) salts: anions adipate, alginate, aminosalicylate, anhydromethylenecitrate, arecoline, aspartate, bisulfate, butylbromide, camphorate, digluconate, dihydrobromide, disuccinate, glycerophosphate, hemisulfate, hydrofluoride, hydroiodide, methylenebis(salicylate), napadisylate (1,5-naphthalenedisulfonate), oxalate, pectinate, persulfate, phenylethylbarbiturate, picrate, propionate, thiocyanate, tosylate and undecanoate; organic cations benethamine (N-benzylphenethylamine), clemizole (1-p-chloro-benzyl-2-pyrrolildine-1'-ylmethylbenzimidazole), diethylamine, piperazine and tromethamine (tris(hydroxymethyl)aminomethane); and metallic cations barium and bismuth.

The pharmaceutical compositions may comprise pharmaceutically acceptable carriers. As used herein, "pharmaceutically acceptable carrier" refers to a material that is compatible with a recipient subject (a human) and is suitable for delivering an active agent to the target site without terminating the activity of the agent. The toxicity or adverse effects, if any, associated with the carrier preferably are commensurate with a reasonable risk/benefit ratio for the intended use of the active agent.

Pharmaceutically acceptable carriers that may be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions for use in the methods of the present disclosure may be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may contain stabilizers, pH modifiers, surfactants, solubilizing agents, bioavailability modifiers and combinations of these. These pharmaceutical compositions are formulated for pharmaceutical administration to a human being. Such compositions may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. In some embodiments, the compositions are administered orally, intravenously or subcutaneously. In some embodiments, the compositions are administered orally. In some embodiments, the compositions are administered intravenously. In some embodiments, the intravenous administration can be intravenous infusion or intravenous injection. In some embodiments, the compositions are administered by an intravenous infusion. In some embodiments, the compositions are administered by an intravenous injection. In some embodiments, the compositions are administered by subcutaneous injection. In some embodiments, the compositions are administered by intravenous infusion and then subsequently administered by subcutaneous injection. In another embodiment, the checkpoint inhibitor is coadministered with human hyaluronidase subcutaneously. These formulations may be designed to be short-acting, fast-releasing, or long-acting. Furthermore, the compositions may be administered in a local rather than systemic means, such as administration (e.g., by injection) at a tumor site.

Pharmaceutical formulations may be prepared as liquid suspensions or solutions using a liquid, such as an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol; ethers, such as poly(ethyleneglycol); petroleum hydrocarbons such as mineral oil and petrolatum; and water.

Sterile injectable forms of these pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as sorbitan alkyl esters, such as Tweens or Spans, and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

These pharmaceutical compositions may be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents may also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes, e.g., to mask taste, to affect the site of dissolution or absorption, or to prolong drug action. Coatings may be applied to a tablet or to granulated particles for use in a capsule.

Alternatively, these pharmaceutical compositions may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

These pharmaceutical compositions may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of the present disclosure include mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active component(s) suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, a compound of formula I-263a is formulated as a solution for intravenous infusion. In some embodiments, a compound of formula I-263a is formulated in a solution with a buffering agent or a PH modifying agent, and a cyclodextrin, such as a beta-cyclodextrin. In some embodiments, the solution includes phosphoric acid and Captisol (betadex sulfobutyl ether sodium) in water. In some embodiments, the solution for intravenous infusion contains 10 mg/mL of a compound of formula I-263a.

In some embodiments, a compound of formula I-263a is formulated as a drug product, wherein the drug product contains Compound I-263a in a solution of phosphoric acid and Captisol (betadex sulfobutyl ether sodium) in water. In some embodiments, the drug product is packaged with a volume of 10 mL of Compound I-263a sterile solution.

In some embodiments, the checkpoint inhibitor is formulated as a solution for injection containing 100 mg/4 mL of the checkpoint inhibitor. In some embodiments, the checkpoint inhibitor is formulated as a powder for solution for infusion containing 50 mg of the checkpoint inhibitor. In some embodiments, the checkpoint inhibitor is Pembrolizumab.

In another aspect, the present disclosure relates to a pharmaceutical composition for use in treating or preventing cancer in a subject in need thereof comprising Compound I-263a, or a pharmaceutically acceptable salt thereof, and a checkpoint inhibitor. In some embodiments, the present disclosure relates to a pharmaceutical composition for use in treating or preventing cancer in a subject in need thereof comprising Compound 1-263a, or a pharmaceutically acceptable salt thereof, and a checkpoint inhibitor and one or more additional therapeutic agents. In some embodiments, the pharmaceutical composition is formulated for simultaneous or sequential administration of said Compound I-263a, or a pharmaceutically acceptable salt thereof, and said one or more additional therapeutic agents. In some embodiments, the pharmaceutical composition is formulated for simultaneous or sequential administration of said Compound I-263a, or a pharmaceutically acceptable salt thereof, said checkpoint inhibitor, and said one or more additional therapeutic agents.

Kits

In some embodiments, the SAE inhibitor or the checkpoint inhibitor described herein may be manufactured for inclusion in a kit. A "kit" is any article of manufacture (e.g., a package or container) comprising at least one reagent or chemotherapeutic agent. A kit for use in the methods herein may comprise an SAE inhibitor, such as a compound of formula I-263a or a pharmaceutically acceptable salt thereof. In some embodiments, the kit may further include a checkpoint inhibitor, and optionally one or more additional therapeutic agents. In some embodiments, the kit may include a compound of formula I-263a or a pharmaceutically acceptable salt thereof, a checkpoint inhibitor, and optionally one or more additional therapeutic agents. In some embodiments, the kit may include one or more SAE inhibitors or pharmaceutically acceptable salts thereof. In some embodiments, the kit may include one or more checkpoint inhibitors.

In some embodiments, the present disclosure relates to a kit comprising a medicament for use in treating cancer in a patient in need of such treatment. The kit comprises a medicament comprising an SAE inhibitor, and instructions for administering the SAE inhibitor and a checkpoint inhibitor; or the kit comprises a medicament comprising a checkpoint inhibitor, and instructions for administering the checkpoint inhibitor and an SAE inhibitor. The kit may contain a medicament comprising an SAE inhibitor and a checkpoint inhibitor, and instructions for administering the SAE inhibitor and the checkpoint inhibitor, wherein the medicament is in single dosage form or in separate dosage forms. In some embodiments, the kit optionally comprises one or more additional therapeutic agents.

In some embodiments, a kit comprising an SAE inhibitor and a checkpoint inhibitor may further include another component or reagent. In some embodiments, a reagent in the kit may be a diluent for preparing the SAE inhibitor for administration. In some embodiments, a reagent in the kit may be a diluent for preparing the checkpoint inhibitor for administration. In some embodiments, a component in the kit may be a vessel for mixing the combination of the SAE inhibitor and the checkpoint inhibitor.

In another aspect, the present disclosure relates to a kit for treating cancer comprising at least one medicament comprising at least one dose of Compound I-263a or a pharmaceutically acceptable salt thereof, and at least one medicament comprising at least one dose of a checkpoint inhibitor, said kit for treating cancer further comprising dosing instructions for administering the medicaments for treatment of the patient in recognized need thereof.

In order that this present disclosure be more fully understood, the following examples are set forth. These examples are illustrative only and are not intended to limit the scope of the present disclosure in any way.

EXAMPLES

Abbreviations

H hour
Min minutes
HPLC High-pressure liquid chromatography
UPLC Ultra-pressure liquid chromatography
NMR Nuclear Magnetic Resonance
THE tetrahydrofuran
WFI Water for Injection
TGI tumor growth inhibition
Mg milligram
$mm^3$ cubic millimeter
HPbCD 2-hydroxypropyl-β-cyclodextrin
CMC carboxymethylcellulose
PO oral
SC subcutaneously
SD starting day
IV intravenous
DLT dose limiting toxicity
PK pharmacokinetic
TEAE treatment-emergent adverse events
DL dose level
C1D1 cycle one, day one
ORR overall response rate
CR complete response
PR partial response
DCR disease control rate
DOR duration of response
TTP time to progression
PFS progression free survival
OS overall survival
CPI checkpoint inhibitor
CRC colorectal cancer
MSS-CRC microsatellite stable colorectal cancer
NSCLC non-small cell lung cancer
CTCAE Common Terminology Criteria for Adverse Events
BOIN Bayesian Optimal Interval
RECIST Response Evaluation Criteria in Solid Tumors
iRECIST Response Evaluation Criteria in Solid Tumors for immune-based therapeutics
RP2D recommended phase 2 dose Example 1: In Vivo Tumor Efficacy General Analytical Methods Unless otherwise stated $^1$H NMR spectra were obtained using a Varian 300 MHz. Unless otherwise stated HPLC were obtained on Agilent 1100 Series and UPLC were obtained by Water Acuity Systems.

Compound I-263a, as used in the Examples below, can be synthesized according to the procedures recited in Example 201 in PCT publication number WO 2016/004136.

General Experimental Conditions for Anti-Tumor Efficacy in Mouse Tumor Models

Mouse Syngeneic Tumor Models

The following syngeneic models were utilized in each of Studies 1-8, as specified below.

CT26 Study 1: CT26 is a mouse colon fibroblast carcinoma cell line. CT26 mouse syngeneic tumor model was generated by subcutaneous inoculation with $0.2\times10^6$ CT-26 cells (cell suspension) in 12 weeks old female BALB/c mice (Jackson Laboratory, 600 Main St, Bar Harbor, ME) in the flank. When the mean tumor volume reached approximately 60 $mm^3$, the animals were randomized into one vehicle control and three treatment groups (n=8/group). Mice were then dosed with 20% HPbCD or Compound I-263a or anti-mouse PD-1 antibody over a 14-day period. Tumor growth and body weight were measured twice per week during the treatment and post-treatment periods, and mice were humanely euthanized once they had reached their humane endpoint.

CT26 Study 2: CT26 is a mouse colon fibroblast carcinoma cell line. CT26 mouse syngeneic tumor model was generated by subcutaneous inoculation with $0.2\times10^6$ CT-26 cells (cell suspension) in 10 weeks old female BALB/c mice (Vital River Laboratory Animal Technology Co., Ltd., Beijing, China) in the flank. When the mean tumor volume reached approximately 40 $mm^3$, the animals were randomized into one vehicle control and three treatment groups (n=9/group). Mice were then dosed with 20% HPbCD or Compound I-263a or anti-mouse PD-1 antibody over a 14-day period. Tumor growth and body weight were measured twice per week during the treatment and post-treatment periods, and mice were humanely euthanized once they had reached their humane endpoint.

A20 Study 3: A20 is a mouse B-cell lymphoma cell line. A20 mouse syngeneic tumor model was generated by subcutaneous inoculation with $1.0\times10^6$ A20 cells (cell suspension) in 8 weeks old female BALB/c mice (Jackson Laboratory, 600 Main St, Bar Harbor, ME) in the flank. When the mean tumor volume reached approximately 50 $mm^3$, the animals were randomized into one vehicle control and three treatment groups (n=7/group). Mice were then dosed with 20% HPbCD or Compound I-263a or anti-mouse PD-1 antibody over a 11-day period. Tumor growth and body weight were measured twice per week during the treatment and post-treatment periods, and mice were humanely euthanized once they had reached their humane endpoint.

WEHI-3 Study 4: WEHI-3 is a mouse myelomonocytic leukemia cell line. WEHI-3 mouse syngeneic tumor model was generated by subcutaneous inoculation with $0.1 \times 10^6$ WEHI-3 cells (cell suspension) in 13 weeks old female BALB/c mice (Jackson Laboratory, 600 Main St, Bar Harbor, ME) in the flank. When the mean tumor volume reached approximately 50 mm$^3$, the animals were randomized into one vehicle control and five treatment groups (n=8/group). Mice were then dosed with 20% HPbCD or Compound I-263a or anti-mouse PD-1 antibody or anti-mouse CTLA-4 antibody over a 21-day period. Tumor growth and body weight were measured twice per week during the treatment and post-treatment periods, and mice were humanely euthanized once they had reached their humane endpoint.

WEHI-3 Study 5: WEHI-3 is a mouse myelomonocytic leukemia cell line. WEHI-3 mouse syngeneic tumor model was generated by subcutaneous inoculation with $0.1 \times 10^6$ WEHI-3 cells (cell suspension) in 9 weeks old female BALB/c mice (SINO-British SIPPR/BK Lab Animal Ltd. Shanghai, China) in the flank. When the mean tumor volume reached approximately 30 mm$^3$, the animals were randomized into one vehicle control and five treatment groups (n=8/group). Mice were then dosed with 20% HPbCD or Compound I-263a or anti-mouse PD-1 antibody or anti-mouse CTLA-4 antibody over a 21-day period. Tumor growth and body weight were measured twice per week during the treatment and post-treatment periods, and mice were humanely euthanized once they had reached their humane endpoint.

JC Study 6: JC is a mouse breast adenocarcinoma cell line. JC mouse syngeneic tumor model was generated by subcutaneous inoculation with $0.2 \times 10^6$ JC cells (cell suspension) in 10 weeks old female BALB/c mice (Vital River Laboratory Animal Technology Co., Ltd., Beijing, China) in the flank. When the mean tumor volume reached approximately 45 mm$^3$, the animals were randomized into one vehicle control and five treatment groups (n=8/group). Mice were then dosed with 20% HPbCD or Compound I-263a or anti-mouse PD-1 antibody over a 21-day period. Tumor growth and body weight were measured twice per week during the treatment and post-treatment periods, and mice were humanely euthanized once they had reached their humane endpoint.

B16-F10 Study 7: B16-F10 is a mouse melanoma cell line. B16-F10 mouse syngeneic tumor model was generated by subcutaneous inoculation with $0.08 \times 10^6$ B16-F10 cells (cell suspension) in 11 weeks old female C57BL/6 mice (Taconic Biosciences, Rensselaer, NY) in the flank. When the mean tumor volume reached approximately 50 mm$^3$, the animals were randomized into one vehicle control and five treatment groups (n=8/group). Mice were then dosed with 20% HPbCD or Compound I-263a or anti-mouse PD-1 antibody over a 17-day period. Tumor growth and body weight were measured twice per week during the treatment and post-treatment periods, and mice were humanely euthanized once they had reached their humane endpoint.

MC38 Study 8: MC38 is a mouse colon adenocarcinoma cell line. MC38 mouse syngeneic tumor model was generated by subcutaneous inoculation with $1.0 \times 10^6$ MC38 cells (cell suspension) in 11 weeks old female C57BL/6 mice (SINO-British SIPPR/BK Lab Animal Ltd., Shanghai, China) in the flank. When the mean tumor volume reached approximately 60 mm$^3$, the animals were randomized into one vehicle control and five treatment groups (n=8/group). Mice were then dosed with 20% HPbCD or Compound I-263a or anti-mouse PD-1 antibody over a 21-day period. Tumor growth and body weight were measured twice per week during the treatment and post-treatment periods, and mice were humanely euthanized once they had reached their humane endpoint.

Test Agents

The following test agents were utilized in each of Studies 1-8, as specified below.

Study 1: A 0.825 mg/mL stock solution of Compound I-263a was formulated weekly in 20% HPβCD and administered intravenously (IV) based on exact animal body weight on each day of treatment, using a dosing volume of 10 mL/kg body weight. Final doses received were 7.5 mg/kg. Dosing volume for Compound I-263a was 0.2 mL. Anti-mouse PD1 antibody (anti-mPD-1) (Bio X Cell, 10 Technology Drive, Suite 2B, West Lebanon, NH 03784) was formulated prior to each injection at 2.2 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Compound I-263a was administered on a BIW schedule for 1 week (Day 1 and 4), and anti-mPD-1 administered on a BIW schedule for 2 weeks (Day 1, 4, 8, and 11).

Study 2: A 0.75 mg/mL stock solution of Compound I-263a was formulated weekly in 20% HPβCD and administered intravenously (IV) based on exact animal body weight on each day of treatment, using a dosing volume of 10 mL/kg body weight. Final doses received were 7.5 mg/kg. Dosing volume for Compound I-263a was 0.2 mL. Anti-mouse PD1 antibody (anti-mPD-1) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Compound I-263a was administered on a BIW schedule for 3 weeks till Day 14 (Day 0, 3, 7, 10, and 14), and anti-mPD-1 administered on a BIW schedule for 3 weeks till Day 14 (Day 0, 3, 7, 10, and 14).

Study 3: A 1.65 mg/mL stock solution of Compound I-263a was formulated weekly in 20% HPβCD and administered intravenously (IV) based on exact animal body weight on each day of treatment, using a dosing volume of 10 mL/kg body weight. Final doses received were 15 mg/kg. Dosing volume for Compound I-263a was 0.2 mL. Anti-mouse PD1 antibody (anti-mPD-1) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Compound I-263a was administered on a BIW schedule for 1 week (Day 1), and anti-mPD-1 administered on a BIW schedule for 2 weeks till Day 11 (Day 1, 4, 8, and 11).

Study 4: A 1.01 mg/mL stock solution of Compound I-263a was formulated weekly in 20% HPβCD and administered intravenously (IV) based on exact animal body weight on each day of treatment, using a dosing volume of 10 mL/kg body weight. Final doses received were 7.5 mg/kg. Dosing volume for Compound I-263a was 0.2 mL. Anti-mouse PD1 antibody (anti-mPD-1) (Bio X Cell, 10 Technology Drive, Suite 2B, West Lebanon, NH 03784) was formulated prior to each injection at 2.7 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Anti-mouse CTLA-4 antibody (anti-mCTLA-4) (Bio X Cell, 10 Technology Drive, Suite 2B, West Lebanon, NH 03784) was formulated prior to each injection at 2.7 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mCTLA-4 was 0.1 mL. Compound I-263a, anti-mPD-1, and anti-mCTLA-4 were administered on a BIW schedule for 3 weeks till Day 17 (Day 0, 3, 7, 10, 14, and 17).

Study 5: A 0.75 mg/mL stock solution of Compound I-263a was formulated weekly in 20% HPβCD and administered intravenously (IV) based on exact animal body weight on each day of treatment, using a dosing volume of 10 mL/kg body weight. Final doses received were 7.5 mg/kg. Dosing volume for Compound I-263a was 0.2 mL. Anti-mouse PD1 antibody (anti-mPD-1) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Anti-mouse CTLA-4 antibody (anti-mCTLA-4) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mCTLA-4 was 0.1 mL. Compound I-263a was administered on a BIW schedule for 3 weeks till Day 14 (Day 0, 3, 7, 10, and 14). Anti-mPD-1 was administered on a BIW schedule for 2 weeks till Day 10 (Day 0, 3, 7, and 10) in single agent treatment group, and on a BIW schedule for 3 weeks till Day 14 (Day 0, 3, 7, 10, and 14) in combination treatment group. Anti-mCTLA-4 was administered on a Q4D schedule for 3 cycles till Day 8 (Day 0, 4, and 8).

Study 6: A 0.75 mg/mL stock solution of Compound I-263a was formulated weekly in 20% HPβCD and administered intravenously (IV) based on exact animal body weight on each day of treatment, using a dosing volume of 10 mL/kg body weight. Final doses received were 7.5 mg/kg. Dosing volume for Compound I-263a was 0.2 mL. Anti-mouse PD1 antibody (anti-mPD-1) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Anti-mouse CTLA-4 antibody (anti-mCTLA-4) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mCTLA-4 was 0.1 mL. Compound I-263a was administered on a BIW schedule for 3 weeks till Day 14 (Day 0, 3, 7, 10, and 14). Anti-mPD-1 was administered on a BIW schedule for 3 weeks till Day 14 (Day 0, 3, 7, 10, and 14). Anti-mCTLA-4 was administered on a Q4D schedule for 3 cycles till Day 8 (Day 0, 4, and 8).

Study 7: A 0.75 mg/mL stock solution of Compound I-263a was formulated weekly in 20% HPβCD and administered intravenously (IV) based on exact animal body weight on each day of treatment, using a dosing volume of 10 mL/kg body weight. Final doses received were 7.5 mg/kg. Dosing volume for Compound I-263a was 0.2 mL. Anti-mouse PD1 antibody (anti-mPD-1) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Anti-mouse CTLA-4 antibody (anti-mCTLA-4) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mCTLA-4 was 0.1 mL. Compound I-263a was administered on a BIW schedule for 3 weeks till Day 17 (Day 0, 3, 7, 10, 14, and 17). Anti-mPD-1 was administered on a BIW schedule for 3 weeks till Day 17 (Day 0, 3, 7, 10, 14, and 17). Anti-mCTLA-4 was administered on a BIW schedule for 3 weeks till Day 17 (Day 0, 3, 7, 10, 14, and 17).

Study 8: A 0.75 mg/mL stock solution of Compound I-263a was formulated weekly in 20% HPβCD and administered intravenously (IV) based on exact animal body weight on each day of treatment, using a dosing volume of 10 mL/kg body weight. Final doses received were 7.5 mg/kg. Dosing volume for Compound I-263a was 0.2 mL. Anti-mouse PD1 antibody (anti-mPD-1) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Anti-mouse CTLA-4 antibody (anti-mCTLA-4) (Bio X Cell, 10 Technology Drive, Suite 2B, West Lebanon, NH 03784) was formulated prior to each injection at 2.0 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mCTLA-4 was 0.1 mL. Compound I-263a was administered on a BIW schedule for 3 weeks till Day 17 (Day 0, 3, 7, 10, 14, and 17). Anti-mPD-1 was administered on a BIW schedule for 3 weeks till Day 17 (Day 0, 3, 7, 10, 14, and 17). Anti-mCTLA-4 was administered on a BIW schedule for 3 weeks till Day 17 (Day 0, 3, 7, 10, 14, and 17).

Tumor Measurements:

Tumors were measured twice weekly using vernier calipers. Tumor volumes were calculated using standard equation: $V=W^2 \times L/2$, where V=volume, W=width, and L=length for the tumor. When mean tumor volumes reached approximately 60 mm$^3$ for study 1, 40 mm$^3$ for study 2, 50 mm$^3$ for study 3, 50 mm$^3$ for study 4, 30 mm$^3$ for study 5, 45 mm$^3$ for study 6, 50 mm$^3$ for study 7, 60 mm$^3$ for study 8. Mice were randomized into groups of 4 (n=8/group) in Study 1, groups of 4 (n=8/group) in Study 2, groups of 4 (n=8/group) in Study 3, groups of 6 (n=8/group) in Study 4, groups of 6 (n=8/group) in Study 5, groups of 6 (n=8/group) in Study 6, groups of 6 (n=8/group) in Study 7, and groups of 6 (n=8/group) in Study 8, and dosed with vehicle (20% HPBCD), Compound I-263a, anti-mPD-1, anti-mCTLA-4, or the combination of Compound I-263a plus anti-mPD-1 or anti-mCTLA-4 at various doses and schedules. Tumor size and body weight were measured twice a week for the duration of the study. Mice were euthanized when their tumor volumes exceeded approximately 2500 mm³ or when an individual tumor exceeded the humane end-point for size (the length of tumor exceeded 2 cm).

Results

Mouse syngeneic tumor models, performed as described in the general methods above, were used to assess the combination effect in vivo of Compound I-263a and anti-mPD-1 or anti-mCTLA-4.

Individual tumor growth curves are shown in FIGS. 1a, 1b, 1c, 2a, 2b, 2c, 3a, 3b, 3c, 4a, 4b, 4c, 4d, 4e, 5a, 5b, 5c, 5d, 5e, 6a, 6b, 6c, 6d, 6e, 7a, 7b, 7c, 7d, 7e, 8a, 8b, 8c, 8d, and 8e. Each chart shows the growth curves for each tumor treated with Vehicle, together with either individual tumor growth curves from mice treated with I-263a, or with a checkpoint inhibitor, or with a combination of I-263a and a checkpoint inhibitor.

Study 1: Mouse CT26 Syngeneic Tumor Model

In the CT26 syngeneic mouse colon fibroblast carcinoma-derived subcutaneous tumor model, mice were inoculated, randomized on Day 0 (6 days post inoculation), and treatments began on Day 1 for all groups.

Compound I-263a was tested at 7.5 mg/kg administered IV on a BIW (twice per week) schedule for one week (Day 1 and 4). Anti-mPD-1 was tested at 10 mg/kg administered IP on a BIW schedule for two weeks (Day 1, 4, 8, and 11). In the combination treatment group, Compound I-263a was administered first, followed immediately by the administration of anti-mPD-1. One group served as the vehicle-treated group (Group 1) which received IV treatment with the vehicle for Compound I-263a (20% HPβCD) on a BIW schedule for two weeks (Day 1, 4, 8, and 11).

Single agent treatment with Compound I-263a at 7.5 mg/kg BIW (Day 1 and Day 4) for one week, or anti-mPD-1 at 10 mg/kg BIW for two weeks (Day 1, 4, 8, and 11) did not show any tumor growth inhibition relative to vehicle-treated tumors (FIGS. 1a,b). Combination treatment with Compound I-263a at 7.5 mg/kg BIW (Day 1 and Day 4) for one week and anti-mPD-1 at 10 mg/kg BIW for two weeks (Day 1, 4, 8, and 11) resulted in marked antitumor activity, producing 2 complete tumor regressions (2 CRs), defined as the absence of any measurable tumor (FIG. 1c), achieved on day 7 and day 32 of treatment, and sustained to the end of monitoring on Day 35. In addition, combination treatment also resulted in one very prolonged tumor stasis to day 28. These results demonstrate markedly improved tumor growth inhibition in combination of I-263a with anti-mPD-1, relative to the activity of either single agent treatment.

Study 2: Mouse CT26 Syngeneic Tumor Model

In the CT26 syngeneic mouse colon fibroblast carcinoma-derived subcutaneous tumor model, mice were inoculated, randomized on Day 0 (4 days post inoculation), and treatments began on Day 0 for all groups.

Compound I-263a was tested at 7.5 mg/kg administered IV on a BIW (twice per week) schedule for three weeks till Day 14 (Day 0, 3, 7, 10, and 14). Anti-mPD-1 was tested at 10 mg/kg administered IP on a BIW schedule for three weeks till Day 14 (Day 0, 3, 7, 10, and 14). In the combination treatment group, Compound I-263a was administered first, followed immediately by the administration of anti-mPD-1. One group which served as the vehicle-treated group (Group 1) received IV treatment with the vehicle for Compound I-263a (20% HPβCD) on a BIW schedule for three weeks till Day 14 (Day 0, 3, 7, 10, and 14).

Single agent treatment with Compound I-263a at 7.5 mg/kg alone (IV) BIW×3 (till Day 14) schedule did not show any tumor growth inhibition in this study relative to vehicle-treated tumors (FIG. 2a). Treatment with anti-mPD-1 alone at 10 mg/kg (IP, BIW×3 till Day 14) resulted in two CRs, one achieved on day 14 of treatment the other on day 30, with no notable growth inhibition in the remaining 7 tumors (FIG. 2b). Combination treatment with I-263a at 7.5 mg/kg (IV, BIW×3 till Day 14) plus anti-mPD-1 at 10 mg/kg (IP, BIW×3 till Day 14) resulted in 1 CR achieved by day 9, with no marked growth inhibition in the remaining 8 tumors, indicating an absence of benefit from the combination of Compound I-263a with anti-mPD-1, relative to single agent activity achieved with anti-mPD-1, in this study (FIG. 2c).

Study 3: Mouse A20 Syngeneic Tumor Model

In the A20 syngeneic mouse B-cell lymphoma-derived subcutaneous tumor model, mice were inoculated, randomized on Day 0 (5 days post inoculation), and treatments began on Day 1 for all groups.

Compound I-263a was tested at 15 mg/kg administered IV on a QW (once per week) schedule for one week (Day 1). Anti-mPD-1 was tested at 10 mg/kg administered IP on a BIW schedule for two weeks till Day 11 (Day 1, 4, 8, and 11). In the combination treatment group, Compound I-263a was administered first, followed immediately by the administration of anti-mPD-1. One group which served as the vehicle-treated group (Group 1) received IV treatment with the vehicle for Compound I-263a (20% HPβCD) on a BIW schedule for two weeks till Day 11 (Day 1, 4, 8 and 11).

Single agent treatment with Compound I-263a at 15 mg/kg alone (IV) on QW×1 schedule demonstrated modest inhibition of the growth of A20 mouse B-cell lymphoma-derived subcutaneous tumors in female Balb/c mice, resulting in stasis of 2, out of 7 implanted, tumors to day 8 of treatment, followed by rapid growth (FIG. 3a). Treatment with anti-mPD-1 at 10 mg/kg (IP, BIW×2 till Day 11) resulted in tumor growth delay of 1 tumor from day 8-11, and 2 tumors on day 8 (FIG. 3b). Combination treatment with I-263a at 15 mg/kg (IV, BIW×1 till Day 11) plus anti-mPD-1 at 10 mg/kg (IP, BIW×2 till Day 11) resulted in 1 CR from day 4 that was sustained to the end of monitoring, and 4 tumor regressions that resumed growth on days 8, 11, 18 and 18, demonstrating improved tumor growth inhibition in the combination setting relative to the activity of either single agent treatment (FIG. 3c).

Study 4: Mouse WEHI-3 Syngeneic Tumor Model

In WEHI-3 syngeneic mouse myelomonocytic leukemia-derived subcutaneous tumor model, mice were inoculated, randomized on Day 0 (9 days post inoculation), and treatments began on Day 0 for all groups.

Compound I-263a was tested at 7.5 mg/kg administered IV on a BIW (twice per week) schedule for three weeks (Day 0, 3, 7, 10, 14, and 17). Anti-mPD-1 was tested at 10 mg/kg administered IP on a BIW schedule for three weeks ((Day 0, 3, 7, 10, 14, and 17)). Anti-mCTLA-4 was tested at 10 mg/kg administered IP on a BIW schedule for three weeks (Day 0, 3, 7, 10, 14, and 17). In the combination treatment group, Compound I-263a was administered first, followed immediately by the administration of anti-mPD-1 or anti-mCTLA-4. One group which served as the vehicle-treated group (Group 1) received IV treatment with the vehicle for Compound I-263a (20% HPβCD) on a BIW schedule for three weeks (Day 0, 3, 7, 10, 14, and 17).

Compound I-263a treatment at 7.5 mg/kg (IV) on a BIW×3 schedule had very little effect on the growth of WEHI-3 mouse myelomonocytic leukemia-derived subcutaneous tumors in female Balb/c mice, generating 2 slight tumor growth delays, out of a total of 8 implanted tumors, to day 14 (FIG. 4a). Similarly, treatment with anti-mPD-1 at 10 mg/kg (IP, BIW×3 till Day 17) resulted in 1 slight tumor growth delay to day 17 (FIG. 4b). Treatment with anti-mCTLA-4 at 10 mg/kg (IP, BIW×2 till Day 17) resulted in 2 slight tumor growth delays to days 14-17 (FIG. 4c). Combination treatment with I-263a at 7.5 mg/kg (IV, BIW×3 till Day 17) plus anti-mPD-1 at 10 mg/kg (IP, BIW×2 till Day 17) resulted in 2 CRs, one achieved at day 6, one at day 10, and one tumor growth delay to day 17, demonstrating markedly improved tumor growth inhibition following combination of I-263a with anti-mPD-1, relative to the activity of either single agent treatment (FIG. 4d). Combination treatment with I-263a at 7.5 mg/kg (IV, BIW×3 till Day 17) plus anti-mCTLA-4 at 10 mg/kg (IP, BIW×2 till Day 17) resulted in 1 CR, achieved at day 14, and one tumor growth delay to day 6, demonstrating improved tumor growth inhibition following combination of I-263a with anti-mCTLA4, relative to the activity of either single agent treatment (FIG. 4e).

Study 5: Mouse WEHI-3 Syngeneic Tumor Model

In WEHI-3 syngeneic mouse myelomonocytic leukemia-derived subcutaneous tumor model, mice were inoculated, randomized on Day 0 (4 days post inoculation), and treatments began on Day 0 for all groups.

Compound I-263a was tested at 7.5 mg/kg administered IV on a BIW (twice per week) schedule for three weeks till Day 14 (Day 0, 3, 7, 10, and 14). Anti-mPD-1 was tested at 10 mg/kg administered IP on a BIW schedule for 2 weeks till Day 10 (Day 0, 3, 7, and 10) in single agent treatment group, and on a BIW schedule for 3 weeks till Day 14 (Day 0, 3, 7, 10, and 14) in combination treatment group. Anti-mCTLA-4 was tested at 10 mg/kg administered on a Q4D schedule for 2 weeks till Day 8 (Day 0, 4, and 8). In the combination treatment group, Compound I-263a was administered first, followed immediately by the administration of anti-mPD-1 or anti-mCTLA-4. One group which served as the vehicle-treated group (Group 1) received IV treatment with the vehicle for Compound I-263a (20% HPβCD) on a QW schedule for two weeks (Day 0, and 7).

Compound I-263a treatment at 7.5 mg/kg (IV) on a BIW schedule for three weeks till Day 14 (Day 0, 3, 7, 10, and 14) demonstrated modest inhibition of the growth of WEHI-3 mouse myelomonocytic leukemia-derived subcutaneous tumors in female Balb/c mice, generating one tumor growth delay to 11-14 days, and multiple slight tumor growth delays to 7-11 days in 6 of the 8 implanted tumors (FIG. 5a). Treatment with anti-mPD-1 at 10 mg/kg (IP, BIW×2 till Day 10) did not result in any notable antitumor activity (FIG. 5b). Treatment with anti-mCTLA-4 at 10 mg/kg (IP, Q4D for 2 weeks till Day 8) resulted in no marked increase in tumor growth inhibition relative to treatment with vehicle (FIG. 5c). Combination treatment with I-263a at 7.5 mg/kg (IV, BIW×3 till Day 14) plus anti-mPD-1 at 10 mg/kg (IP, BIW×3 till Day 14) resulted in a modest tumor growth delay between days 9-16 for all 8 of the tumors implanted, not indicative of any marked improvement in tumor growth inhibition for the combination of I-263a with anti-mPD-1, compared to the single agent activity of I-263a (FIG. 5d). Combination treatment with I-263a at 7.5 mg/kg (IV, BIW×3 till Day 14) plus anti-mCTLA-4 at 10 mg/kg (IP, Q4D for 2 weeks till Day 8) resulted in tumor regression followed by stasis, starting on day 14, for 2 of the 8 implanted tumors, very marked tumor growth inhibition for 1 tumor beginning on day 9, and less marked tumor growth inhibition for 1 tumor beginning on day 7, demonstrating improved tumor growth inhibition following combination of I-263a with anti-mCTLA4, relative to the activity of either single agent treatment (FIG. 5e).

Study 6: Mouse JC Syngeneic Tumor Model

In JC syngeneic mouse breast adenocarcinoma-derived subcutaneous tumor model, mice were inoculated, randomized on Day 0 (12 days post inoculation), and treatments began on Day 0 for all groups.

Compound I-263a was tested at 7.5 mg/kg administered IV on a BIW (twice per week) schedule for three weeks till Day 14 (Day 0, 3, 7, 10, and 14). Anti-mPD-1 was tested at 10 mg/kg administered IP on a BIW schedule for 3 weeks till Day 14 (Day 0, 3, 7, 10, and 14). Anti-mCTLA-4 was tested at 10 mg/kg administered on a Q4D schedule for 3 cycles till Day 8 (Day 0, 4, and 8). In the combination treatment group, Compound I-263a was administered first, followed immediately by the administration of anti-mPD-1 or anti-mCTLA-4. One group which served as the vehicle-treated group (Group 1) received IV treatment with the vehicle for Compound I-263a (20% HPβCD) on a QW schedule for three weeks (Day 0, 7, and 14).

Treatment with Compound I-263a at 7.5 mg/kg (IV, BIW×3, till Day 14) demonstrated very little tumor growth inhibition, with one tumor, out of 8 implanted, showing slight growth delay from day 16-18 (FIG. 6a). Treatment with anti-mPD-1 at 10 mg/kg (IP, BIW×3, till Day 14) resulted in comparable slight antitumor activity with one tumor showing slight growth delay from day 16-18 (FIG. 6b). Treatment with anti-mCTLA-4 at 10 mg/kg (IP, Q4D× 3) resulted in tumor growth delay for 2 tumors from day 14-21 (FIG. 6c). Combination treatment with Compound I-263a at 7.5 mg/kg (IV, BIW×3, till Day 14) plus anti-mPD-1 at 10 mg/kg (IP, BIW×3, till Day 14) resulted in one marked tumor growth delay from day 14-18, demonstrating slightly improved tumor growth inhibition following combination of I-263a with anti-mPD-1, relative to the activity of either single agent treatment (FIG. 6d). Combination treatment with Compound I-263a at 7.5 mg/kg (IV, BIW×3, till Day 14) plus anti-mCTLA-4 at 10 mg/kg (IP, Q4D×3) resulted in tumor growth delay for 2 tumors from day 14-21, not indicative of any marked improvement in tumor growth inhibition for the combination of I-263a with anti-mCTLA-4, compared to the single agent activity of anti-mCTLA-4 (FIG. 6e).

Study 7: Mouse B16-F10 Syngeneic Tumor Model

In B16-F10 syngeneic mouse melanoma-derived subcutaneous tumor model, mice were inoculated, randomized on Day 0 (8 days post inoculation), and treatments began on Day 0 for all groups.

Compound I-263a was tested at 7.5 mg/kg administered IV on a BIW (twice per week) schedule for three weeks till Day 17 (Day 0, 3, 7, 10, 14, and 17). Anti-mPD-1 was tested at 10 mg/kg administered IP on a BIW schedule for 3 weeks till Day 17 (Day 0, 3, 7, 10, 14, and 17). Anti-mCTLA-4 was tested at 10 mg/kg administered on a BIW schedule for 3 weeks till Day 17 (Day 0, 3, 7, 10, 14, and 17). In the combination treatment group, Compound I-263a was administered first, followed immediately by the administration of anti-mPD-1 or anti-mCTLA-4. One group which served as the vehicle-treated group (Group 1) received IV treatment with the vehicle for Compound I-263a (20% HPβCD) on a BIW schedule for two weeks till Day 10 (Day 0, 3, 7, and 10).

Treatment with Compound I-263a at 7.5 mg/kg (IV, BIW×3, till Day 17) resulted in tumor growth delay for 2 of the 8 implanted tumors, from day 7 to day 10-12 (FIG. 7a). Treatment with anti-mPD-1 at 10 mg/kg (IP, BIW×3, till Day 17) resulted in tumor growth delay for 2 tumors from day 7-17, for 2 tumors from day 7-12, and for 1 tumor on day 10 (FIG. 7b). Treatment with anti-mCTLA-4 at 10 mg/kg (IP, BIW×3, till Day 17) resulted in 2 tumor growth delays from day 10-14, and 1 tumor growth delay on day 10 (FIG. 7c). Combination treatment with Compound I-263a at 7.5 mg/kg (IV, BIW×3, till Day 17) plus anti-mPD-1 at 10 mg/kg (IP, BIW×3, till Day 17) resulted in 1 tumor growth delay from day 7-14, indicative of no improvement in tumor growth inhibition for the combination of I-263a with anti-mPD-1, compared to the single agent activity of either agent (FIG. 7d). Combination treatment with Compound I-263a at 7.5 mg/kg (IV, BIW×3, till Day 17) plus anti-mCTLA-4 at 10 mg/kg (IP, BIW×3, till Day 17) resulted in 2 tumor growth delays on day 10, indicative of no improvement in tumor growth inhibition for the combination of I-263a with anti-mCTLA-4, compared to the single agent activity of either agent (FIG. 7e).

Study 8: Mouse MC38 Syngeneic Tumor Model

In MC38 syngeneic mouse colon adenocarcinoma-derived subcutaneous tumor model, mice were inoculated, randomized on Day 0 (5 days post inoculation), and treatments began on Day 0 for all groups.

Compound I-263a was tested at 7.5 mg/kg administered IV on a BIW (twice per week) schedule for three weeks till Day 17 (Day 0, 3, 7, 10, 14, and 17). Anti-mPD-1 was tested at 10 mg/kg administered IP on a BIW schedule for 3 weeks till Day 17 (Day 0, 3, 7, 10, 14, and 17). Anti-mCTLA-4 was tested at 10 mg/kg administered on a BIW schedule for 3 weeks till Day 17 (Day 0, 3, 7, 10, 14, and 17). In the combination treatment group, Compound I-263a was administered first, followed immediately by the administration of anti-mPD-1 or anti-mCTLA-4. One group which served as the vehicle-treated group (Group 1) received IV treatment with the vehicle for Compound I-263a (20% HPβCD) on a BIW schedule for 3 weeks till Day 10 (Day 0, 3, 7, 10, 14, and 17).

Treatment with Compound I-263a at 7.5 mg/kg (IV, BIW×3, till Day 17) resulted in tumor growth delay for 2 of the 8 implanted tumors, from day 7-18, and for 1 tumor from day 11-14 (FIG. 8a). Treatment with anti-mPD-1 at 10 mg/kg (IP, BIW×3, till Day 17) resulted in marked tumor growth delay with regressions for 3 tumors from days 9-18, 11-18, and 14-18, and tumor growth delay for 1 tumor from day 4-9, and 3 tumors between day 11-14 (FIG. 8b). Treatment with anti-mCTLA-4 alone at 10 mg/kg (IP, BIW×3, till Day 17) resulted in 2 tumor regressions from day 14-23 and day 16-21, as well as 1 tumor growth delay from day 4-20, and 2 tumor growth delays from day 11-14/16 (FIG. 8c). Combination treatment with Compound I-263a at 7.5 mg/kg (IV, BIW×3 till Day 17) plus anti-mPD-1 at 10 mg/kg (IP, BIW×3 till Day 17) resulted in 3 tumor regressions from day 7-11, day 7-14, and day 7-21, as well as 1 tumor growth delay from day 7-18, representing little, if any, combination benefit compared to the single agent activity of anti-mPD-1 (FIG. 8d). Combination treatment with Compound I-263a at 7.5 mg/kg (IV, BIW×3) plus anti-mCTLA-4 at 10 mg/kg (IP, BIW×3) resulted in 3 CR's from day 14, 25 and 35, durable to the end of monitoring on day 49, and one marked and prolonged growth delay from day 4-28, demonstrating marked improvement in tumor growth inhibition for the combination of I-263a with anti-mCTLA-4 (FIG. 8e).

Example 2: Clinical Study Evaluating Compound I-263a in Combination with a Checkpoint Inhibitor in Treatment of Patients with Non-Small Cell Lung Cancer, Cervical Cancer, or Colorectal Cancer A Phase 1b/2 clinical study will be conducted to evaluate the effects of a combination therapy, consisting of administration of a pembrolizumab intravenous infusion and of a Compound I-263a intravenous infusion, in adult patients with non-small cell lung cancer (NSCLC), cervical cancer, or microsatellite stable colorectal cancer (MSS-CRC).

The study will consist of a Screening Period (Day −28 to −1), a Treatment Period, an End-of-Treatment Visit and a Follow-Up visit 30 days after the last dose occurring when treatment is discontinued for any reason, and a Progression-Free Survival Follow-Up Period lasting for a maximum of 12 months for each patient after their last dose of study drug to monitor survival status. Day 1 of the study (baseline) will be defined as the first day a patient receives Compound I-263a. One cycle of treatment will be defined as 21 days. Patients will be asked to attend clinic visits at regular intervals during the study for safety and efficacy assessments.

Patients will receive treatment with Compound I-263a and pembrolizumab for up to 24 months or until confirmed disease progression, unacceptable toxicity, or any criterion for withdrawal from the study or study drugs occur. Treatment may be continued beyond disease progression, if the patient continues to experience clinical benefit.

The study will be conducted in 2 parts: a phase 1b portion and a phase 2 portion. The phase 1b portion of the study is a dose escalation study for Compound I-263a in combination with pembrolizumab at a fixed dose in patients with non-small cell lung cancer (NSCLC), cervical cancer, or microsatellite stable colorectal cancer (MSS-CRC) to determine the safety and tolerability of the combination. Dose escalation of Compound I-263a will be guided by a Bayesian Optimal Interval (BOIN) design, to determine the recommended phase 2 dose (RP2D) for the combination therapy. The RP2D will be determined from the collective experience in the clinic considering the safety data, preliminary PK data, preliminary pharmacodynamic data, and any early antitumor activity observed along with the statistical inference from the BOIN.

The Phase 2 portion of the study will determine the efficacy and safety of Compound I-263a in combination with pembrolizumab in patients with select cancers. The following cohorts will be enrolled: Cohort A: NSCLC adenocarcinoma; Cohort B: cervical cancer; Cohort C: MSS-CRC. Each cohort will be assessed separately using an adaptive 2 stage design for a single proportion.

For stage I, each cohort will be analyzed when a pre-specified number of patients have been enrolled and have the potential to have at least 1 post-treatment scan (i.e., after the first disease assessment, 2 months from cycle 1, day 1 (C1D1)). If the prespecified minimal response rate is not achieved in the first stage for a given cohort, that cohort will be closed to enrollment. However, if a clear clinical benefit has been observed for patients in the cohort, (e.g., a majority of patients have recorded stable disease at Week 8 and no complete response (CR) or partial response (PR) is recorded) then enrollment into stage II may be allowed for this cohort.

If the required response rate during stage I or a good clinical benefit is observed for a particular cohort as mentioned above, then additional patients will be enrolled in the second stage of the corresponding cohort until a predetermined number of additional patients for that cohort has been reached. The final analysis of the primary endpoints for each cohort will take place when all ongoing patients have had the opportunity complete the 6-month disease assessment.

The starting dose of Compound I-263a will be 3 mg administrated intravenously. Compound I-263a will be administered as a 1-hour intravenous (IV) infusion on Days 1, 4, 8, and 11 of a 21-day cycle. Pembrolizumab will be administered in a 200 mg dose on Day 1 of a 21-day cycle. Compound I-263a will be administered before pembrolizumab on days on which both Compound I-263a and pembrolizumab are given on the same visit day. At least 30 minutes should elapse between the completion of the infusion of the first study drug and the initiation of the infusion of the second study drug.

Compound I-263a will be administered as a 60±10 minute IV infusion. If infusion reactions are observed, the length of the infusion can be extended up to 4 hours for all patients without requiring a protocol amendment. Pembrolizumab will be administered as a 30±10 minute IV infusion. Dose escalations or dose reductions of pembrolizumab will not be allowed.

In the phase 1b portion of the study, only the dosing of Compound I-263a will be escalated. The starting dose level will be determined by the sponsor and participating investigators after review of the emerging safety data from the ongoing FIH single agent study (Study TAK-981-1002). The following dose levels of Compound I-263a will be considered: 25 mg, 40 mg, 60 mg, 90 mg, 120 mg, and 160 mg. Evaluation of lower or intermediate dose levels may be used if such measures are needed for patient safety or for a better understanding of toxicity, exposure, or pharmacodynamics of Compound I-263a.

Dose escalation will follow a Bayesian Optimal Interval (BOIN) design. Yuan Y, et al., *Clin. Cancer Res.* 22(17): 4291-301 (2016). According to the BOIN design, the decision to escalate or de-escalate dose of Compound I-263a is based on the cumulative dose-limiting toxicity (DLT) rate at the current dose level and the predetermined DLT rate threshold for dose escalation/de-escalation boundaries. The target DLT rate for this study is 0.3. The dose escalation and de-escalation rules for Compound I-263a are as follows: 1) if the observed DLT rate at the current dose level is ≤0.236, the dose level will be escalated; 2) if the observed DLT rate at the current dose level is ≥0.359, the dose level will be de-escalated; and 3) if the observed DLT rate at the current dose level is between 0.236 and 0.359, the dose level will stay the same.

Compound I-263a and pembrolizumab will be administered intravenously until confirmed disease progression or unacceptable toxicity. Toxicity will be evaluated according to the National Cancer Institute (NCI) Common Terminology Criteria for Adverse Events (CTCAE), version 5.0.

This study will enroll up to approximately 93 subjects, with approximately 24 subjects in the phase 1b dose escalation portion and approximately 27 to 69 subjects in the phase 2 portion of the study (approximately 9 to 23 for each of the three cohorts).

Phase 1b Primary Endpoints

The primary endpoints for the phase 1b trial will include: frequency, severity, and duration of treatment-emergent adverse events (TEAEs) and laboratory abnormalities for all dose groups according to NCI CTCAE Version 5.0; and occurrence of DLTs within the first 21 days of treatment in Cycle 1.

Phase 2 Primary Endpoints

The primary endpoints for the phase 2 trial will include: overall response rate (ORR) (complete response+partial response) as defined by the investigator according to Response Evaluation Criteria in Solid Tumors (RECIST) Version 1.1.

Phase 1b Secondary Endpoints

The secondary endpoints for the phase 1b trial will include: ORR, disease control rate (DCR), duration of response (DOR), time to progression (TTP), progression free survival (PFS), and overall survival (OS) as defined by the investigator according to RECIST Version 1.1 and Modified RECIST 1.1, and the RECIST consensus guideline (iRECIST).

Phase 2 Secondary Endpoints

The secondary endpoints for the phase 2 trial will include: frequency, severity, and duration of TEAEs and laboratory abnormalities for all dose groups according to NCI CTCAE Version 5.0; DCR, DOR, TTP, PFS, and OS as defined by the investigator according to RECIST Version 1.1 and iRECIST; ORR as assessed by the investigator according to iRECIST; and Compound I-263a plasma concentration-time data.

The trial will be conducted in conformance with Good Clinical Practices.

What is claimed is:

1. A method of treating a patient having cancer, comprising administering to a patient in need of said treating
   [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof, and
   a checkpoint inhibitor selected from an anti-PD-1 antibody and an anti-CTLA-4 antibody, wherein the cancer is selected from colorectal cancer, lymphoma, leukemia, and lung cancer; and
   wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, is administered on days 1, 4, 8, and 11 of a 21 day cycle.

2. The method of claim 1, wherein the checkpoint inhibitor is an anti-PD-1 antibody selected from the group consisting of nivolumab, pembrolizumab, lambrolizumab, pidilizumab, BMS-936559, and AMP-224.

3. The method of claim 1, wherein the checkpoint inhibitor is an anti-CTLA-4 antibody selected from the group consisting of ipilimumab and tremelimumab.

4. The method of claim 1, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, is administered orally, intravenously, or by intravenous infusion.

5. The method of claim 1, where [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate and the checkpoint inhibitor are administered sequentially in separate pharmaceutical compositions.

6. The method of claim 1, wherein the cancer is PD-1 positive cancer, a PD-L1 positive cancer, or a CTLA-4 positive cancer.

7. The method of claim 1, wherein the lung cancer is non-small cell lung cancer or small cell lung cancer, and wherein the non-small cell lung cancer is metastatic non-small cell lung cancer, metastatic squamous non-small cell lung cancer, or metastatic nonsquamous non-small cell lung cancer.

8. The method of claim 1, wherein the lymphoma is classical Hodgkin lymphoma or primary mediastinal large B-cell lymphoma.

9. The method of claim 1, wherein the colorectal cancer is microsatellite stable colorectal cancer.

10. The method of claim 1, wherein the checkpoint inhibitor is administered once every twelve weeks, once every four weeks, once every three weeks, once every two weeks, once every week, twice a week, three times a week, or daily.

11. The method of claim 10, wherein the checkpoint inhibitor is administered once every three weeks.

12. The method of claim 1, wherein the checkpoint inhibitor is administered on Day 1 of a treatment cycle.

13. The method of claim 1, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, and the checkpoint inhibitor are administered simultaneously on days 1, 4, 8, and 11 of a 21 day cycle.

14. The method of claim 1, wherein:
the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, is administered on days 1, 4, 8, and 11 of a 21 day cycle; and
the checkpoint inhibitor is separately administered once every twelve weeks, once every four weeks, once every three weeks, once every two weeks, once every week, twice a week, three times a week, or daily.

15. The method of claim 1, wherein:
the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, is administered on days 1, 4, 8, and 11 of a 21 day cycle; and
the checkpoint inhibitor is separately administered on day 1 of a 21 day cycle.

16. The method of claim 1, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, is administered in an amount of 90 mg on each day of dosing.

17. A method of treating a patient having cancer comprising administering to the patient in need of said treating [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate or a pharmaceutically acceptable salt thereof and pembrolizumab, wherein the [(1R,2S,4R)-4-{[5-({4-[(1R)-7-chloro-1, 2, 3, 4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, is administered in an amount of 90 mg on each day of dosing;
the [(1R,2S,4R)-4-{[5-{4-[(1R)-7-chloro-1, 2, 3, 4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, is administered twice a week for one or more treatment cycles, followed by administration once every week for one or more treatment cycles; and
the pembrolizumab is separately administered in an amount of 200 mg once every three weeks.

18. The method of claim 2, wherein the anti-PD-1 antibody is pembrolizumab.

* * * * *